(12) United States Patent
Röhl et al.

(10) Patent No.: US 6,228,810 B1
(45) Date of Patent: May 8, 2001

(54) PYRIDINE DERIVATIVES, PROCESS FOR PREPARING THE SAME AND THEIR USE FOR CONTROLLING ANIMAL PESTS AND HARMFUL FUNGI

(76) Inventors: Franz Röhl, Sabastian-Kneipp-Str. 17, 67105 Schifferstadt; Volker Harries, Immengärtenweg 29e, 67227 Frankenthal; Eberhard Ammermann, Von-Gagern-Str. 2, 64646 Heppenheim; Gisela Lorenz, Erlenweg 13, 67434 Neustadt; Siegfried Strathmann, Donnersbergstr. 9, 67117 Limburgerhof; Arne Ptock, Eichenstr. 23, 67067 Ludwigshafen; Hubert Sauter, Neckarpromenade 20, 68167 Mannheim; Wassilios Grammenos, Borsigsrt. 5, 67063 Ludwigshafen; Thomas Grote, Breslauer Str. 6, 67105 Schifferstadt; Herbert Bayer, D 3. 4, 68159 Mannheim; Reinhard Kirstgen, Karolinenstr. 51, 67434 Neustadt; Klaus Oberdorf, Bienenstr. 3, 69117 Heidelberg; Bernd Müller, Jean-Ganss-Str. 21, 67227 Frankenthal; Ruth Müller, Von-Wieser-Str. 1, 67159 Friedelsheim, all of (DE)

( * ) Notice: Subject to any disclaimer, the term of this patent is extended or adjusted under 35 U.S.C. 154(b) by 0 days.

(21) Appl. No.: 09/254,920

(22) PCT Filed: Aug. 29, 1997

(86) PCT No.: PCT/EP97/04710

§ 371 Date: Mar. 17, 1999

§ 102(e) Date: Mar. 17, 1999

(87) PCT Pub. No.: WO98/12179

PCT Pub. Date: Mar. 26, 1998

(30) Foreign Application Priority Data

Sep. 18, 1996 (DE) .............................. 196 38 038

(51) Int. Cl.[7] ........................ A01N 43/40; C07D 213/62; C07D 213/74; C07D 213/77

(52) U.S. Cl. ..................... 504/254; 504/255; 546/286; 546/290; 546/296; 546/297; 546/300; 546/306

(58) Field of Search .................................... 546/286, 290, 546/296, 297, 300, 306; 514/344, 345, 348, 349, 351, 353; 504/254, 255, 260

(56) References Cited

U.S. PATENT DOCUMENTS

| 5,633,268 | * | 5/1997 | Kirstgen et al. | 514/363 |
|---|---|---|---|---|
| 5,780,506 | | 7/1998 | Bayer et al. | 514/538 |
| 5,889,059 | | 3/1999 | Bayer et al. | 514/619 |

FOREIGN PATENT DOCUMENTS

| 95/06033 | 3/1995 | (WO) . |
|---|---|---|
| 95/21153 | 8/1995 | (WO) . |
| 95/21154 | 8/1995 | (WO) . |

OTHER PUBLICATIONS

Chem. Abstracts, Kirstgen et al. 1995:220182, 122:9667.*

* cited by examiner

*Primary Examiner*—Mukund J. Shah
*Assistant Examiner*—Ben Schroeder

(57) ABSTRACT

Pyridine derivatives of the formula I

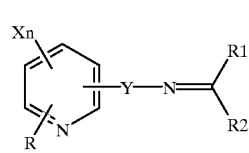

and their salts, their preparation, and their use for controlling animal pests and harmful fungi.

17 Claims, No Drawings

PYRIDINE DERIVATIVES, PROCESS FOR PREPARING THE SAME AND THEIR USE FOR CONTROLLING ANIMAL PESTS AND HARMFUL FUNGI

The present invention relates to pyridine derivatives of the formula I

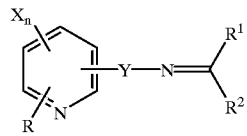

(I)

where the index and the substituents have the following meanings:

X is cyano, nitro, halogen, $C_1$–$C_4$-alkyl, $C_1$–$C_4$-haloalkyl, $C_1$–$C_4$-alkoxy, $C_1$–$C_4$-haloalkoxy and $C_3$–$C_6$-cycloalkyl;

n is 0, 1, 2 or 3, it being possible for the substituents X to be different when n is greater than 1;

Y is oxygen or nitrogen, the nitrogen atom having attached to it a hydrogen atom or a $C_1$–$C_4$-alkyl group;

R is $C(CO_2CH_3)=CHCH_3$, $C(CO_2CH_3)=CHOCH_3$, $C(CO_2CH_3)=NOCH_3$, $C(CONH_2)=NOCH_3$ or $C(CONHCH_3)=NOCH_3$;

$R^1$ is hydrogen, hydroxyl, cyano, halogen,
$C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_3$–$C_6$-cycloalkyl, $C_3$–$C_6$-cycloalkyl-$C_1$–$C_4$-alkyl,
aryl, aryl-$C_1$–$C_4$-alkyl, aryloxy-$C_1$–$C_4$-alkyl and aryl-$C_1$–$C_4$-alkoxy, it being possible for the aromatic rings to be partially or fully halogenated and/or to have attached to them one to three of the following radicals: cyano, nitro, $C_1$–$C_6$-alkyl, $C_1$–$C_6$-haloalkyl, $C_1$–$C_6$-alkoxy, $C_1$–$C_6$-haloalkoxy, and $C(CH_3)=N-A^1-R^a$;

$R^a$ is $C_1$–$C_6$-alkyl, $A^1$ is oxygen or nitrogen, the nitrogen atom having attached to it a hydrogen atom or a $C_1$–$C_4$-alkyl group;

$R^2$ is hydrogen, cyano,
unsubstituted or substituted alkyl, alkenyl, alkynyl, cycloalkyl, heterocyclyl, aryl and hetaryl;
unsubstituted or substituted alkoxy, alkenyloxy, alkynyloxy, cycloalkoxy, heterocyclyloxy, aryloxy and hetaryloxy;
unsubstituted or substituted arylthio and hetarylthio;
—Q—C($R^3$)=N—$Y^1$—$R^4$ or —Q—O—N=$CR^5R^6$
where
Q is a direct bond, $CH_2$, $CH(CH_3)$, $CH(CH_2CH_3)$ or 1,1-cyclopropyl;
$Y^1$ is oxygen or nitrogen, the nitrogen atom having attached to it a hydrogen atom or a $C_1$–$C_4$-alkyl group;
$R^3$ is one of the groups mentioned for $R^1$, or unsubstituted or substituted cycloalkoxy, heterocyclyloxy, aryloxy, hetaryloxy, arylthio and hetarylthio;
$R^4$ is unsubstituted or substituted $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_2$–$C_{10}$-alkynylcarbonyl or $C_1$–$C_{10}$-alkylsulfonyl; unsubstituted or substituted aryl, hetaryl, arylcarbonyl, hetarylcarbonyl, arylsulfonyl or hetarylsulfonyl;

$R^5$, $R^6$ are methyl, ethyl, phenyl and benzyl, it being possible for the aromatic rings to have attached to them one to three of the following substituents: cyano, nitro, halogen, $C_1$–$C_6$-alkyl, $C_1$–$C_6$-haloalkyl, $C_1$–$C_6$-alkoxy and $C_1$–$C_6$-haloalkoxy;

$R^1$ and $R^2$ together with the carbon atom to which they are bonded are a four- to eight-membered ring which, in addition to carbon atoms, can contain one or two oxygen and/or sulfur atoms and/or NH and/or N($C_1$–$C_4$-alkyl) groups and whose carbon atoms can have attached to them one of the following substituents: halogen, $C_1$–$C_6$-alkyl or $C_1$–$C_4$-alkoxyimino;

$R^1$ and $R^2$ not being bonded simultaneously to the carbon atom via hetero atoms;

and the salts thereof.

Moreover, the invention relates to processes for the preparation of these compounds, to compositions comprising them, and to their use for controlling animal pests and harmful fungi.

Compounds of the type I where Y is oxygen and $R^2$ is unsubstituted or substituted aryl or hetaryl are described in the literature in general form as fungicides (WO-A 95/06,033). However, only compounds which have attached to them an unsubstituted or substituted aryl group which is bonded to the pyridyl radical via oxygen, sulfur, oxymethylene or $CH_2$—$ON=C(CH_3)$— are disclosed in this publication.

It was an object of the present invention to provide compounds with an improved activity and a broadened spectrum of action.

We have found that this object is achieved by the compounds I defined at the outset. Furthermore, we have found processes for the preparation of these compounds, compositions comprising them, and their use for controlling animal pests and harmful fungi.

The compounds I can be prepared by various routes, it generally being irrelevant whether the group —Y—N=$CR^1R^2$ or the radical R is first synthesized.

1. In the preparation of the compounds I where R is $C(CO_2CH_3)=CHCH_3$, $C(CO_2CH_3)=CHOCH_3$ or $C(CO_2CH_3)=NOCH_3$, a procedure is followed, for example, in which a pyridinecarboxylic acid of the formula IIa is first converted in a manner known per se into the acid chloride IIb and subsequently into the acid cyanide IIc; IIc is reacted via a Pinner reaction to give the corresponding α-keto ester IIIa; IIIa is subsequently reacted with an oxime of the formula IV in the presence of a base to give the corresponding α-keto ester IIIb; and IIIb is subsequently converted in a manner known per se either a) with a Wittig or Wittig-Horner reagent of the formula Va into the corresponding compound Ia [R=C($CO_2CH_3$)=$CHOCH_3$], or b) with a Wittig or Wittig-Horner reagent of the formula Vb into the corresponding compound Ib [R=C($CO_2CH_3$)=$CHCH_3$], or c) with O-methylhydroxylamine or a salt thereof (Vc) into the corresponding compound Ic [R=C($CO_2CH_3$)=$NOCH_3$].

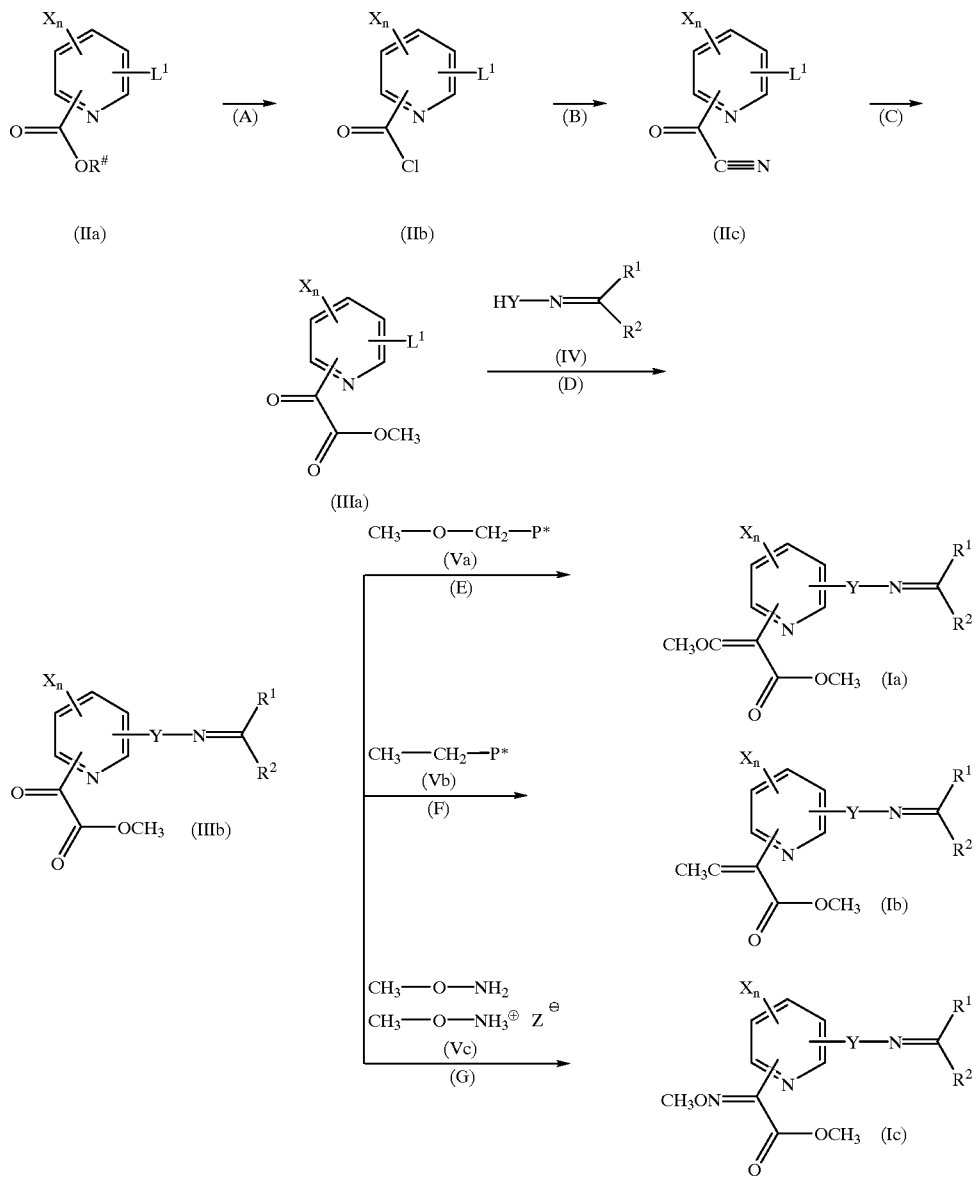

L¹ in formula IIa is a nucleophilically exchangeable leaving group such as [lacuna]

R# in formula IIa is hydrogen or a $C_1$–$C_4$-alkyl group, in particular hydrogen.

P* in formulae Va and Vb is a phosphonate or a phosphonium halide radical which is suitable for a Wittig or Wittig-Horner reaction, in particular $PO(OCH_3)_2$, $PO(OCH_2CH_3)_2$ and $[(C_6H_5)_3P^+Cl^-]$.

Z⁻ in formula Vc is the anion of an inorganic acid, especially a halide anion, in particular chloride.

1A. The reaction of the pyridinecarboxylic acid IIa to give the acid chloride IIb is carried out in a manner known per se [Houben-Weyl, Supplementary Volume 5, p.59 et seq., 225 et seq. and 664 et seq.; J.Heterocycl.Chem, 30, (1993), 771] by means of customary chlorinating agents at from 0° C. to 150° C., preferably 10° C. to 100° C., in the presence or absence of an inert organic solvent.

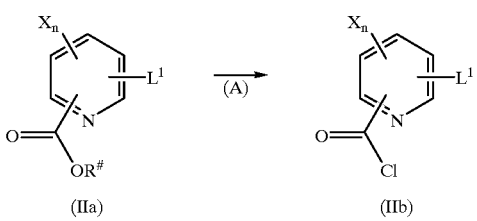

Suitable chlorinating agents are all reagents customary for this purpose, in particular $SOCl_2$, $(COCl)_2$, $PCl_3$, $AlCl_3$ and $PCl_5$. In general, the chlorinating agents are used in an excess or, if appropriate, as the solvent.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, nitrites such as acetonitrile and propionitrile, especially preferably halogenated hydrocarbons or mixtures of these.

In general, the starting materials are reacted with each other in equimolar amounts. It may be advantageous for the yield to employ the chlorinating agent in an excess based on IIa.

The starting materials required for the preparation of the compounds I which are not already known from the literature [WO-A 95/06,033; J.Heterocycl.Chem. 30, (1993), 717; DE Appl. No. 19 540 989.2; DE Appl. No. 19 548 370.7] can be prepared in accordance with the literature cited.

1B. The reaction of the acid chloride IIb to give the cyanide IIc is carried out in a manner known per se [DE Appl. No. 19 603 990.8] at from 0° C. to 150° C., preferably 10° C. to 100° C., using an inorganic cyanide in an inert organic solvent, if appropriate as a mixture with water, in the presence of a customary phase-transfer catalyst (eg. tetraalkylammonium halides such as tetrabutylammonium chloride or tetrabutylammonium bromide).

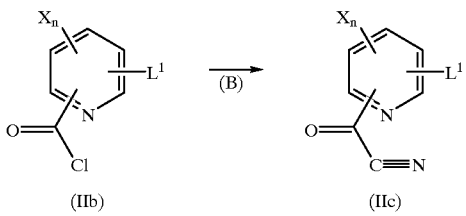

Suitable inorganic cyanides are cyanides of metals of the first main group or of the sub-groups of the Periodic Table, for example lithium, sodium, potassium, copper and silver, in particular copper and sodium, and inorganic cyanides such as trimethylsilyl cyanide.

Suitable solvents are aromatic hydrocarbons such as toluene, o-, m- and p-xylene, nitrites such as acetonitrile and propionitrile, especially preferably methylene chloride and acetonitrile. Mixtures of these may also be used.

When using organic cyanides such as trimethylsilyl cyanide, it may be advantageous to carry out the reaction in the presence of an acidic catalyst. Acidic catalysts which are used are Lewis acids such as boron trifluoride, aluminum trichloride, iron(III) chloride, tin(IV) chloride, titanium(IV) chloride and zink(II) chloride, in particular tin(IV) chloride.

In general, the starting materials are reacted with each other in equimolar amounts. It may be advantageous for the yield to employ the cyanide in an excess based on IIb.

1C. The reaction of the cyanide IIc to give the α-keto ester IIIa is carried out in a manner known per se via a Pinner reaction [DE Appl. No. 19 603 990.8] at from 0° C. to 150° C., preferably 10° C. to 100° C., in the presence of an acid in methanol as the solvent.

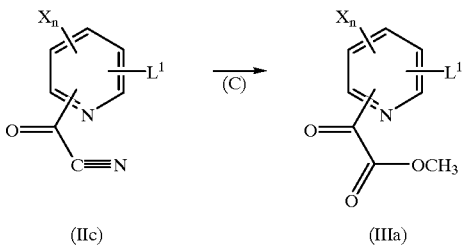

Acids which are used are inorganic acids such as hydrofluoric acid, hydrochloric acid, hydrobromic acid, sulfuric acid and perchloric acid. In general, the acids are used in equimolar amounts or in an excess.

The reaction is usually carried out in such a way that the cyanide IIc is first hydrolyzed with aqueous acids (eg. hydrochloric acid) at from 10° C. to 100° C. and the product is subsequently esterified by reaction with methanol, in the presence or absence of a reaction auxiliary (eg. sulfuric acid) and in the presence or absence of a diluent (eg. toluene) at from 10° C. to 150° C. by methods similar to known processes [EP-A 493 711].

1D. The reaction of the α-keto ester IIIa with the oxime of the formula IV is carried out in a manner known per se at from 0° C. to 150° C., preferably 10° C. to 100° C., in an inert organic solvent in the presence of a base.

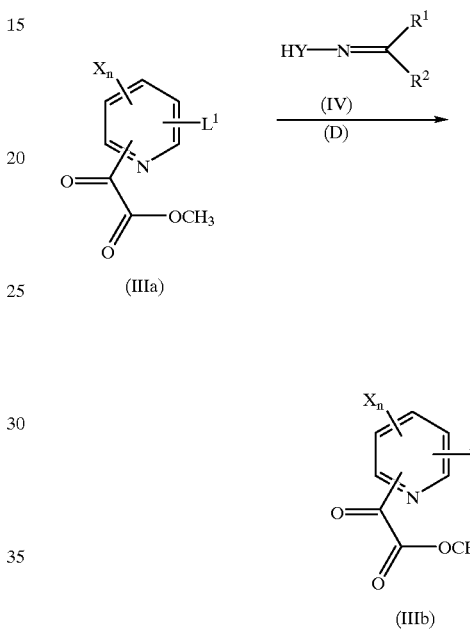

Suitable solvents are alcohols such as methanol, ethanol, n-propanol, isopropanol, n-butanol and tert-butanol, and also dimethyl sulfoxide, dimethylformamide and dimethylacetamide, especially preferably dimethylformamide, dimethylacetamide, dimethyl sulfoxide and tert-butanol. Mixtures of these may also be used.

Bases which are generally suitable are inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, and also alkali metal hydrogen carbonates such as sodium hydrogen carbonate, and also alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. Potassium tert-butoxide, potassium carbonate and sodium methoxide are especially preferred.

In general, the bases are used in equimolar amounts, in an excess or, if appropriate, as the solvent.

In general, the starting materials are reacted with each other in equimolar amounts. It may be advantageous for the yield to employ IV in an excess based on IIIa.

1E. The reaction of the α-keto ester IIIb to give the compound Ia is carried out in a manner known per se [EP-A 513 580; tetrahedron 3727 (1988); GB-A 2,172,595; DE Appl. No. 19 603 990.8] via a Wittig or Wittig-Horner reaction at from 0° C. to 150° C., preferably 10° C. to 100° C., in an inert organic solvent in the presence of a base.

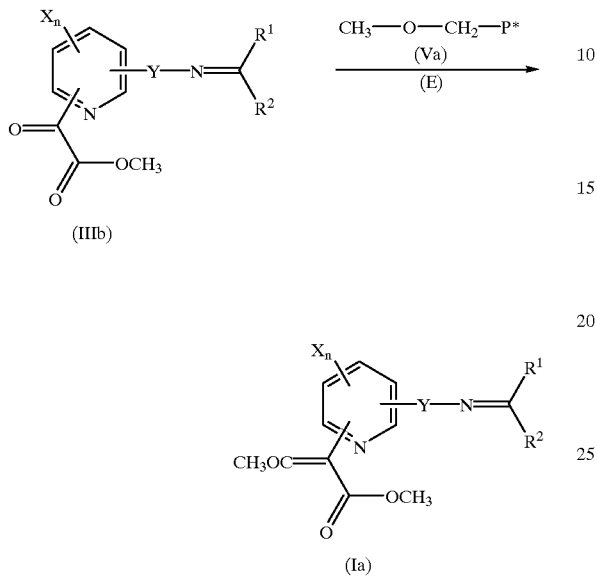

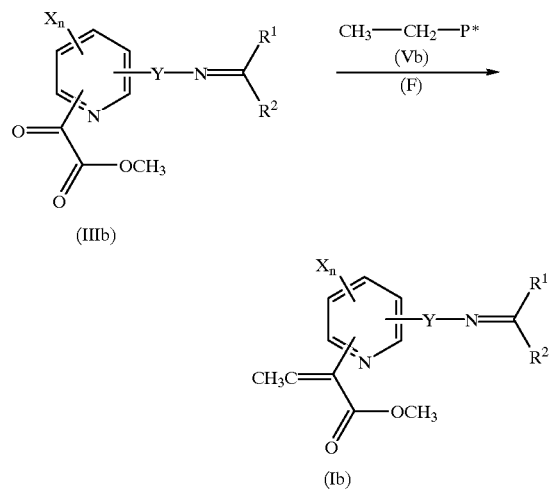

Suitable solvents are ethers such as diethyl ether, diisopropyl ether, tert-butyl methyl ether, dioxane, anisole and tetrahydrofuran, alcohols such as methanol, ethanol, n-propanol, isopropanol, n-butanol and tert-butanol, and also dimethyl sulfoxide, dimethylformamide and dimethylacetamide, especially preferably dimethylformamide, dimethylacetamide and tetrahydrofuran. Mixtures of these may also be used.

Bases which are suitable are, generally, inorganic compounds such as alkali metal hydroxides and alkaline earth metal hydroxides such as lithium hydroxide, sodium hydroxide, potassium hydroxide and calcium hydroxide, alkali metal carbonates and alkaline earth metal carbonates such as lithium carbonate and calcium carbonate, and alkali metal hydrogen carbonates such as sodium hydrogen carbonate, organometallic compounds, in particular alkali metal alkyls such as methyllithium, butyllithium and phenyllithium, alkylmagnesium halides such as methylmagnesium chloride, and alkali metal alkoxides and alkaline earth metal alkoxides such as sodium methoxide, sodium ethoxide, potassium ethoxide, potassium tert-butoxide and dimethoxymagnesium. Sodium methoxide and potassium tert-butoxide are especially preferred.

In general, the bases are used in equimolar amounts, in an excess or, if appropriate, as the solvent.

In general, the starting materials are reacted with each other in equimolar amounts. It may be advantageous for the yield to employ Va in an excess based on IIIb.

1F. The reaction of the α-keto ester IIIb to give the compound Ib is carried out a manner known per se (cf. the references cited under 1E.) via a Wittig or Wittig-Horner reaction at from 0° C. to 150° C., preferably 10° C. to 100° C., in an inert organic solvent in the presence of a base.

Suitable solvents are ethers such as diethyl ether, diisopropyl ether, tert-butyl methyl ether, dioxane, anisole and tetrahydrofuran, alcohols such as methanol, ethanol, n-propanol, isopropanol, n-butanol and tert-butanol, and also dimethyl sulfoxide, dimethylformamide and dimethylacetamide, especially preferably dimethyl sulfoxide, dimethylformamide, dimethylacetamide and tetrahydrofuran. Mixtures of these can also be used.

Bases which are suitable are, generally, inorganic compounds such as alkali metal hydroxides and alkaline earth metal hydroxides such as lithium hydroxide, sodium hydroxide, potassium hydroxide and calcium hydroxide, alkali metal carbonates and alkaline earth metal carbonates such as lithium carbonate and calcium carbonate, and alkali metal hydrogen carbonates such as sodium hydrogen carbonate, organometallic compounds, in particular alkali metal alkyls such as methyllithium, butyllithium and phenyllithium, alkylmagnesuim halides such as methylmagnesium chloride, and alkali metal alkoxides and alkaline earth metal alkoxides such as sodium methoxide, sodium ethoxide, potassium ethoxide, potassium tert-butoxide and dimethoxymagnesium. Sodium methoxide and potassium tert-butoxide are especially preferred.

In general, the bases are used in equimolar amounts, in an excess or, if appropriate, as the solvent.

In general, the starting materials are reacted with each other in equimolar amounts. It may be advantageous for the yield to employ Vb in an excess based on IIb.

1G. The reaction of the α-keto ester IIIb to give the compound Ic is carried out in a manner known per se (EP-A 493 711) at from 0° C. to 150° C., preferably 10° C. to 100° C., in an inert organic solvent in the presence of a base using O-methylhydroxylamine or a salt thereof (Vc).

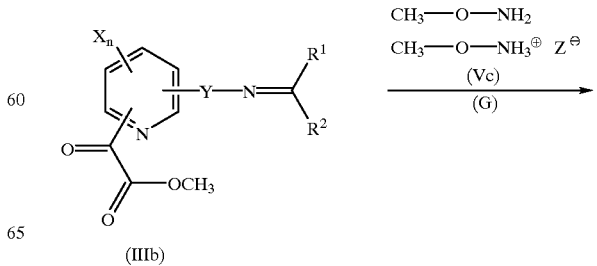

-continued

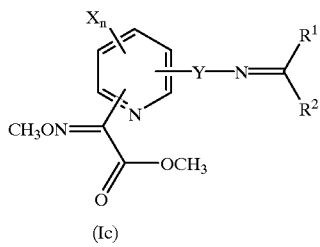

(Ic)

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, alcohols such as methanol, ethanol, n-propanol, isopropanol, n-butanol and tert-butanol, and also dimethyl sulfoxide, dimethylformamide and dimethylacetamide, especially preferably methanol. Mixtures of these may also be used.

Bases which are generally suitable are inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, furthermore organic bases, eg. tertiary amines such as trimethylamine, triethylamine, tri-isopropylethylamine and N-methylpiperidine, pyridine, substituted pyridines such as collidine, lutidine and 4-dimethylaminopyridine, and also bicyclic amines. Tertiary amines are especially preferred.

The bases are generally employed in catalytic amounts, but they can also be used in equimolar amounts, in an excess or, if appropriate, as the solvent.

In general, the starting materials are reacted with each other in equimolar amounts. It may be advantageous for the yield to employ Vc in an excess based on IIIb.

2. In a further process, the compounds Ia, Ib and Ic are obtained, for example, by converting a pyridine derivative of the formula VI with a compound VII in a manner known per se in the presence of a catalyst into the corresponding pyridine derivative of the formula VIII and subsequently reacting VIII with an oxime of the formula IV in the presence of a base to give Ia, Ib or Ic. The pyridine derivatives VIII are also obtained in a similar manner by reacting a halogenated pyridine of the formula VIa with an organometallic compound VIIa.

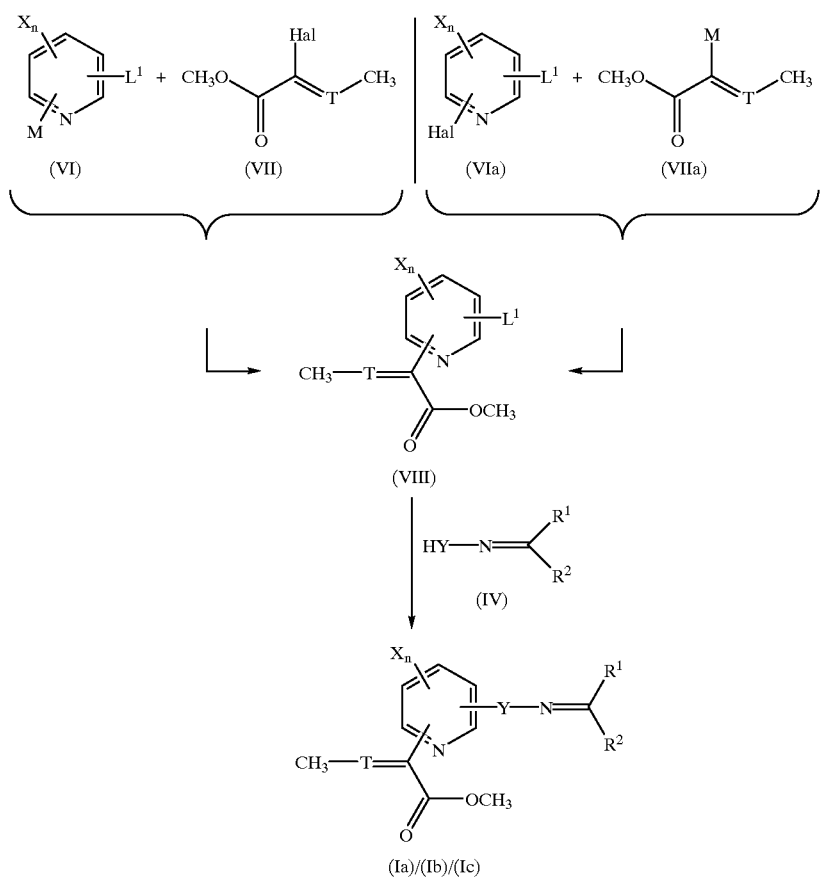

$L^1$ in formulae VI, VIa and VIII is a nucleophilically exchangeable leaving group, such as aliphatic and aromatic sulfonates and halogen atoms, in particular fluorine and chlorine.

M in formulae VI and VIIa is an organometallic radical, eg. tributyltin(IV), trimethyltin(IV), zink(II) chloride (ZnCl) or boron(II) hydroxide [B(OH)$_2$], in particular tributyltin (IV) and boron(II) hydroxide [B(OH)$_2$]. With a view to the high toxicity of trimethyltin(IV), this substance is preferred only under certain conditions.

T in formulae VII, VIIa, VIII and Ia, Ib or Ic is CH, CHO or NO.

Hal in formulae VIa and VII is a halogen atom, in particular bromine or iodine.

2A. The reaction of the compound VI, or VIa, with the carbonyl derivative VII, or VIIa, is carried out in a manner known per se at from 0° C. to 150° C., preferably 10° C. to 100° C., in an inert organic solvent in the presence or absence of a cocatalyst such as CuI. In the event that the reaction is carried out with the compound VI or VIIa where M is B(OH)$_2$, the reaction is carried out in the presence of at least equimolar amounts of a base.

In general, the starting materials are reacted with each other in equimolar amounts. It may be advantageous for the yield to employ VI or VIIa in an excess based on VII or VIa.

Those starting materials required for the preparation of the compounds I which are not already known from the literature [WO-A 95/20,569; WO-A 94/24,085; Synlett (1) (1995) 32–33; Synlett (4) (1996) 356–357; J.Gen.Chem.USSR 59 (1989) 264–272; Heterocycles 31 (1990) 1543–1548; Tetrahedron 49 (1993) 49–64; J.Chem.Res.Miniprint 11 (1980) 4658–4667] can be prepared in accordance with the literature cited.

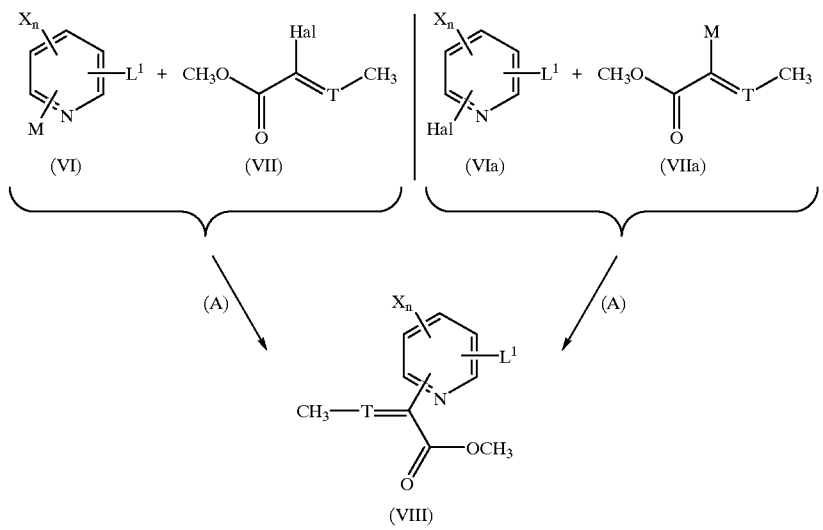

Suitable solvents are aromatic hydrocarbons such as toluene, o-, m- and p-xylene, ethers such as diethyl ether, diisopropyl ether, tert-butyl methyl ether, dioxane, anisole and tetrahydrofuran, and also dimethylformamide and dimethylacetamide, especially preferably N-methylpyrrolidone. Mixtures of the abovementioned solvents can also be used.

Bases which are suitable for coupling compounds where M is B(OH)$_2$ are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal carbonates and alkaline earth metal carbonates such as lithium carbonate and calcium carbonate, and also alkali metal hydrogen carbonates such as sodium hydrogen carbonate, and also alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, triisopropylethylamine and N-methylpiperidine, pyridine, substituted pyridines such as collidine, lutidine and 4-dimethylaminopyridine, and also bicyclic amines. Sodium carbonate, sodium hydrogen carbonate and lithium hydroxide are especially preferred.

In general, the bases are used in equimolar amounts, in an excess or, if appropriate, as the solvent.

2B. The reaction of the compound VIII with the oxime derivative IV is carried out in a manner known per se at from 0° C. to 150° C., preferably 10° C. to 100° C., in an inert organic solvent in the presence of a base.

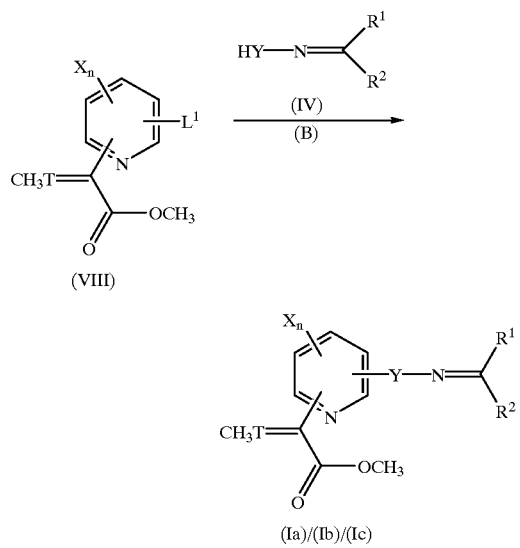

Suitable solvents are alcohols such as methanol, ethanol, n-propanol, isopropanol, n-butanol and tert-butanol, and also dimethyl sulfoxide, dimethylformamide and dimethylacetamide, especially preferably dimethyl sulfoxide, dimethylformamide and dimethylacetamide. Mixtures of these can also be used.

Bases which are suitable are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal carbonates and alkaline earth metal carbonates such as lithium carbonate and calcium carbonate, and also alkali metal hydrogen carbonates such as sodium hydrogen carbonate, and also alkali metal alkoxides and alkaline earth metal alkoxides such as sodium methoxide, sodium ethoxide, potassium ethoxide, potassium tert-butoxide and dimethoxymagnesium, furthermore organic bases, eg. tertiary amines such as trimethylamine, triethylamine, tri-isopropylethylamine and N-methylpiperidine, pyridine, substituted pyridines such as collidine, lutidine and 4-dimethylaminopyridine, and also bicyclic amines. Potassium tert-butoxide, sodium methoxide and potassium carbonate are especially preferred.

In general, the bases are used in equimolar amounts, in an excess or, if appropriate, as the solvent.

In general, the starting materials are reacted with each other in equimolar amounts. It may be advantageous for the yield to employ IV in an excess based on VIII.

2.1 In accordance with the above-described reaction conditions, the compounds Ia, Ib and Ic are also especially preferably obtained by first converting the pyridine VIa with the oxime IV into the corresponding derivative VIIIa and subsequently reacting VIIIa with VIIa to give Ia, Ib or Ic.

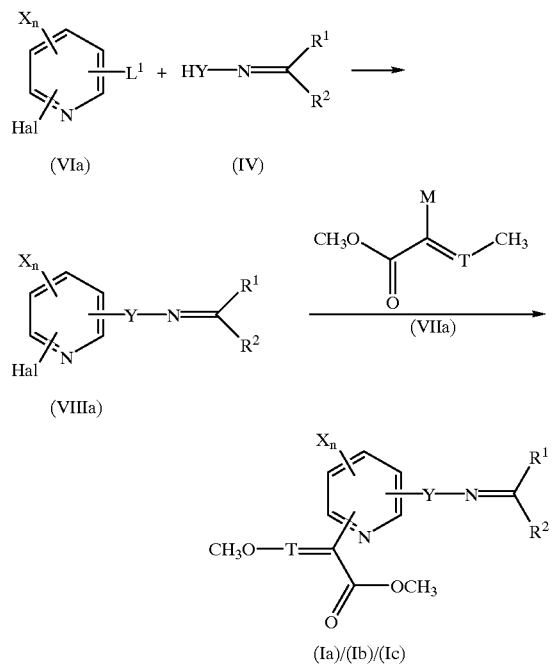

3. The compounds of the formula I where R is C(CONHCH$_3$)=NOCH$_3$ are advantageously obtained by reacting a compound of the formula Ic in a manner known per se with methylamine or a salt thereof (IX).

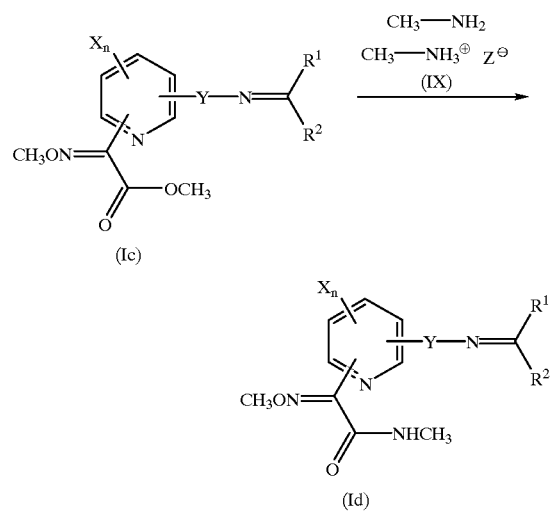

Z$^-$ in formula IX is the anion of an inorganic acid, especially a halide anion, in particular chloride.

This reaction is carried out in a manner known per se (EP-A 477 631) at from 0° C. to 150° C., preferably 10° C. to 100° C., in an inert organic solvent and in the presence or absence of a base.

Suitable solvents are aliphatic hydrocarbons such as pentane, hexane, cyclohexane and petroleum ether, aromatic hydrocarbons such as toluene, o-, m- and p-xylene, halogenated hydrocarbons such as methylene chloride, chloroform and chlorobenzene, ethers such as diethyl ether, diisopropyl ether, tert-butyl methyl ether, dioxane, anisole and tetrahydrofuran, nitriles such as acetonitrile and propionitrile, alcohols such as methanol, ethanol, n-propanol, isopropanol, n-butanol and tert-butanol, and also dimethyl sulfoxide, dimethylformamide and dimethylacetamide, especially preferably tetrahydrofuran. Mixtures of these can also be used.

Suitable bases are, generally, inorganic compounds such as alkali metal hydroxides and alkaline earth metal hydroxides such as lithium hydroxide, sodium hydroxide, potassium hydroxide and calcium hydroxide, alkali metal oxides and alkaline earth metal oxides such as lithium oxide, sodium oxide, calcium oxide and magnesium oxide, alkali metal carbonates and alkaline earth metal carbonates such as lithium carbonate and calcium carbonate, and also alkali metal hydrogen carbonates such as sodium hydrogen carbonate, furthermore organic bases, eg. tertiary amines such as trimethylamine, triethylamine, tri-isopropylethylamine and N-methylpiperidine, pyridine, substituted pyridines such as collidine, lutidine and 4-dimethylaminopyridine, and also bicyclic amines. Tertiary amines are especially preferred.

The bases are generally used in equimolar amounts, in an excess or, if appropriate, as the solvent.

In general, the starting materials are reacted with each other in equimolar amounts. It may be advantageous for the yield to employ IX in an excess based on Ic.

The reaction mixtures are worked up in the customary manner, for example by mixing with water, separating the phases and, if appropriate, chromatographic purification of the crude product. In some cases, the intermediates and end products are obtained in the form of colorless or pale brown viscous oils which are freed from volatile components or purified under reduced pressure and at moderately elevated temperatures. If the intermediates and end products are obtained as solids, they can also be purified by recrystallization or digestion.

In the definitions of the symbols given in the above formulae, collective terms were used which generally represent the following substituents:

Halogen: fluorine, chlorine, bromine and iodine;

Alkyl: saturated straight-chain or branched hydrocarbon radicals having 1 to 4, 6 or 10 carbon atoms, eg. $C_1$–$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

Haloalkyl: straight-chain or branched alkyl groups having 1 to 4, 6 or 10 carbon atoms (as mentioned above), it being possible for some or all of the hydrogen atoms in these groups to be replaced by halogen atoms as mentioned above, eg. $C_1$–$C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl;

Alkylcarbonyl: an alkyl group having 1 to 6 or 10 carbon atoms (as mentioned above) which is bonded to the skeleton via a carbonyl group (—CO—);

Alkylsulfonyl: a straight-chain or branched alkyl group having 1 to 6 or 10 carbon atoms (as mentioned above) which is bonded to the skeleton via a sulfonyl group (—SO$_2$—);

Alkylsulfoxyl: a straight-chain or branched alkyl group having 1 to 6 carbon atoms (as mentioned above) which is bonded to the skeleton via a sulfoxyl group (—SO$_3$—);

Alkoxy: straight-chain or branched alkyl groups having 1 to 4 or 6 carbon atoms (as mentioned above) which are bonded to the skeleton via an oxygen atom (—O—);

Haloalkoxy: straight-chain or branched haloalkyl groups having 1 to 4, 6 or 10 carbon atoms (as mentioned above) which are bonded to the skeleton via an oxygen atom (—O—);

Alkoxycarbonyl: an alkoxy group having 1 to 6 carbon atoms (as mentioned above) which is bonded to the skeleton via a carbonyl group (—CO—);

Alkoxyimino: straight-chain or branched alkyl groups having 1 to 4 carbon atoms (as mentioned above) which are bonded to the skeleton via an oxyimino group (—ON=);

Alkylthio: straight-chain or branched alkyl groups having 1 to 6 carbon atoms (as mentioned above) which are bonded to the skeleton via a sulfur atom (—S—);

Alkylamino: a straight-chain or branched alkyl group having 1 to 6 carbon atoms (as mentioned above) which is bonded to the skeleton via an amino group (—NH—);

Dialkylamino: two straight-chain or branched alkyl groups, independent of one another, which have in each case 1 to 6 carbon atoms (as mentioned above) and are bonded to the skeleton via a nitrogen atom;

Alkylaminocarbonyl: an alkylamino group having 1 to 6 carbon atoms (as mentioned above) which is bonded to the skeleton via a carbonyl group (—CO—);

Dialkylaminocarbonyl: a dialkylamino group having two $C_1$–$C_6$-alkyl groups (as mentioned above), independent of one another, which is bonded to the skeleton via a carbonyl group (—CO—);

Alkylaminothiocarbonyl: an alkylamino group having 1 to 6 carbon atoms (as mentioned above) which is bonded to the skeleton via a thiocarbonyl group (—CS—);

Dialkylaminothiocarbonyl: a dialkylamino group having two $C_1$–$C_6$-alkyl groups (as mentioned above), independent of one another, which is bonded to the skeleton via a thiocarbonyl group (—CS—);

Alkenyl: unsaturated straight-chain or branched hydrocarbon radicals having 2 to 6 or 10 carbon atoms and a double bond in any position, eg. $C_2$–$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

Alkenyloxy: unsaturated straight-chain or branched hydrocarbon radicals having 3 to 6 or 10 carbon atoms and a double bond in any position which is not adjacent to the hetero atom (as mentioned above) which are bonded to the skeleton via an oxygen atom (—O—);

Alkenylcarbonyl: unsaturated straight-chain or branched hydrocarbon radicals having 2 to 10 carbon atoms and a double bond in any position (as mentioned above) which are bonded to the skeleton via a carbonyl group (—CO—);

Alkynyl: straight-chain or branched hydrocarbon groups having 2 to 4, 6, 8 or 10 carbon atoms and a triple bond in any position, eg. $C_2$–$C_6$-alkynyl such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3- dimethyl-1-butynyl, 1-ethyl-2-butynyl, 1-ethyl-3-butynyl, 2-ethyl-3-butynyl and 1-ethyl-1-methyl-2-propynyl;

Alkynyloxy: unsaturated straight-chain or branched hydrocarbon radicals having 3 to 10 carbon atoms and a triple bond in any position which is not adjacent to the hetero atom (as mentioned above) which are bonded to the skeleton via an oxygen atom (—O—);

Alkynylcarbonyl: unsaturated straight-chain or branched hydrocarbon radicals having 2 to 10 carbon atoms and a triple bond in any position (as mentioned above) which are bonded to the skeleton via a carbonyl group (—CO—);

Cycloalkyl: monocyclic saturated hydrocarbon groups having 3 to 6 or 10 carbon ring members, eg. $C_3$–$C_8$-cycloalkyl such as cyclopropyl, cyclobutyl, cyclopentyl, cyclohexyl, cycloheptyl and cyclooctyl;

Cycloalkoxy: monocyclic saturated hydrocarbon groups having 3 to 6 or 10 carbon ring members (as mentioned above) which are bonded to the skeleton via an oxygen atom (—O—);

Cycloalkenyl: monocyclic monounsaturated hydrocarbon groups having 3 to 6 or 10 carbon ring members and a double bond in any position of the ring, eg. $C_5$–$C_8$-cycloalkenyl such as cyclopentenyl, cyclohexenyl, cycloheptenyl and cyclooctenyl;

Heterocyclyl: 5- or 6-membered heterocycles containing, in addition to carbon ring members, one to three nitrogen atoms and/or one oxygen or sulfur atom or one or two oxygen and/or sulfur atoms, eg. 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2,3-pyrrolin-2-yl, 2,3-pyrrolin-3-yl, 2,4-pyrrolin-2-yl, 2,4-pyrrolin-3-yl, 2,3-isoxazolin-3-yl, 3,4-isoxazolin-3-yl, 4,5-isoxazolin-3-yl, 2,3-isoxazolin-4-yl, 3,4-isoxazolin-4-yl, 4,5-isoxazolin-4-yl, 2,3-isoxazolin-5-yl, 3,4-isoxazolin-5-yl, 4,5-isoxazolin-5-yl, 2,3-isothiazolin-3-yl, 3,4-isothiazolin-3-yl, 4,5-isothiazolin-3-yl, 2,3-isothiazolin-4-yl, 3,4-isothiazolin-4-yl, 4,5-isothiazolin-4-yl, 2,3-isothiazolin-5-yl, 3,4-isothiazolin-5-yl, 4,5-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-4-yl, 3,4-dihydrooxazol-3-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl and 1,2,4-tetrahydrotriazin-3-yl;

Heterocyclyloxy: 5- or 6-membered heterocycles (as mentioned above) which are bonded to the skeleton via an oxygen atom (—O—);

Aryl: a mono- to trinuclear aromatic ring system containing 6 to 14 carbon ring members, eg. phenyl, naphthyl and anthracenyl;

Aryloxy: a mono- to trinuclear aromatic ring system (as mentioned above) which is bonded to the skeleton via an oxygen atom (—O—);

Arylthio: a mono- to trinuclear aromatic ring system (as mentioned above) which is bonded to the skeleton via a sulfur atom (—S—);

Arylcarbonyl: a mono- to trinuclear aromatic ring system (as mentioned above) which is bonded to the skeleton via a carbonyl group (—CO—);

Arylsulfonyl: a mono- to trinuclear aromatic ring system (as mentioned above) which is bonded to the skeleton via a sulfonyl group (—$SO_2$—);

Arylsulfoxyl: a mono- to trinuclear aromatic ring system (as mentioned above) which is bonded to the skeleton via a sulfoxyl group (—O—$SO_2$—);

Hetaryl: a mono- or binuclear, 5-, 6-, 9- or 10-membered aromatic ring system which, in addition to carbon ring members, contains hetero atoms selected from the group consisting of oxygen, sulfur and nitrogen: eg.

5-membered hetaryl containing one to four nitrogen atoms or one to three nitrogen atoms and one sulfur or oxygen atom: 5-membered hetaryl ring groups which, in addition to carbon atoms, can contain one to four nitrogen atoms or one to three nitrogen atoms and one sulfur or oxygen atom as ring members, eg. 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

benzo-fused 5-membered hetaryl containing one to three nitrogen atoms or one nitrogen atom and one oxygen or sulfur atom: 5-membered hetaryl ring groups which, in addition to carbon atoms, can contain one to four nitrogen atoms or one to three nitrogen atoms and one sulfur or oxygen atom as ring members and in which two adjacent carbon ring members or a nitrogen and an adjacent carbon ring member can be bridged by a buta-1,3-diene-1,4-diyl group;

5-membered hetaryl, bonded via nitrogen and containing one to four nitrogen atoms, or benzo-fused 5-membered hetaryl, bonded via nitrogen and containing one to three nitrogen atoms: 5-membered hetaryl ring groups which, in addition to carbon atoms, can contain one to four nitrogen atoms, or one to three nitrogen atoms, as ring members and in which two adjacent carbon ring members or a nitrogen and an adjacent carbon ring member can be bridged by a buta-1,3-diene-1,4-diyl group, these rings being bonded to the skeleton via one of the nitrogen ring members;

6-membered hetaryl containing one to three. or one to four, nitrogen atoms: 6-membered hetaryl ring groups which, in addition to carbon atoms, can contain one to three, or one to four, nitrogen atoms as ring members, eg. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

Hetaryloxy: a mono- or binuclear heteroaromatic ring system (as mentioned above) which is bonded to the skeleton via an oxygen atom (—O—);

Hetarylthio: a mono- or binuclear heteroaromatic ring system (as mentioned above) which is bonded to the skeleton via a sulfur atom (—S—);

Hetarylcarbonyl: a mono- or binuclear heteroaromatic ring system (as mentioned above) which is bonded to the skeleton via a carbonyl group (—CO—);

Hetarylsulfonyl: a mono- or binuclear heteroaromatic ring system (as mentioned above) which is bonded to the skeleton via a sulfonyl group (—SO$_2$—).

Hetarylsulfoxyl: a mono- or binuclear heteroaromatic ring system (as mentioned above) which is bonded to the skeleton via a sulfoxyl group (—O—SO$_2$—).

The addition "unsubstituted or substituted" when relating to alkyl, alkenyl and alkynyl groups is intended to express that these groups can be partially or fully halogenated [ie. some or all of the hydrogen atoms of these groups can be replaced by identical or different halogen atoms as mentioned above (preferably fluorine, chlorine or bromine)] and/or can have attached to them one to three (preferably one) of the following radicals:

cyano, nitro, hydroxyl, amino, formyl, carboxyl, aminocarbonyl, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino and alkylcarbonyl-N-alkylamino, the alkyl groups in these radicals preferably containing 1 to 6 carbon atoms, in particular 1 to 4 carbon atoms;

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members and the alkyl groups in these radicals containing preferably 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetarylalkoxy, hetarylalkylthio, hetarylalkylamino and hetarylalkyl-N-alkylamino, unsubstituted or substituted by customary groups, the aryl radicals preferably containing 6 to 10 ring members, in particular 6 ring members (phenyl), the hetaryl radicals containing in particular 5 or 6 ring members and the alkyl groups in these radicals containing preferably 1 to 6 carbon atoms, in particular 1 to 4 carbon atoms.

The addition "unsubstituted or substituted" when relating to the cyclic (saturated, unsaturated or aromatic) groups is intended to express that these groups can be partially or fully halogenated [ie. some or all of the hydrogen atoms of these groups can be replaced by identical or different halogen atoms as mentioned above (preferably fluorine, chlorine or bromine, in particular fluorine or chlorine)] and/or can have attached to them one to four (in particular one to three) of the following radicals:

cyano, nitro, hydroxyl, amino, carboxyl, aminocarbonyl, alkyl, haloalkyl, alkenyl, haloalkenyl, alkenyloxy, haloalkenyloxy, alkynyl, haloalkynyl, alkynyloxy, haloalkynyloxy, alkoxy, haloalkoxy, alkylthio, haloalkylthio, alkylamino, dialkylamino, alkylcarbonyl, alkoxycarbonyl, alkylcarbonyloxy, alkylaminocarbonyl, dialkylaminocarbonyl, alkylcarbonylamino, alkoxycarbonylamino and alkylcarbonyl-N-alkylamino, the alkyl groups in these radicals preferably containing 1 to 6 carbon atoms, in particular 1 to 4 carbon atoms and the alkenyl or alkynyl groups mentioned in these radicals containing 2 to 8, preferably 2 to 6, in particular 2 to 4 carbon atoms;

and/or one to three (in particular one) of the following radicals:

cycloalkyl, cycloalkoxy, cycloalkylthio, cycloalkylamino, cycloalkyl-N-alkylamino, heterocyclyl, heterocyclyloxy, heterocyclylthio, heterocyclylamino or heterocyclyl-N-alkylamino, unsubstituted or substituted by customary groups, the cyclic systems containing 3 to 12 ring members, preferably 2 to 8 ring members, in particular 3 to 6 ring members and the alkyl groups in these radicals containing preferably 1 to 6 carbon atoms, in particular 1 to 4 carbon atoms;

aryl, aryloxy, arylthio, arylamino, aryl-N-alkylamino, arylalkoxy, arylalkylthio, arylalkylamino, arylalkyl-N-alkylamino, hetaryl, hetaryloxy, hetarylthio, hetarylamino, hetaryl-N-alkylamino, hetarylalkoxy, hetarylalkylthio, hetarylalkylamino and hetarylalkyl-N-alkylamino, unsubstituted or substituted by customary groups, the aryl radicals containing preferably 6 to 10 ring members, in particular 6 ring members (phenyl), the hetaryl radicals containing in particular 5 or 6 ring members and the alkyl groups in these radicals containing preferably 1 to 6 carbon atoms, in particular 1 to 4 carbon atoms, and/or one or two (in particular one) of the following radicals:

formyl,

CR$^v$=NOR$^{vi}$ [where R$^v$ is hydrogen, alkyl, cycloalkyl and aryl and R$^{vi}$ is alkyl, alkenyl, haloalkenyl, alkynyl and arylalkyl (the alkyl groups mentioned preferably containing 1 to 6 carbon atoms, in particular 1 to 4 carbon atoms, and the cycloalkyl groups, alkenyl groups and alkynyl groups mentioned preferably containing 3 to 8, in particular 3 to 6, carbon atoms) and aryl, in particular phenyl, which is unsubstituted or which can be substituted by customary groups] or NR$^{vii}$-CO-D-R$^{viii}$ [where R$^{vii}$ is hydrogen, hydroxyl, C$_1$–C$_6$-alkyl, C$_2$–C$_6$-alkenyl, C$_2$–C$_6$-alkynyl, C$_1$–C$_6$-alkoxy, C$_2$–C$_6$-alkenyloxy, C$_2$–C$_6$-alkynyloxy, C$_1$–C$_6$-alkoxy-C$_1$–C$_6$-alkyl, C$_1$–C$_6$-alkoxy-C$_1$–C$_6$-alkoxy and C$_1$–C$_6$-alkoxycarbonyl, R$^{viii}$ is hydrogen, C$_1$–C$_6$-alkyl, C$_2$–C$_6$-alkenyl, C$_2$–C$_6$-alkynyl, C$_3$–C$_6$-cycloalkyl, C$_3$–C$_6$-cycloalkenyl, aryl, aryl-C$_1$–C$_6$-alkyl, hetaryl and hetaryl-C$_1$–C$_6$-alkyl and D is a direct bond, oxygen or nitrogen, it being possible for the nitrogen to have attached to it one of the groups mentioned for R$^{vi}$], and/or where two adjacent C atoms of the cyclic systems can have attached to them a C$_3$–C$_5$-alkylene, C$_3$–C$_5$-alkenylene, oxy-C$_2$–C$_4$-alkylene, oxy-C$_1$–C$_3$-alkyleneoxy, oxy-C$_2$–C$_4$-alkenylene, oxy-C$_2$–C$_4$-alkenyleneoxy or butadienediyl group, it being possible for these bridges, in turn, to be partially or fully halogenated and/or to have attached to them one to three, in particular one or two, of the following radicals:

C$_1$–C$_4$-alkyl, C$_1$–C$_4$-haloalkyl, C$_1$–C$_4$-alkoxy, C$_1$–C$_4$-haloalkoxy and C$_1$–C$_4$-alkylthio.

Customary groups are to be understood as meaning, in particular, the following substituents: cyano, nitro, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylamino, di-$C_1$–$C_4$-alkylamino and $C_1$–$C_4$-alkylthio.

Preferred compounds of the formula I with a view to their biological activities are those where $R^2$ has the following meanings:

alkyl, alkenyl, alkynyl, alkoxy, alkenyloxy or alkynyloxy, it being possible for the hydrocarbon groups, in turn, to be partially or fully halogenated and/or to have attached to them one to three of the following radicals:

cyano, nitro, hydroxyl, mercapto, amino, carboxyl, aminocarbonyl, amino thiocarbonyl, $C_1$–$C_6$-alkylsulfonyl, $C_1$–$C_6$-alkylsulfoxyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylaminocarbonyl, $C_1$–$C_6$-alkylaminorothicaboyl di-$C_1$–$C_6$-alkylaminothiocarbonyl, $C_2$–$C_6$-alkenyloxy, benzyloxy, aryl, aryloxy, hetaryl and hetaryloxy, it being possible for the aromatic rings to be substituted by customary groups;

cycloalkyl, cycloalkoxy, heterocyclyl or heterocyclyloxy, it being possible for the cyclic groups, in turn, to be partially or fully halogenated and/or to have attached to them one to three of the following radicals:

cyano, nitro, hydroxyl, mercapto, amino, carboxyl, aminocarbonyl, amino thiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl and hetaryloxy, it being possible for the aromatic rings to be substituted by customary groups;

aryl, hetaryl, aryloxy or hetaryloxy, it being possible for the cyclic groups, in turn, to be partially or fully halogenated and/or to have attached to them one to three of the following radicals:

cyano, nitro, hydroxyl, mercapto, amino, carboxyl, aminocarbonyl, aminothiocarbonyl, $C_1$–$C_6$-alkyl, $C_1$–$C_6$-haloalkyl, $C_1$–$C_6$-alkylsulfonyl, $C_1$–$C_6$-alkylsulfoxyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyl, $C_2$–$C_6$-alkenyloxy, benzyl, benzyloxy, aryl, aryloxy, hetaryl, hetaryloxy, it being possible for the aromatic rings to be substituted by customary groups, $C(=NOR^i)$—$A_m$—$R^{ii}$ or $NR^{iii}$—CO—D—$R^{iv}$;

A is oxygen, sulfur or nitrogen, the nitrogen having attached to it hydrogen or $C_1$–$C_6$-alkyl;
m is 0 or 1;
$R^i$ is hydrogen, $C_1$–$C_6$-alkyl, $C_3$–$C_6$-alkenyl or $C_3$–$C_6$-alkynyl;
$R^{ii}$ is hydrogen or $C_1$–$C_6$-alkyl;

D is a direct bond, oxygen or $NR^b$ ($R^b$=hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl);

$R^{iii}$ is hydrogen, hydroxyl, $C_1$–$C_6$-alkyl, $C_2$–$C_6$-alkenyl, $C_2$–$C_6$-alkynyl, $C_1$–$C_6$-alkoxy, $C_2$–$C_6$-alkenyloxy, $C_2$–$C_6$-alkynyloxy, $C_1$–$C_6$-alkoxy-$C_1$–$C_6$-alkyl, $C_1$–$C_6$-alkoxy-$C_1$–$C_6$-alkoxy and $C_1$–$C_6$-alkoxycarbonyl;

$R^{iv}$ is hydrogen, $C_1$–$C_6$-alkyl, $C_2$–$C_6$-alkenyl, $C_2$–$C_6$-alkynyl, $C_3$–$C_6$-cycloalkyl, $C_3$–$C_6$-cycloalkenyl, aryl, aryl-$C_1$–$C_6$-alkyl, hetaryl and hetaryl-$C_1$–$C_6$-alkyl.

Especially preferred pyridine derivatives of the formula I are those where the substituents have the following meanings:

$R^1$ is hydrogen, cyano,
$C_1$–$C_6$-alkyl, $C_1$–$C_6$-haloalkyl, $C_3$–$C_6$-cycloalkyl, $C_3$–$C_6$-cycloalkyl-$C_1$–$C_4$-alkyl,
aryl, aryl-$C_1$–$C_4$-alkyl and aryloxy-$C_1$–$C_4$-alkyl, it being possible for the aromatic rings to be partially or fully halogenated and/or to have attached to them one to three of the following radicals: cyano, nitro, $C_1$–$C_6$-alkyl, $C_1$–$C_6$-haloalkyl, $C_1$–$C_6$-alkoxy, $C_1$–$C_6$-haloalkoxy, and $C(CH_3)=N$—$A^1$—$R^a$;

$R^2$ is unsubstituted or substituted aryl, hetaryl, aryloxy, hetaryloxy, arylthio and hetarylthio;
—Q—C($R^3$)=N—$Y^1$—$R^4$ or —Q—O—N=$CR^5R^6$, $R^1$ and $R^2$ together with the carbon atom to which they are bonded are a four- to eight-membered ring which, in addition to carbon atoms, can contain one or two oxygen and/or sulfur atoms and/or NH and/or N($C_1$–$C_4$-alkyl) groups and whose carbon atoms can have attached to them one of the following substituents: halogen, $C_1$–$C_6$-alkyl or $C_1$–$C_4$-alkoxyimino, where $R^1$ and $R^2$ are not simultaneously bonded to the carbon atoms via hetero atoms.

Moreover, preferred pyridine derivatives of the formula I are those where the substituents have the following meanings:

$R^1$ is hydrogen, cyano, halogen,
$C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_3$–$C_6$-cycloalkyl, $C_3$–$C_6$-cycloalkyl-$C_1$–$C_4$-alkyl,
aryl, aryl-$C_1$–$C_4$-alkyl, aryloxy-$C_1$–$C_4$-alkyl and aryl-$C_1$–$C_4$-alkoxy, it being possible for the aromatic rings to be partially or fully halogenated and/or to have attached to them one to three of the following radicals: cyano, nitro, $C_1$–$C_6$-alkyl, $C_1$–$C_6$-haloalkyl, $C_1$–$C_6$-alkoxy, $C_1$–$C_6$-haloalkoxy, and $C(CH_3)=N$—$A^1$—$R^a$;

$R^2$ is unsubstituted or substituted aryl and hetaryl;
—Q—C($R^3$)=N—$Y^1$—$R^4$ or —Q—O—N=$CR^5R^6$, $R^1$ and $R^2$ are not simultaneously bonded to the carbon atom via hetero atoms.

Especially preferred with a view to biological efficacy are compounds I where the radical R and the group —Y—N=$CR^1R^2$ are bonded to adjacent C atoms of the pyridyl ring.

Moreover, especially preferred compounds I are those where n is 0 or 1.

In the event that n is 1, preferred compounds I are those where X is cyano, halogen (in particular fluorine and chlorine), $C_1$–$C_3$-alkyl (in particular methyl and ethyl), $C_1$–$C_2$-haloalkyl (in particular difluoromethyl and trifluoromethyl), $C_1$–$C_3$-alkoxy (in particular methoxy), $C_1$–$C_2$-haloalkoxy (in particular difluoromethoxy and trifluoromethoxy) or cyclopropyl.

Moreover, especially preferred compounds I are those where Y is oxygen.

In the event that Y is nitrogen, preferred compounds I are those where the nitrogen atom additionally has attached to it a hydrogen atom or a $C_1$–$C_3$-alkyl group (in particular methyl, ethyl or isopropyl).

Additionally preferred compounds I are those where R is $C(CO_2CH_3)\!=\!CHCH_3$, $C(CO_2CH_3)\!=\!CHOCH_3$, $C(CO_2CH_3)\!=\!NOCH_3$ or $C(CONHCH_3)\!=\!NOCH_3$.

The following compounds Ia.1–Id.4 are particularly preferred.

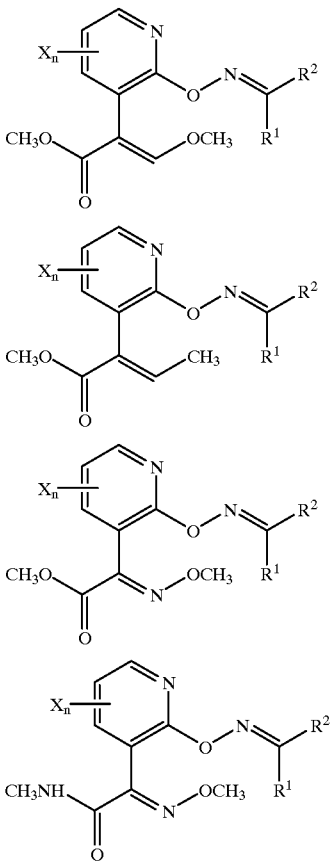

Particularly preferred with a view to use against animal pests and harmful fungi are compounds of the formula I.4

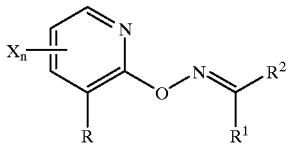

(I.4)

where substituents and the index have the following meanings:

R is $C(CO_2CH_3)=CHCH_3$, $C(CO_2CH_3)=CHOCH_3$, $C(CO_2CH_3)=NOCH_3$ or $C(CONHCH_3)=NOCH_3$;

X is cyano, halogen, $C_1-C_4$-alkyl, $C_1-C_2$-haloalkyl, $C_1-C_4$-alkoxy, $C_1-C_2$-haloalkoxy and $C_3-C_6$-cycloalkyl;

n is 0 or 1;

$R^1$ is hydrogen, hydroxyl, cyano, $C_1-C_4$-alkyl, $C_1-C_2$-haloalkyl, $C_1-C_4$-alkoxy, $C_1-C_2$-haloalkoxy, $C_3-C_6$-cycloalkyl, $C_3-C_6$-cycloalkyl-$C_1-C_4$-alkyl, or benzyl which can be substituted by customary groups;

$R^2$ is hydrogen, $C_3-C_6$-cycloalkyl, $C_1-C_6$-alkyl or $C_1-C_6$-alkoxy which can be partially or fully halogenated and/or can have attached to it one to three (in particular one) of the following groups: cyano, $C_1-C_4$-alkoxy, $C_3-C_6$-cycloalkyl, or phenyl, naphthyl, pyridinyl, pyrazinyl, thienyl, pyrazolyl or isoxazolyl, in each case unsubstituted or substituted by customary groups;

phenyl, naphthyl, pyridinyl, pyrazinyl, thienyl, pyrazolyl or isoxazolyl, unsubstituted or substituted by customary groups;

phenoxy, naphthyloxy, pyridinyloxy, pyrazinyloxy, thienyloxy, pyrazolyloxy or isoxazolyloxy, unsubstituted or substituted by customary groups; or $R^1$ and $R^2$ together with the carbon atom to which they are bonded are a saturated or partially unsaturated, four- to eight-membered ring which, in addition to hydrocarbon ring members, can contain a hetero atom selected from the group consisting of oxygen, sulfur and nitrogen and which can be partially halogenated and/or can have attached to it one to three of the following groups: $C_1-C_4$-alkyl, $C_1-C_4$-haloalkyl, $C_1-C_4$-alkoxy, $C_1-C_4$-haloalkoxy, oxo (=O) and $C_1-C_4$-alkoxyimino (=N-alkoxy), where $R^1$ and $R^2$ are not simultaneously bonded to the carbon atom via hetero atoms;

Moreover, particularly preferred with a view to use against animal pests and harmful fungi are compounds of the formula I.8

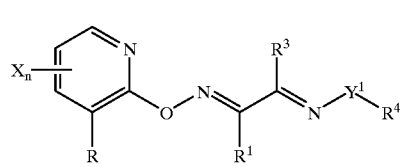

(I.8)

where the substituents and the index have the following meanings:

R is $C(CO_2CH_3)=CHCH_3$, $C(CO_2CH_3)=CHOCH_3$, $C(CO_2CH_3)=NOCH_3$ or $C(CONHCH_3)=NOCH_3$;

X is cyano, halogen, $C_1-C_4$-alkyl, $C_1-C_2$-haloalkyl, $C_1-C_4$-alkoxy, $C_1-C_2$-haloalkoxy and $C_3-C_6$-cycloalkyl;

n is 0 or 1;

$R^1$ is hydrogen, cyano, halogen, $C_1-C_4$-alkyl, $C_1-C_2$-haloalkyl, $C_1-C_4$-alkoxy, $C_1-C_2$-haloalkoxy and $C_3-C_6$-cycloalkyl;

$R^3$ is hydrogen, cyano, halogen, $C_1-C_4$-alkyl, $C_1-C_2$-haloalkyl, $C_1-C_4$-alkoxy, $C_1-C_2$-haloalkoxy and $C_3-C_6$-cycloalkyl;

$Y^1$ is O, NH or $N(CH_3)$;

$R^4$ is hydrogen, $C_1-C_6$-alkyl which can have attached to it one of the following groups: $C_1-C_4$-alkoxy, $C_3-C_6$-cycloalkyl, unsubstituted or substituted by customary groups, or phenyl, unsubstituted or substituted by customary groups;

$C_3-C_6$-alkenyl, $C_3-C_6$-haloalkenyl, $C_3-C_6$-alkynyl, $C_3-C_6$-haloalkynyl, or $C_3-C_6$-cycloalkyl, unsubstituted or substituted by customary groups.

Furthermore, particularly preferred with a view to use against animal pests and harmful fungi are compounds of the formula I.12

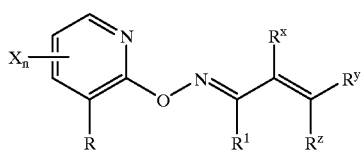
(I.12)

where the substituents and the index have the following meanings:

R is $C(CO_2CH_3)=CHCH_3$, $C(CO_2CH_3)=CHOCH_3$, $C(CO_2CH_3)=NOCH_3$ or $C(CONHCH_3)=NOCH_3$;

X is cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

n is 0 or 1;

$R^1$ is hydrogen, cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

$R^x$ is hydrogen, cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

$R^y$ is hydrogen,
  $C_1$–$C_6$-alkyl which can be partially or fully halogenated and/or can have attached to it one to three (in particular one) of the following groups: $C_1$–$C_4$-alkoxy, $C_3$–$C_6$-cycloalkyl, unsubstituted or substituted by customary groups, or phenyl, unsubstituted or substituted by customary groups;
  $C_1$–$C_6$-alkoxy, $C_1$–$C_6$-haloalkoxy,
  $C_3$–$C_6$-cycloalkyl, unsubstituted or substituted by customary groups; phenyl, unsubstituted or substituted by customary groups, pyridyl, unsubstituted or substituted by customary groups, or pyrimidyl, unsubstituted or substituted by customary groups;

$R^z$ is hydrogen, cyano, halogen, $C_1$–$C_4$-alkyl, $C_1$–$C_2$-haloalkyl and $C_3$–$C_6$-cycloalkyl, or $R^y$ and $R^x$ together with the double bond to which they are bonded are $C_4$–$C_6$-cycloalkenyl.

Particularly preferred with a view to their use are the compounds I compiled in the tables which follow. Moreover, the groups mentioned in the tables for a substituent are, in their own right and independent of the combination in which they are mentioned, an especially preferred embodiment of the substituent in question.

Table 1

Compounds of the formula Ia.1 where $X_n$ is hydrogen and the combination of the radicals $R^1$ and $R^2$ for each compound corresponds to one line of Table A

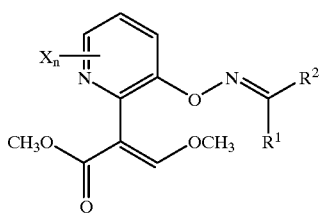
(Ia.1)

Table 2

Compounds of the formula Ia.2 where $X_n$ is hydrogen and the combination of the radicals $R^1$ and $R^2$ for each compound corresponds to one line of Table A

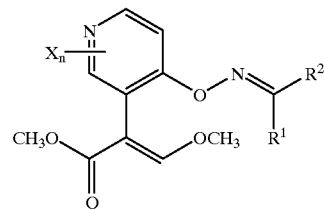
(Ia.2)

Table 3

Compounds of the formula Ia.3 where $X_n$ is hydrogen and the combination of the radicals $R^1$ and $R^2$ for each compound corresponds to one line of Table A

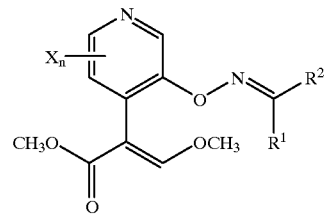
(Ia.3)

Table 4

Compounds of the formula Ia.4 where $X_n$ is hydrogen and the combination of the radicals $R^1$ and $R^2$ for each compound corresponds to one line of Table A

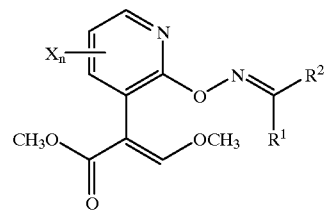
(Ia.4)

Table 5

Compounds of the formula Ia.4 where $X_n$ is 6-$CF_3$ and the combination of the radicals $R^1$ and $R^2$ for each compound corresponds to one line of Table A Table 6

Compounds of the formula Ia.4 where $X_n$ is 6-$CH(CH_3)_2$ and the combination of the radicals $R^1$ and $R^2$ for each compound corresponds to one line of Table A Table 7

Compounds of the formula Ib.1 where $X_n$ is hydrogen and the combination of the radicals $R^1$ and $R^2$ for each compound corresponds to one line of Table A (Ib.1)

Table 8
Compounds of the formula Ib.2 where $X_n$ is hydrogen and the combination of the radicals $R^1$ and $R^2$ for each compound corresponds to one line of Table A (Ib.2)

Table 9
Compounds of the formula Ib.3 where $X_n$ is hydrogen and the combination of the radicals $R^1$ and $R^2$ for each compound corresponds to one line of Table A (Ib.3)

Table 10
Compounds of the formula Ib.4 where $X_n$ is hydrogen and the comination of the radicals $R^1$ and $R^2$ for each compound corresponds to one line of Table A (Ib.4)

Table 11
Compounds of the formula Ib.4 where $X_n$ is 6-$CF_3$ and the combination of the radicals $R^1$ and $R^2$ for each compound corresponds to one line of Table A

Table 12
Compounds of the formula Ib.4 where $X_n$ is 6-$CH(CH_3)_2$ and the combination of the radicals $R^1$ and $R^2$ for each compound corresponds to one line of Table A

Table 13
Compounds of the formula Ic.1 where $X_n$ is hydrogen and the combination of the radicals $R^1$ and $R^2$ for each compound corresponds to one line of Table A (Ic.1)

Table 14
Compounds of the formula Ic.2 where $X_n$ is hydrogen and the combination of the radicals $R^1$ and $R^2$ for each compound corresponds to one line of Table A (Ic.2)

Table 15
Compounds of the formula Ic.3 where $X_n$ is hydrogen and the combination of the radicals $R^1$ and $R^2$ for each compound corresponds to one line of Table A (Ic.3)

Table 16
Compounds of the formula Ic.4 where $X_n$ is hydrogen and the combination of the radicals $R^1$ and $R^2$ for each compound corresponds to one line of Table A (Ic.4)

Table 17
Compounds of the formula Ic.4 where $X_n$ is 6-$CF_3$ and the combination of the radicals $R^1$ and $R^2$ for each compound corresponds to one line of Table A Table 18

Compounds of the formula Ic.4 where $X_n$ is 6-CH(CH$_3$)$_2$ and the combination of the radicals R$^1$ and R$^2$ for each compound corresponds to one line of Table A Table 19

Compounds of the formula Id.1 where $X_n$ is hydrogen and the combination of the radicals R$^1$ and R$^2$ for each compound corresponds to one line of Table A

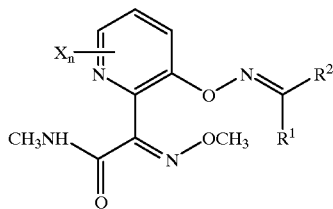
(Id.1)

Table 20

Compounds of the formula Id.2 where $X_n$ is hydrogen and the combination of the radicals R$^1$ and R$^2$ for each compound corresponds to one line of Table A

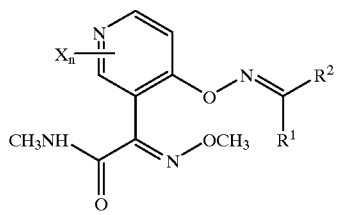
(Id.2)

Table 21

Compounds of the formula Id.3 where $X_n$ is hydrogen and the combination of the radicals R$^1$ and R$^2$ for each compound corresponds to one line of Table A

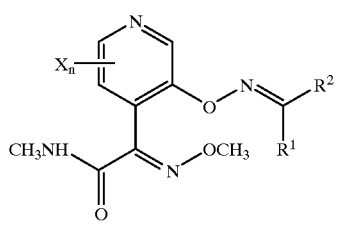
(Id.3)

Table 22

Compounds of the formula Id.4 where $X_n$ is hydrogen and the combination of the radicals R$^1$ and R$^2$ for each compound corresponds to one line of Table A

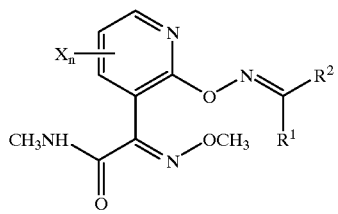
(Id.4)

Table 23

Compounds of the formula Id.4 where $X_n$ is 6-CF$_3$ and the combination of the radicals R$^1$ and R$^2$ for each compound corresponds to one line of Table A Table 24

Compounds of the formula Id.4 where $X_n$ is 6-CH(CH$_3$)$_2$ and the combination of the radicals R$^1$ and R$^2$ for each compound corresponds to one line of Table A Table 25

Compounds of the formula Ia.5 where $X_n$ is hydrogen, Y$^1$ is oxygen and the combination of the radicals R$^1$, R$^3$ and R$^4$ for each compound corresponds to one line of Table B

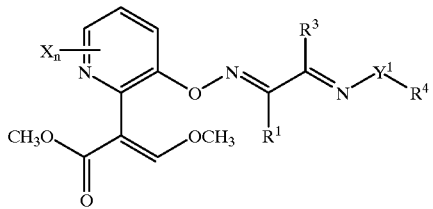
(Ia.5)

Table 26

Compounds of the formula Ia.5 where $X_n$ is hydrogen, Y$^1$ is NH and the combination of the radicals R$^1$, R$^3$ and R$^4$ for each compound corresponds to one line of Table B Table 27

Compounds of the formula Ia.5 where $X_n$ is hydrogen, Y$^1$ is NCH$_3$ and the combination of the radicals R$^1$, R$^3$ and R$^4$ for each compound corresponds to one line of Table B Table 28

Compounds of the formula Ia.6 where $X_n$ is hydrogen, Y$^1$ is oxygen and the combination of the radicals R$^1$, R$^3$ and R$^4$ for each compound corresponds to one line of Table B

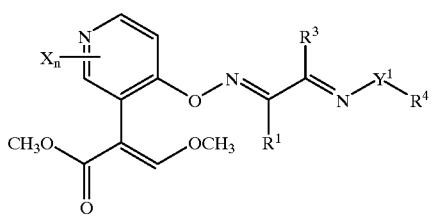
(Ia.6)

Table 29

Compounds of the formula Ia.6 where $X_n$ is hydrogen, Y$^1$ is NH and the combination of the radicals R$^1$, R$^3$ and R$^4$ for each compound corresponds to one line of Table B Table 30

Compounds of the formula Ia.6 where $X_n$ is hydrogen, Y$^1$ is NCH$_3$ and the combination of the radicals R$^1$, R$^3$ and R$^4$ for each compound corresponds to one line of Table B Table 31

Compounds of the formula Ia.7 where $X_n$ is hydrogen, Y$^1$ is oxygen and the combination of the radicals R$^1$, R$^3$ and R$^4$ for each compound corresponds to one line of Table B (Ia.7)

Table 32
Compounds of the formula Ia.7 where $X_n$ is hydrogen, $Y^1$ is NH and the combination of the radicals $R^1$, $R^3$ and $R^4$ for each compound corresponds to one line of Table B

Table 33
Compounds of the formula Ia.7 where $X_n$ is hydrogen, $Y^1$ is $NCH_3$ and the combination of the radicals $R^1$, $R^3$ and $R^4$ for each compound corresponds to one line of Table B

Table 34
Compounds of the formula Ia.8 where $X_n$ is hydrogen, $Y^1$ is oxygen and the combination of the radicals $R^1$, $R^3$ and $R^4$ for each compound corresponds to one line of Table B (Ia.8)

Table 35
Compounds of the formula Ia.8 where $X_n$ is hydrogen, $Y^1$ is NH and the combination of the radicals $R^1$, $R^3$ and $R^4$ for each compound corresponds to one line of Table B

Table 36
Compounds of the formula Ia.8 where $X_n$ is hydrogen, $Y^1$ is $NCH_3$ and the combination of the radicals $R^1$, $R^3$ and $R^4$ for each compound corresponds to one line of Table B

Table 37
Compounds of the formula Ia.8 where $X_n$ is $6\text{-}CF_3$, $Y^1$ is oxygen and the combination of the radicals $R^1$, $R^x$, $R^y$ and $R^z$ for each compound corresponds to one line of Table C

Table 38
Compounds of the formula Ia.8 where $X_n$ is $6\text{-}CH(CH_3)_2$, $Y^1$ is oxygen and the combination of the radicals $R^1$, $R^3$ and $R^4$ for each compound corresponds to one line of Table B

Table 39
Compounds of the formula Ia.8 where $X_n$ is $6\text{-}CF_3$, $Y^1$ is NH and the combination of the radicals $R^1$, $R^3$ and $R^4$ for each compound corresponds to one line of Table B

Table 40
Compounds of the formula Ia.8 where $X_n$ is $6\text{-}CH(CH_3)_2$, $Y^1$ is NH and the combination of the radicals $R^1$, $R^3$ and $R^4$ for each compound corresponds to one line of Table B

Table 41
Compounds of the formula Ia.8 where $X_n$ is $6\text{-}CF_3$, $Y^1$ is $NCH_3$ and the combination of the radicals $R^1$, $R^3$ and $R^4$ for each compound corresponds to one line of Table B

Table 42
Compounds of the formula Ia.8 where $X_n$ is $6\text{-}CH(CH_3)_2$, $Y^1$ is $NCH_3$ and the combination of the radicals $R^1$, $R^3$ and $R^4$ for each compound corresponds to one line of Table B

Table 43
Compounds of the formula Ib.5 where $X_n$ is hydrogen, $Y^1$ is oxygen and the combination of the radicals $R^1$, $R^3$ and $R^4$ for each compound corresponds to one line of Table B (Ib.5)

Table 44
Compounds of the formula Ib.5 where $X_n$ is hydrogen, $Y^1$ is NH and the combination of the radicals $R^1$, $R^3$ and $R^4$ for each compound corresponds to one line of Table B

Table 45
Compounds of the formula Ib.5 where $X_n$ is hydrogen, $Y^1$ is $NCH_3$ and the combination of the radicals $R^1$, $R^3$ and $R^4$ for each compound corresponds to one line of Table B

Table 46
Compounds of the formula Ib.6 where $X_n$ is hydrogen, $Y^1$ is oxygen and the combination of the radicals $R^1$, $R^3$ and $R^4$ for each compound corresponds to one line of Table B (Ib.6)

Table 47
Compounds of the formula Ib.6 where $X_n$ is hydrogen, $Y^1$ is NH and the combination of the radicals $R^1$, $R^3$ and $R^4$ for each compound corresponds to one line of Table B

Table 48
Compounds of the formula Ib.6 where $X_n$ is hydrogen, $Y^1$ is $NCH_3$ and the combination of the radicals $R^1$, $R^3$ and $R^4$ for each compound corresponds to one line of Table B

Table 49
Compounds of the formula Ib.7 where $X_n$ is hydrogen, $Y^1$ is oxygen and the combination of the radicals $R^1$, $R^3$ and $R^4$ for each compound corresponds to one line of Table B (Ib.7)

Table 50
Compounds of the formula Ib.7 where $X_n$ is hydrogen, $Y^1$ is NH and the combination of the radicals $R^1$, $R^3$ and $R^4$ for each compound corresponds to one line of Table B

Table 51
Compounds of the formula Ib.7 where $X_n$ is hydrogen, $Y^1$ is $NCH_3$ and the combination of the radicals $R^1$, $R^3$ and $R^4$ for each compound corresponds to one line of Table B

Table 52
Compounds of the formula Ib.8 where $X_n$ is hydrogen, $Y^1$ is oxygen and the combination of the radicals $R^1$, $R^3$ and $R^4$ for each compound corresponds to one line of Table B

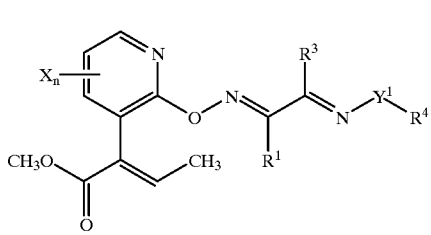
(Ib.8)

Table 53
Compounds of the formula Ib.8 where $X_n$ is hydrogen, $Y^1$ is NH and the combination of the radicals $R^1$, $R^3$ and $R^4$ for each compound corresponds to one line of Table B

Table 54
Compounds of the formula Ib.8 where $X_n$ is hydrogen, $Y^1$ is $NCH_3$ and the combination of the radicals $R^1$, $R^3$ and $R^4$ for each compound corresponds to one line of Table B

Table 55
Compounds of the formula Ib.8 where $X_n$ is 6-$CF_3$, $Y^1$ is oxygen and the combination of the radicals $R^1$, $R^3$ and $R^4$ for each compound corresponds to one line of Table B

Table 56
Compounds of the formula Ib.8 where $X_n$ is 6-$CH(CH_3)_2$, $Y^1$ is oxygen and the combination of the radicals $R^1$, $R^3$ and $R^4$ for each compound corresponds to one line of Table B

Table 57
Compounds of the formula Ib.8 where $X_n$ is 6-$CF_3$, $Y^1$ is NH and the combination of the radicals $R^1$, $R^3$ and $R^4$ for each compound corresponds to one line of Table B

Table 58
Compounds of the formula Ib.8 where $X_n$ is 6-$CH(CH_3)_2$, $Y^1$ is NH and the combination of the radicals $R^1$, $R^3$ and $R^4$ for each compound corresponds to one line of Table B

Table 59
Compounds of the formula Ib.8 where $X_n$ is 6-$CF_3$, $Y^1$ is $NCH_3$ and the combination of the radicals $R^1$, $R^3$ and $R^4$ for each compound corresponds to one line of Table B

Table 60
Compounds of the formula Ib.8 where $X_n$ is 6-$CH(CH_3)_2$, $Y^1$ is $NCH_3$ and the combination of the radicals $R^1$, $R^3$ and $R^4$ for each compound corresponds to one line of Table B

Table 61
Compounds of the formula Ic.5 where $X_n$ is hydrogen, $Y^1$ is oxygen and the combination of the radicals $R^1$, $R^3$ and $R^4$ for each compound corresponds to one line of Table B

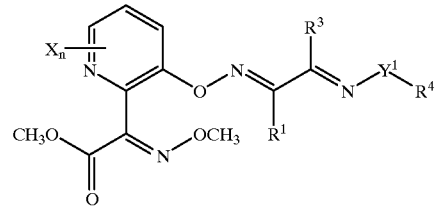
(Ic.5)

Table 62
Compounds of the formula Ic.5 where $X_n$ is hydrogen, $Y^1$ is NH and the combination of the radicals $R^1$, $R^3$ and $R^4$ for each compound corresponds to one line of Table B

Table 63
Compounds of the formula Ic.5 where $X_n$ is hydrogen, $Y^1$ is $NCH_3$ and the combination of the radicals $R^1$, $R^3$ and $R^4$ for each compound corresponds to one line of Table B

Table 64
Compounds of the formula Ic.6 where $X_n$ is hydrogen, $Y^1$ is oxygen and the combination of the radicals $R^1$, $R^3$ and $R^4$ for each compound corresponds to one line of Table B

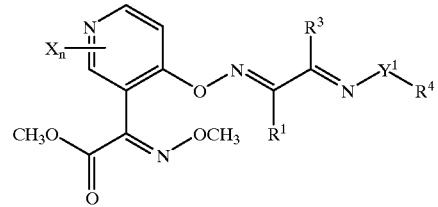
(Ic.6)

Table 65
Compounds of the formula Ic.6 where $X_n$ is hydrogen, $Y^1$ is NH and the combination of the radicals $R^1$, $R^3$ and $R^4$ for each compound corresponds to one line of Table B

Table 66
Compounds of the formula Ic.6 where $X_n$ is hydrogen, $Y^1$ is $NCH_3$ and the combination of the radicals $R^1$, $R^3$ and $R^4$ for each compound corresponds to one line of Table B

Table 67
Compounds of the formula Ic.7 where $X_n$ is hydrogen, $Y^1$ is oxygen and the combination of the radicals $R^1$, $R^3$ and $R^4$ for each compound corresponds to one line of Table B

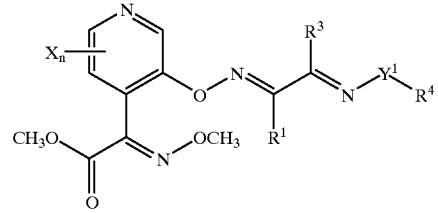
(Ic.7)

Table 68
Compounds of the formula Ic.7 where $X_n$ is hydrogen, $Y^1$ is NH and the combination of the radicals $R^1$, $R^3$ and $R^4$ for each compound corresponds to one line of Table B

Table 69
Compounds of the formula Ic.7 where $X_n$ is hydrogen, $Y^1$ is $NCH_3$ and the combination of the radicals $R^1$, $R^3$ and $R^4$ for each compound corresponds to one line of Table B Table 70
Compounds of the formula Ic.8 where $X_n$ is hydrogen, $Y^1$ is oxygen and the combination of the radicals $R^1$, $R^3$ and $R^4$ for each compound corresponds to one line of Table B

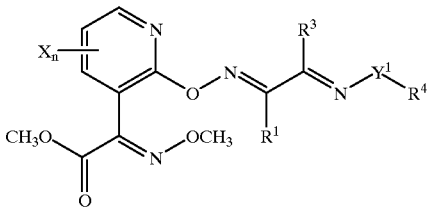

(Ic.8)

Table 71
Compounds of the formula Ic.8 where $X_n$ is hydrogen, $Y^1$ is NH and the combination of the radicals $R^1$, $R^3$ and $R^4$ for each compound corresponds to one line of Table B Table 72
Compounds of the formula Ic.8 where $X_n$ is hydrogen, $Y^1$ is $NCH_3$ and the combination of the radicals $R^1$, $R^3$ and $R^4$ for each compound corresponds to one line of Table B Table 73
Compounds of the formula Ic.8 where $X_n$ is 6-$CF_3$, $Y^1$ is oxygen and the combination of the radicals $R^1$, $R^3$ and $R^4$ for each compound corresponds to one line of Table B Table 74
Compounds of the formula Ic.8 where $X_n$ is 6-$CH(CH_3)_2$, $Y^1$ is oxygen and the combination of the radicals $R^1$, $R^3$ and $R^4$ for each compound corresponds to one line of Table B Table 75
Compounds of the formula Ic.8 where $X_n$ is 6-$CF_3$, $Y^1$ is NH and the combination of the radicals $R^1$, $R^3$ and $R^4$ for each compound corresponds to one line of Table B Table 76
Compounds of the formula Ic.8 where $X_n$ is 6-$CH(CH_3)_2$, $Y^1$ is NH and the combination of the radicals $R^1$, $R^3$ and $R^4$ for each compound corresponds to one line of Table B Table 77
Compounds of the formula Ic.8 where $X_n$ is 6-$CF_3$, $Y^1$ is $NCH_3$ and the combination of the radicals $R^1$, $R^3$ and $R^4$ for each compound corresponds to one line of Table B Table 78
Compounds of the formula Ic.8 where $X_n$ is 6-$CH(CH_3)_2$, $Y^1$ is $NCH_3$ and the combination of the radicals $R^1$, $R^3$ and $R^4$ for each compound corresponds to one line of Table B Table 79
Compounds of the formula Id.5 where $X_n$ is hydrogen, $Y^1$ is oxygen and the combination of the radicals $R^1$, $R^3$ and $R^4$ for each compound corresponds to one line of Table B

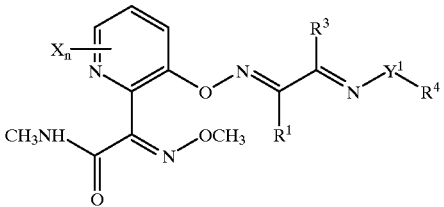

(Id.5)

Table 80
Compounds of the formula Id.5 where $X_n$ is hydrogen, $Y^1$ is NH and the combination of the radicals $R^1$, $R^3$ and $R^4$ for each compound corresponds to one line of Table B Table 81
Compounds of the formula Id.5 where $X_n$ is hydrogen, $Y^1$ is $NCH_3$ and the combination of the radicals $R^1$, $R^3$ and $R^4$ for each compound corresponds to one line of Table B Table 82
Compounds of the formula Id.6 where $X_n$ is hydrogen, $Y^1$ is oxygen and the combination of the radicals $R^1$, $R^3$ and $R^4$ for each compound corresponds to one line of Table B

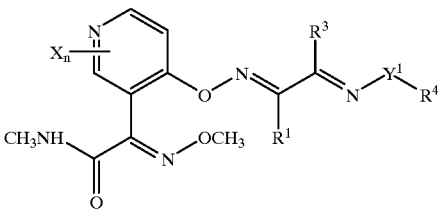

(Id.6)

Table 83
Compounds of the formula Id.6 where $X_n$ is hydrogen, $Y^1$ is NH and the combination of the radicals $R^1$, $R^3$ and $R^4$ for each compound corresponds to one line of Table B Table 84
Compounds of the formula Id.6 where $X_n$ is hydrogen, $Y^1$ is $NCH_3$ and the combination of the radicals $R^1$, $R^3$ and $R^4$ for each compound corresponds to one line of Table B Table 85
Compounds of the formula Id.7 where $X_n$ is hydrogen, $Y^1$ is oxygen and the combination of the radicals $R^1$, $R^3$ and $R^4$ for each compound corresponds to one line of Table B

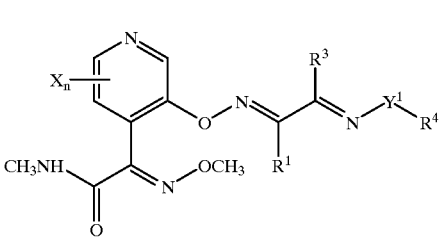

(Id.7)

Table 86
Compounds of the formula Id.7 where $X_n$ is hydrogen, $Y^1$ is NH and the combination of the radicals $R^1$, $R^3$ and $R^4$ for each compound corresponds to one line of Table B Table 87
Compounds of the formula Id.7 where $X_n$ is hydrogen, $Y^1$ is $NCH_3$ and the combination of the radicals $R^1$, $R^3$ and $R^4$ for each compound corresponds to one line of Table B Table 88
Compounds of the formula Id.8 where $X_n$ is hydrogen, $Y^1$ is oxygen and the combination of the radicals $R^1$, $R^3$ and $R^4$ for each compound corresponds to one line of Table B

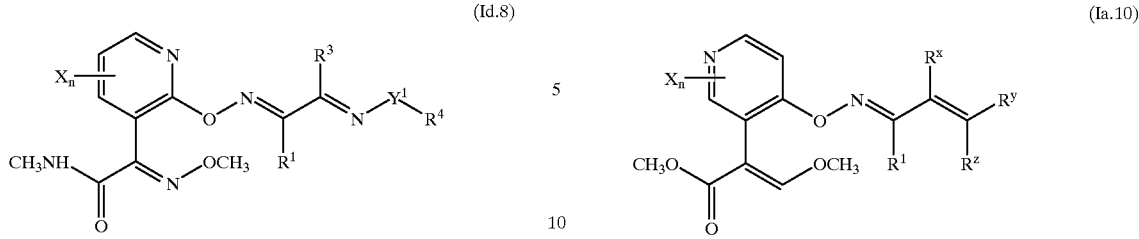

(Id.8)

Table 89

Compounds of the formula Id.8 where $X_n$ is hydrogen, $Y^1$ is NH and the combination of the radicals $R^1$, $R^3$ and $R^4$ for each compound corresponds to one line of Table B Table 90

Compounds of the formula Id.8 where $X_n$ is hydrogen, $Y^1$ is $NCH_3$ and the combination of the radicals $R^1$, $R^3$ and $R^4$ for each compound corresponds to one line of Table B Table 91

Compounds of the formula Id.8 where $X_n$ is 6-$CF_3$, $Y^1$ is oxygen and the combination of the radicals $R^1$, $R^3$ and $R^4$ for each compound corresponds to one line of Table B Table 92

Compounds of the formula Id.8 where $X_n$ is 6-$CH(CH_3)_2$, $Y^1$ is oxygen and the combination of the radicals $R^1$, $R^3$ and $R^4$ for each compound corresponds to one line of Table B Table 93

Compounds of the formula Id.8 where $X_n$ is 6-$CF_3$, $Y^1$ is NH and the combination of the radicals $R^1$, $R^3$ and $R^4$ for each compound corresponds to one line of Table B Table 94

Compounds of the formula Id.8 where $X_n$ is 6-$CH(CH_3)_2$, $Y^1$ is NH and the combination of the radicals $R^1$, $R^3$ and $R^4$ for each compound corresponds to one line of Table B Table 95

Compounds of the formula Id.8 where $X_n$ is 6-$CF_3$, $Y^1$ is $NCH_3$ and the combination of the radicals $R^1$, $R^3$ and $R^4$ for each compound corresponds to one line of Table B Table 96

Compounds of the formula Id.8 where $X_n$ is 6-$CH(CH_3)_2$, $Y^1$ is $NCH_3$ and the combination of the radicals $R^1$, $R^3$ and $R^4$ for each compound corresponds to one line of Table B Table 97

Compounds of the formula Ia.9 where $X_n$ is hydrogen and the combination of the radicals $R^1$, $R^x$, $R^y$ and $R^z$ for each compound corresponds to one line of Table C

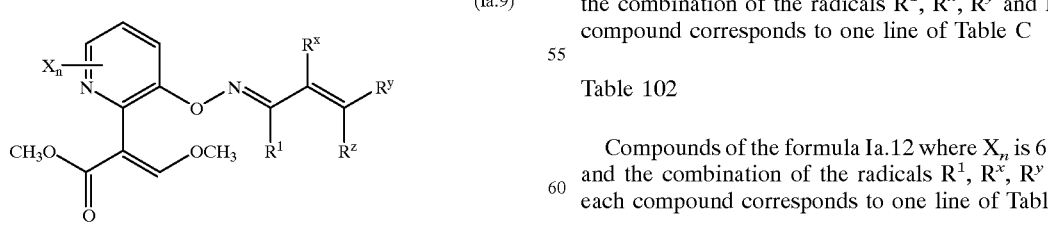

(Ia.9)

Table 98

Compounds of the formula Ia.10 where $X_n$ is hydrogen and the combination of the radicals $R^1$, $R^x$, $R^y$ and $R^z$ for each compound corresponds to one line of Table C Table 99

Compounds of the formula Ia.11 where $X_n$ is hydrogen and the combination of the radicals $R^1$, $R^x$, $R^y$ and $R^z$ for each compound corresponds to one line of Table C (Ia.10)

(Ia.11)

Table 100

Compounds of the formula Ia.12 where $X_n$ is hydrogen and the combination of the radicals $R^1$, $R^x$, $R^y$ and $R^z$ for each compound corresponds to one line of Table C (Ia.12)

Table 101

Compounds of the formula Ia.12 where $X_n$ is 6-$CF_3$ and the combination of the radicals $R^1$, $R^x$, $R^y$ and $R^z$ for each compound corresponds to one line of Table C Table 102

Compounds of the formula Ia.12 where $X_n$ is 6-$CH(CH_3)_2$ and the combination of the radicals $R^1$, $R^x$, $R^y$ and $R^z$ for each compound corresponds to one line of Table C Table 103

Compounds of the formula Ib.9 where $X_n$ is hydrogen and the combination of the radicals $R^1$, $R^x$, $R^y$ and $R^z$ for each compound corresponds to one line of Table C (Ib.9)

Table 104
Compounds of the formula Ib.10 where $X_n$ is hydrogen and the combination of the radicals $R^1$, $R^x$, $R^y$ and $R^z$ for each compound corresponds to one line of Table C (Ib.10)

Table 105
Compounds of the formula Ib.11 where $X_n$ is hydrogen and the combination of the radicals $R^1$, $R^x$, $R^y$ and $R^z$ for each compound corresponds to one line of Table C (Ib.11)

Table 106
Compounds of the formula Ib.12 where $X_n$ is hydrogen and the combination of the radicals $R^1$, $R^x$, $R^y$ and $R^z$ for each compound corresponds to one line of Table C (Ib.12)

Table 107
Compounds of the formula Ib.12 where $X_n$ is 6-$CF_3$ and the combination of the radicals $R^1$, $R^x$, $R^y$ and $R^z$ for each compound corresponds to one line of Table C

Table 108
Compounds of the formula Ib.12 where $X_n$ is 6-CH$(CH_3)_2$ and the combination of the radicals $R^1$, $R^x$, $R^y$ and $R^z$ for each compound corresponds to one line of Table C

Table 109
Compounds of the formula Ic.9 where $X_n$ is hydrogen and the combination of the radicals $R^1$, $R^x$, $R^y$ and $R^z$ for each compound corresponds to one line of Table C (Ic.9)

Table 110
Compounds of the formula Ic.10 where $X_n$ is hydrogen and the combination of the radicals $R^1$, $R^x$, $R^y$ and $R^z$ for each compound corresponds to one line of Table C (Ic.10)

Table 111
Compounds of the formula Ic.11 where $X_n$ is hydrogen and the combination of the radicals $R^1$, $R^x$, $R^y$ and $R^z$ for each compound corresponds to one line of Table C (Ic.11)

Table 112
Compounds of the formula Ic.12 where $X_n$ is hydrogen and the combination of the radicals $R^1$, $R^x$, $R^y$ and $R^z$ for each compound corresponds to one line of Table C (Ic.12)

Table 113
Compounds of the formula Ic.12 where $X_n$ is 6-$CF_3$ and the combination of the radicals $R^1$, $R^x$, $R^y$ and $R^z$ for each compound corresponds to one line of Table C

Table 114
Compounds of the formula Ic.12 where $X_n$ is 6-CH(CH$_3$)$_2$ and the combination of the radicals $R^1$, $R^x$, $R^y$ and $R^z$ for each compound corresponds to one line of Table C

Table 115
Compounds of the formula Id.9 where $X_n$ is hydrogen and the combination of the radicals $R^1$, $R^x$, $R^y$ and $R^z$ for each compound corresponds to one line of Table C

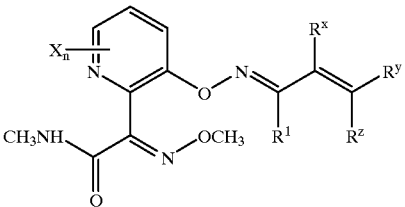
(Id.9)

Table 116
Compounds of the formula Id.10 where $X_n$ is hydrogen and the combination of the radicals $R^1$, $R^x$, $R^y$ and $R^z$ for each compound corresponds to one line of Table C

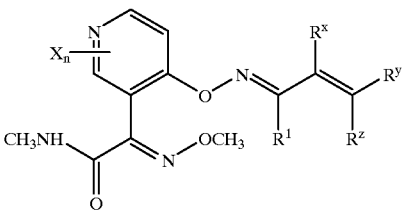
(Id.10)

Table 117
Compounds of the formula Id.11 where $X_n$ is hydrogen and the combination of the radicals $R^1$, $R^x$, $R^y$ and $R^z$ for each compound corresponds to one line of Table C

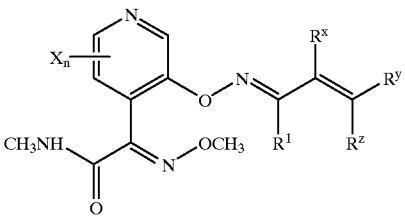
(Id.11)

Table 118
Compounds of the formula Id.12 where $X_n$ is hydrogen and the combination of the radicals $R^1$, $R^x$, $R^y$ and $R^z$ for each compound corresponds to one line of Table C

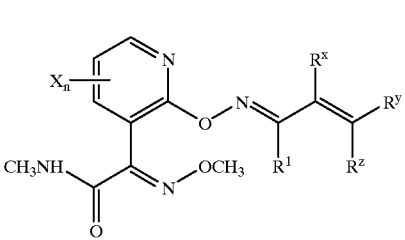
(Id.12)

Table 119
Compounds of the formula Id.12 where $X_n$ is 6-CF$_3$ and the combination of the radicals $R^1$, $R^x$, $R^y$ and $R^z$ for each compound corresponds to one line of Table C

Table 120
Compounds of the formula Id.12 where $X_n$ is 6-CH(CH$_3$)$_2$ and the combination of the radicals $R^1$, $R^x$, $R^y$ and $R^z$ for each compound corresponds to one line of Table C

TABLE A

| No. | $R^1$ | $R^2$ |
|---|---|---|
| A.1 | H | CH$_3$ |
| A.2 | H | CH$_2$CH$_3$ |
| A.3 | H | CH$_2$CH$_2$CH$_3$ |
| A.4 | H | CH(CH$_3$)$_2$ |
| A.5 | H | CH$_2$CH$_2$CH$_2$CH$_3$ |
| A.6 | H | C(CH$_3$)$_3$ |
| A.7 | H | CH(CH$_3$)CH$_2$CH$_3$ |
| A.8 | H | C$_6$H$_5$ |
| A.9 | H | 2-F—C$_6$H$_4$ |
| A.10 | H | 3-F—C$_6$H$_4$ |
| A.11 | H | 4-F—C$_6$H$_4$ |
| A.12 | H | 3-CH$_3$—C$_6$H$_4$ |
| A.13 | H | 3-OCH$_3$—C$_6$H$_4$ |
| A.14 | H | 3-CF$_3$—C$_6$H$_4$ |
| A.15 | H | 3-Cl—C$_6$H$_4$ |
| A.16 | H | 2-CH$_3$—C$_6$H$_4$ |
| A.17 | H | 4-CH$_3$—C$_6$H$_4$ |
| A.18 | H | cyclopropyl |
| A.19 | H | cyclohexyl |
| A.20 | H | CH$_2$CH$_2$Cl |
| A.21 | H | CH$_2$CH$_2$CH$_2$CN |
| A.22 | H | CH$_2$—C$_6$H$_5$ |
| A.23 | H | CH$_2$CH$_2$CH$_2$CH$_2$—OCH$_3$ |
| A.24 | H | CH$_2$CH$_2$—OCH$_2$CH$_3$ |
| A.25 | H | CH$_2$C(CH$_3$)=NOCH$_3$ |
| A.26 | H | CH$_2$-[4-F—C$_6$H$_4$] |
| A.27 | H | CH$_2$-[3-CN—C$_6$H$_4$] |
| A.28 | H | 3-CN—C$_6$H$_4$ |
| A.29 | H | 3,5-(CH$_3$)$_2$—C$_6$H$_3$ |
| A.30 | H | 3-COCH$_3$—C$_6$H$_4$ |
| A.31 | H | 3-[C(CH$_3$)=NOCH$_3$]—C$_6$H$_4$ |
| A.32 | H | 1-naphthyl |
| A.33 | H | CH$_2$CH$_2$—O—C$_6$H$_5$ |
| A.34 | H | CH$_2$—(3-Cl-pyridin-5-yl) |
| A.35 | H | 4-OCH$_3$-pyridin-2-yl |
| A.36 | H | CH$_2$—[5-Cl-pyrazin-2-yl] |
| A.37 | H | 2-thienyl |
| A.38 | H | 3-CH(CH$_3$)$_2$-isoxazol-5-yl |
| A.39 | H | 3-C$_6$H$_5$-pyrazol-1-yl |
| A.40 | H | OCH(CH$_3$)$_2$ |
| A.41 | H | OCH$_2$CH$_2$CH$_2$CH$_2$CH$_3$ |
| A.42 | H | O-[4-F—C$_6$H$_4$] |
| A.43 | H | OCH$_2$-[4-F—C$_6$H$_4$] |
| A.44 | H | O-[6-CH$_3$-pyridin-2-yl] |
| A.45 | H | O—CO-[4-Cl—C$_6$H$_4$] |
| A.46 | H | NH-[4-Cl—C$_6$H$_4$] |
| A.47 | CH$_3$ | CH$_3$ |
| A.48 | CH$_3$ | CH$_2$CH$_3$ |
| A.49 | CH$_3$ | CH$_2$CH$_2$CH$_3$ |
| A.50 | CH$_3$ | CH(CH$_3$)$_2$ |
| A.51 | CH$_3$ | CH$_2$CH$_2$CH$_2$CH$_3$ |
| A.52 | CH$_3$ | C(CH$_3$)$_3$ |
| A.53 | CH$_3$ | CH(CH$_3$)CH$_2$CH$_3$ |
| A.54 | CH$_3$ | C$_6$H$_5$ |
| A.55 | CH$_3$ | 2-F—C$_6$H$_4$ |
| A.56 | CH$_3$ | 3-F—C$_6$H$_4$ |
| A.57 | CH$_3$ | 4-F—C$_6$H$_4$ |
| A.58 | CH$_3$ | 3-CH$_3$—C$_6$H$_4$ |
| A.59 | CH$_3$ | 3-OCH$_3$—C$_6$H$_4$ |
| A.60 | CH$_3$ | 3-CF$_3$—C$_6$H$_4$ |
| A.61 | CH$_3$ | 3-Cl—C$_6$H$_4$ |
| A.62 | CH$_3$ | 2-CH$_3$—C$_6$H$_4$ |
| A.63 | CH$_3$ | 4-CH$_3$—C$_6$H$_4$ |
| A.64 | CH$_3$ | cyclopropyl |
| A.65 | CH$_3$ | cyclohexyl |
| A.66 | CH$_3$ | CH$_2$CH$_2$Cl |
| A.67 | CH$_3$ | CH$_2$CH$_2$CH$_2$CN |
| A.68 | CH$_3$ | CH$_2$—C$_6$H$_5$ |

TABLE A-continued

| No. | R¹ | R² |
|---|---|---|
| A.69 | $CH_3$ | $CH_2CH_2CH_2CH_2$—$OCH_3$ |
| A.70 | $CH_3$ | $CH_2CH_2$—$OCH_2CH_3$ |
| A.71 | $CH_3$ | $CH_2C(CH_3)$=$NOCH_3$ |
| A.72 | $CH_3$ | $CH_2$-[4-F—$C_6H_4$] |
| A.73 | $CH_3$ | $CH_2$-[3-CN—$C_6H_4$] |
| A.147 | $CH_3$ | 3-CN—$C_6H_4$ |
| A.148 | $CH_3$ | 3,5-$(CH_3)_2$—$C_6H_3$ |
| A.149 | $CH_3$ | 3-$COCH_3$—$C_6H_4$ |
| A.150 | $CH_3$ | 3-[C($CH_3$)=$NOCH_3$]—$C_6H_4$ |
| A.151 | $CH_3$ | 1-naphthyl |
| A.152 | $CH_3$ | $CH_2CH_2$—O—$C_6H_5$ |
| A.153 | $CH_3$ | $CH_2$-[3-Cl-pyridin-5-yl] |
| A.154 | $CH_3$ | 4-$OCH_3$-pyridin-2-yl |
| A.155 | $CH_3$ | $CH_2$-[5-Cl-pyrazin-2-yl] |
| A.156 | $CH_3$ | 2-thienyl |
| A.157 | $CH_3$ | 3-$CH(CH_3)_2$-isoxazol-5-yl |
| A.158 | $CH_3$ | 3-$C_6H_5$-pyrazol-1-yl |
| A.159 | $CH_3$ | $OCH(CH_3)_2$ |
| A.160 | $CH_3$ | $OCH_2CH_2CH_2CH_2CH_3$ |
| A.161 | $CH_3$ | O-[4-F—$C_6H_4$] |
| A.162 | $CH_3$ | $OCH_2$-[4-F—$C_6H_4$] |
| A.163 | $CH_3$ | O-[6-$CH_3$-pyridin-2-yl] |
| A.164 | $CH_3$ | O—CO-[4-Cl—$C_6H_4$] |
| A.165 | $CH_3$ | NH-[4-Cl—$C_6H_4$] |
| A.166 | OH | $CH_3$ |
| A.167 | OH | $CH_2CH_2CH_2CH_3$ |
| A.168 | OH | $CH(CH_3)_2$ |
| A.169 | OH | 3-$CH_3$—$C_6H_4$ |
| A.170 | OH | $CH_2$—$C_6H_5$ |
| A.171 | OH | 3,5-$Cl_2$—$C_6H_3$ |
| A.172 | $OCH_3$ | $CH_3$ |
| A.173 | $OCH_3$ | $CH_2CH_2CH_3$ |
| A.174 | $OCH_3$ | $CH(CH_3)_2$ |
| A.175 | $OCH_3$ | $CH_2CH_2CH_2CH_2CH_3$ |
| A.176 | $OCH_3$ | 3-$CH_3$—$C_6H_4$ |
| A.177 | $OCH_3$ | $CH_2$—$C_6H_5$ |
| A.178 | $OCH_3$ | 3,5-$Cl_2$—$C_6H_3$ |
| A.179 | $OCH_2CH_3$ | $CH_3$ |
| A.180 | $OCH_2CH_3$ | $CH_2CH_2CH_3$ |
| A.181 | $OCH_2CH_3$ | $CH(CH_3)_2$ |
| A.182 | $OCH_2CH_3$ | $CH_2CH_2CH_2CH_2CH_3$ |
| A.183 | $OCH_2CH_3$ | 3-$CH_3$—$C_6H_4$ |
| A.184 | $OCH_2CH_3$ | $CH_2$-[4-F—$C_6H_4$] |
| A.185 | $OCH_2CH_3$ | 2,4-$F_2$—$C_6H_3$ |
| A.186 | cyclopropyl | $CH_3$ |
| A.187 | cyclopropyl | $CH_2CH_3$ |
| A.188 | cyclopropyl | $OCH_2CH_3$ |
| A.189 | cyclopropyl | $C_6H_5$ |
| A.190 | Cl | $C_6H_5$ |
| A.191 | Cl | $CH_3$ |
| A.192 | Cl | $CH(CH_3)_2$ |
| A.193 | Cl | 3-$CH_3$—$C_6H_4$ |
| A.194 | Cl | 3-CN—$C_6H_4$ |
| A.195 | Cl | $CH_2CH_2$—O—$C_6H_5$ |
| A.196 | Cl | $CH_2CH_2$—$OCH_2CH_3$ |
| A.197 | Cl | $CH_2$-[4-F—$C_6H_4$] |
| A.198 | $SCH_3$ | $CH_3$ |
| A.199 | $SCH_3$ | $C_6H_5$ |
| A.200 | $SCH_3$ | $CH(CH_3)_2$ |
| A.201 | $CH(CH_3)_2$ | $CH_3$ |
| A.202 | $CH(CH_3)_2$ | $CH_2CH_3$ |
| A.203 | $CH(CH_3)_2$ | $C_6H_5$ |
| A.204 | $CH(CH_3)_2$ | $OCH_3$ |
| A.205 | $CH(CH_3)_2$ | $OCH(CH_3)_2$ |
| A.206 | $CH(CH_3)_2$ | 3-$CH_3$—$C_6H_4$ |
| A.207 | CN | $CH_3$ |
| A.208 | CN | 3-$CH_3$—$C_6H_4$ |
| A.209 | CN | $CH_2$-[2,4-$Cl_2$—$C_6H_3$] |
| A.210 | CN | $CH_2CH_2CH_2CH_3$ |
| A.211 | CN | $CH(CH_3)_2$ |
| A.212 | $CH_2CH_3$ | $CH_3$ |
| A.213 | $CH_2CH_3$ | $CH_2CH_3$ |
| A.214 | $CH_2CH_3$ | $CH_2CH_2CH_3$ |
| A.215 | $CH_2CH_3$ | $CH(CH_3)_2$ |
| A.216 | $CH_2CH_3$ | $CH_2CH_2CH_2CH_3$ |
| A.217 | $CH_2CH_3$ | $C(CH_3)_3$ |
| A.218 | $CH_2CH_3$ | $CH(CH_3)CH_2CH_3$ |
| A.219 | $CH_2CH_3$ | $C_6H_5$ |
| A.220 | $CH_2CH_3$ | 2-F—$C_6H_4$ |
| A.221 | $CH_2CH_3$ | 3-F—$C_6H_4$ |
| A.222 | $CH_2CH_3$ | 4-F—$C_6H_4$ |
| A.223 | $CH_2CH_3$ | 3-$CH_3$—$C_6H_4$ |
| A.224 | $CH_2CH_3$ | 3-$OCH_3$—$C_6H_4$ |
| A.225 | $CH_2CH_3$ | 3-$CF_3$—$C_6H_4$ |
| A.226 | $CH_2CH_3$ | 3-Cl—$C_6H_4$ |
| A.227 | $CH_2CH_3$ | 2-$CH_3$—$C_6H_4$ |
| A.228 | $CH_2CH_3$ | 4-$CH_3$—$C_6H_4$ |
| A.229 | $CH_2CH_3$ | cyclopropyl |
| A.230 | $CH_2CH_3$ | cyclohexyl |
| A.231 | $CH_2CH_3$ | $CH_2CH_2Cl$ |
| A.232 | $CH_2CH_3$ | $CH_2CH_2CH_2CN$ |
| A.233 | $CH_2CH_3$ | $CH_2$—$C_6H_5$ |
| A.234 | $CH_2CH_3$ | $CH_2CH_2CH_2CH_2$—$OCH_3$ |
| A.235 | $CH_2CH_3$ | $CH_2CH_2$—$OCH_2CH_3$ |
| A.236 | $CH_2CH_3$ | $CH_2C(CH_3)$=$NOCH_3$ |
| A.237 | $CH_2CH_3$ | $CH_2$-[4-F—$C_6H_4$] |
| A.238 | $CH_2CH_3$ | $CH_2$-[3-CN—$C_6H_4$] |
| A.239 | $CH_2CH_3$ | 3-CN—$C_6H_4$ |
| A.240 | $CH_2CH_3$ | 3,5-$(CH_3)_2$—$C_6H_3$ |
| A.241 | $CH_2CH_3$ | 3-$COCH_3$—$C_6H_4$ |
| A.242 | $CH_2CH_3$ | 3-[C($CH_3$)=$NOCH_3$]—$C_6H_4$ |
| A.243 | $CH_2CH_3$ | 1-naphthyl |
| A.244 | $CH_2CH_3$ | $CH_2CH_2$—O—$C_6H_5$ |
| A.245 | $CH_2CH_3$ | $CH_2$-[3-Cl-pyridin-5-yl] |
| A.246 | $CH_2CH_3$ | 4-$OCH_3$-pyridin-2-yl |
| A.247 | $CH_2CH_3$ | $CH_2$-[5-Cl-pyrazin-2-yl] |
| A.248 | $CH_2CH_3$ | 2-thienyl |
| A.249 | $CH_2CH_3$ | 3-$CH(CH_3)_2$-isoxazol-5-yl |
| A.250 | $CH_2CH_3$ | 3-$C_6H_5$-pyrazol-1-yl |
| A.251 | $CH_2CH_3$ | $OCH(CH_3)_2$ |
| A.252 | $CH_2CH_3$ | $OCH_2CH_2CH_2CH_2CH_3$ |
| A.253 | $CH_2CH_3$ | O-[4-F—$C_6H_4$] |
| A.254 | $CH_2CH_3$ | $OCH_2$-[4-F—$C_6H_4$] |
| A.255 | $CH_2CH_3$ | O-[6-$CH_3$-pyridin-2-yl] |
| A.256 | $CH_2CH_3$ | O—CO-[4-Cl—$C_6H_4$] |
| A.257 | $CH_2CH_3$ | NH-[4-Cl—$C_6H_4$] |
| A.258 | $CH_3$ | $CH_2ON$=$C(CH_3)_2$ |
| A.259 | $CH_3$ | $CH_2ON$=$C(CH_3)$—$CH_2CH_3$ |
| A.260 | $CH_3$ | $CH_2ON$=$C(CH_3)$—$C_6H_5$ |
| A.261 | $CH_3$ | $CH_2ON$=$C(CH_3)$-[4-Cl—$C_6H_4$] |
| A.262 | $CH_2CH_3$ | $CH_2ON$=$C(CH_3)_2$ |
| A.263 | $CH_2CH_3$ | $CH_2ON$=$C(CH_3)$—$CH_2CH_3$ |
| A.264 | $CH_2CH_3$ | $CH_2ON$=$C(CH_3)$—$C_6H_5$ |
| A.265 | $CH_2CH_3$ | $CH_2ON$=$C(CH_3)$-[4-Cl—$C_6H_4$] |
| A.266 | $CH_2$—$C_6H_5$ | $CH_2ON$=$C(CH_3)_2$ |
| A.267 | $CH_2$—$C_6H_5$ | $CH_2ON$=$C(CH_3)$—$CH_2CH_3$ |
| A.268 | $CH_2$—$C_6H_5$ | $CH_2ON$=$C(CH_3)$—$C_6H_5$ |
| A.269 | $CH_2$—$C_6H_5$ | $CH_2ON$=$C(CH_3)$-[4-Cl—$C_6H_4$] |
| A.270 | H | CH=CH—$C_6H_5$ |
| A.271 | H | CH=C($CH_3$)—$C_6H_5$ |
| A.272 | H | CH=CCl—$C_6H_5$ |
| A.273 | H | C($CH_3$)=CH—$C_6H_5$ |
| A.274 | H | CCl=CH—$C_6H_5$ |
| A.275 | H | CH=CH-[4-F—$C_6H_4$] |
| A.276 | H | CH=C($CH_3$)-[4-F—$C_6H_4$] |
| A.277 | H | CH=CCl-[4-F—$C_6H_4$] |
| A.278 | H | CCl=CH-[4-F—$C_6H_4$] |
| A.279 | H | C($CH_3$)=CH-[4-F—$C_6H_4$] |
| A.280 | $CH_3$ | CH=CH—$C_6H_5$ |
| A.281 | $CH_3$ | CH=C($CH_3$)—$C_6H_5$ |
| A.282 | $CH_3$ | CH=CCl—$C_6H_5$ |
| A.283 | $CH_3$ | C($CH_3$)=CH—$C_6H_5$ |
| A.284 | $CH_3$ | CCl=CH—$C_6H_5$ |
| A.285 | $CH_3$ | CH=CH-[4-F—$C_6H_4$] |
| A.286 | $CH_3$ | CH=C($CH_3$)-[4-F—$C_6H_4$] |
| A.287 | $CH_3$ | CH=CCl-[4-F—$C_6H_4$] |
| A.288 | $CH_3$ | CCl=CH-[4-F—$C_6H_4$] |
| A.289 | $CH_3$ | C($CH_3$)=CH-[4-F—$C_6H_4$] |
| A.290 | $CH_2CH_3$ | CH=CH—$C_6H_5$ |
| A.291 | $CH_2CH_3$ | CH=C($CH_3$)—$C_6H_5$ |
| A.292 | $CH_2CH_3$ | CH=CCl—$C_6H_5$ |
| A.293 | $CH_2CH_3$ | C($CH_3$)=CH—$C_6H_5$ |
| A.294 | $CH_2CH_3$ | CCl=CH—$C_6H_5$ |
| A.295 | $CH_2CH_3$ | CH=CH-[4-F—$C_6H_4$] |

TABLE A-continued

| No. | R¹ | R² |
|---|---|---|
| A.296 | CH₂CH₃ | CH=C(CH₃)-[4-F—C₆H₄] |
| A.297 | CH₂CH₃ | CH=CCl-[4-F—C₆H₄] |
| A.298 | CH₂CH₃ | CCl=CH-[4-F—C₆H₄] |
| A.299 | CH₂CH₃ | C(CH₃)=CH-[4-F—C₆H₄] |
| A.300 | CH₂—C₆H₅ | CH=CH—C₆H₅ |
| A.301 | CH₂—C₆H₅ | CH=C(CH₃)—C₆H₅ |
| A.302 | CH₂—C₆H₅ | CH=CCl—C₆H₅ |
| A.303 | CH₂—C₆H₅ | C(CH₃)=CH—C₆H₅ |
| A.304 | CH₂—C₆H₅ | CCl=CH—C₆H₅ |
| A.305 | CH₂—C₆H₅ | CH=CH-[4-F—C₆H₄] |
| A.306 | CH₂—C₆H₅ | CH=C(CH₃)-[4-F—C₆H₄] |
| A.307 | CH₂—C₆H₅ | CH=CCl-[4-F—C₆H₄] |
| A.308 | CH₂—C₆H₅ | CCl=CH-[4-F—C₆H₄] |
| A.309 | CH₂—C₆H₅ | C(CH₃)=CH-[4-F—C₆H₄] |
| A.310 | H | CH(CH₃)—C(CH₃)=NOCH₃ |
| A.311 | H | CH(CH₃)—C(CH₃)=NOCH₂CH₃ |
| A.312 | H | CH(CH₃)—C₆H₅ |
| A.313 | H | CH(CH₃)-[4-F—C₆H₄] |
| A.314 | H | 1-C₆H₅-cyclopropyl |
| A.315 | H | 1-[4-Cl—C₆H₄]-cyclopropyl |
| A.316 | H | CH₂C(CH₃)=NOCH₃ |
| A.317 | H | CH₂C(CH₃)=NOCH₂CH₃ |
| A.318 | H | 1-[C(CH₃)=NOCH₃]-cyclopropyl |
| A.319 | CH₃ | CH(CH₃)—C(CH₃)=NOCH₃ |
| A.320 | CH₃ | CH(CH₃)—C(CH₃)=NOCH₂CH₃ |
| A.321 | CH₃ | CH(CH₃)—C₆H₅ |
| A.322 | CH₃ | CH(CH₃)-[4-F—C₆H₄] |
| A.323 | CH₃ | 1-C₆H₅-cyclopropyl |
| A.324 | CH₃ | 1-[4-Cl—C₆H₄]-cyclopropyl |
| A.325 | CH₃ | CH₂C(CH₃)=NOCH₃ |
| A.326 | CH₃ | CH₂C(CH₃)=NOCH₂CH₃ |
| A.327 | CH₃ | 1-[C(CH₃)=NOCH₃]-cyclopropyl |
| A.328 | CH₂CH₃ | CH(CH₃)—C(CH₃)=NOCH₃ |
| A.329 | CH₂CH₃ | CH(CH₃)—C(CH₃)=NOCH₂CH₃ |
| A.330 | CH₂CH₃ | CH(CH₃)—C₆H₅ |
| A.331 | CH₂CH₃ | CH(CH₃)-[4-F—C₆H₄] |
| A.332 | CH₂CH₃ | 1-C₆H₅-cyclopropyl |
| A.333 | CH₂CH₃ | 1-[4-Cl—C₆H₄]-cyclopropyl |
| A.334 | CH₂CH₃ | CH₂C(CH₃)=NOCH₃ |
| A.335 | CH₂CH₃ | CH₂C(CH₃)=NOCH₂CH₃ |
| A.336 | CH₂CH₃ | 1-[C(CH₃)=NOCH₃]-cyclopropyl |
| A.337 | CH₂—C₆H₅ | CH(CH₃)—C(CH₃)=NOCH₃ |
| A.338 | CH₂—C₆H₅ | CH(CH₃)—C(CH₃)=NOCH₂CH₃ |
| A.339 | CH₂—C₆H₅ | CH(CH₃)—C₆H₅ |
| A.340 | CH₂—C₆H₅ | CH(CH₃)-[4-F—C₆H₄] |
| A.341 | CH₂—C₆H₅ | 1-C₆H₅-cyclopropyl |
| A.342 | CH₂—C₆H₅ | 1-[4-Cl—C₆H₄]-cyclopropyl |
| A.343 | CH₂—C₆H₅ | CH₂C(CH₃)=NOCH₃ |
| A.344 | CH₂—C₆H₅ | CH₂C(CH₃)=NOCH₂CH₃ |
| A.345 | CH₂—C₆H₅ | 1-[C(CH₃)=NOCH₃]-cyclopropyl |
| A.346 | | —(CH₂)₄— |
| A.347 | | —(CH₂)₅— |
| A.348 | | —(CH₂)₂—O—(CH₂)₂— |
| A.349 | | —(CH₂)₂—S—(CH₂)₂— |
| A.350 | | —(CH₂)₂—CH(CH₃)—(CH₂)₂— |
| A.351 | | —(CH₂)₂—C(=O)—(CH₂)₂— |
| A.352 | | —(CH₂)₂—C(=NOCH₃)—(CH₂)₂— |
| A.353 | | —(CH₂)₂—C(OCH₃)₂—(CH₂)₂— |
| A.354 | | —CH₂—CH(CH₃)—CH₂—CH(CH₃)—CH₂— |
| A.355 | | —(CH₂)₃—CH(CH₃)—CH₂— |
| A.356 | | —CH=CH—C(=NOCH₃)—CH=CH— |
| A.357 | | —CH₂—C(=NOCH₃)—(CH₂)₃— |
| A.358 | CH₃ | CF₃ |
| A.359 | H | CF₃ |
| A.360 | CF₃ | CH₃ |
| A.361 | CF₃ | H |

TABLE B

| No. | R¹ | R³ | R⁴ |
|---|---|---|---|
| B.1 | Cl | H | H |
| B.2 | Cl | CH₃ | H |
| B.3 | Cl | CH₂CH₃ | H |

TABLE B-continued

| No. | R¹ | R³ | R⁴ |
|---|---|---|---|
| B.4 | Cl | CF₃ | H |
| B.5 | Cl | CHF₂ | H |
| B.6 | Cl | CH₂F | H |
| B.7 | Cl | Cl | H |
| B.8 | Cl | OCH₃ | H |
| B.9 | Cl | OCH₂CH₃ | H |
| B.10 | Cl | CN | H |
| B.11 | CH₃ | H | H |
| B.12 | CH₃ | CH₃ | H |
| B.13 | CH₃ | CH₂CH₃ | H |
| B.14 | CH₃ | CF₃ | H |
| B.15 | CH₃ | CHF₂ | H |
| B.16 | CH₃ | CH₂F | H |
| B.17 | CH₃ | Cl | H |
| B.18 | CH₃ | OCH₃ | H |
| B.19 | CH₃ | OCH₂CH₃ | H |
| B.20 | CH₃ | CN | H |
| B.21 | CF₃ | H | H |
| B.22 | CF₃ | CH₃ | H |
| B.23 | CF₃ | CH₂CH₃ | H |
| B.24 | CF₃ | CF₃ | H |
| B.25 | CF₃ | CHF₂ | H |
| B.26 | CF₃ | CH₂F | H |
| B.27 | CF₃ | Cl | H |
| B.28 | CF₃ | OCH₃ | H |
| B.29 | CF₃ | OCH₂CH₃ | H |
| B.30 | CF₃ | CN | H |
| B.31 | Cl | H | CH₃ |
| B.32 | Cl | CH₃ | CH₃ |
| B.33 | Cl | CH₂CH₃ | CH₃ |
| B.34 | Cl | CF₃ | CH₃ |
| B.35 | Cl | CHF₂ | CH₃ |
| B.36 | Cl | CH₂F | CH₃ |
| B.37 | Cl | Cl | CH₃ |
| B.38 | Cl | OCH₃ | CH₃ |
| B.39 | Cl | OCH₂CH₃ | CH₃ |
| B.40 | Cl | CN | CH₃ |
| B.41 | CH₃ | H | CH₃ |
| B.42 | CH₃ | CH₃ | CH₃ |
| B.43 | CH₃ | CH₂CH₃ | CH₃ |
| B.44 | CH₃ | CF₃ | CH₃ |
| B.45 | CH₃ | CHF₂ | CH₃ |
| B.46 | CH₃ | CH₂F | CH₃ |
| B.47 | CH₃ | Cl | CH₃ |
| B.48 | CH₃ | OCH₃ | CH₃ |
| B.49 | CH₃ | OCH₂CH₃ | CH₃ |
| B.50 | CH₃ | CN | CH₃ |
| B.51 | CF₃ | H | CH₃ |
| B.52 | CF₃ | CH₃ | CH₃ |
| B.53 | CF₃ | CH₂CH₃ | CH₃ |
| B.54 | CF₃ | CF₃ | CH₃ |
| B.55 | CF₃ | CHF₂ | CH₃ |
| B.56 | CF₃ | CH₂F | CH₃ |
| B.57 | CF₃ | Cl | CH₃ |
| B.58 | CF₃ | OCH₃ | CH₃ |
| B.59 | CF₃ | OCH₂CH₃ | CH₃ |
| B.60 | CF₃ | CN | CH₃ |
| B.61 | Cl | H | CH₂CH₃ |
| B.62 | Cl | CH₃ | CH₂CH₃ |
| B.63 | Cl | CH₂CH₃ | CH₂CH₃ |
| B.64 | Cl | CF₃ | CH₂CH₃ |
| B.65 | Cl | CHF₂ | CH₂CH₃ |
| B.66 | Cl | CH₂F | CH₂CH₃ |
| B.67 | Cl | Cl | CH₂CH₃ |
| B.68 | Cl | OCH₃ | CH₂CH₃ |
| B.69 | Cl | OCH₂CH₃ | CH₂CH₃ |
| B.70 | Cl | CN | CH₂CH₃ |
| B.71 | CH₃ | H | CH₂CH₃ |
| B.72 | CH₃ | CH₃ | CH₂CH₃ |
| B.73 | CH₃ | CH₂CH₃ | CH₂CH₃ |
| B.74 | CH₃ | CF₃ | CH₂CH₃ |
| B.75 | CH₃ | CHF₂ | CH₂CH₃ |
| B.76 | CH₃ | CH₂F | CH₂CH₃ |
| B.77 | CH₃ | Cl | CH₂CH₃ |
| B.78 | CH₃ | OCH₃ | CH₂CH₃ |
| B.79 | CH₃ | OCH₂CH₃ | CH₂CH₃ |
| B.80 | CH₃ | CN | CH₂CH₃ |

TABLE B-continued

| No. | R¹ | R³ | R⁴ |
|---|---|---|---|
| B.81 | CF₃ | H | CH₂CH₃ |
| B.82 | CF₃ | CH₃ | CH₂CH₃ |
| B.83 | CF₃ | CH₂CH₃ | CH₂CH₃ |
| B.84 | CF₃ | CF₃ | CH₂CH₃ |
| B.85 | CF₃ | CHF₂ | CH₂CH₃ |
| B.86 | CF₃ | CH₂F | CH₂CH₃ |
| B.87 | CF₃ | Cl | CH₂CH₃ |
| B.88 | CF₃ | OCH₃ | CH₂CH₃ |
| B.89 | CF₃ | OCH₂CH₃ | CH₂CH₃ |
| B.90 | CF₃ | CN | CH₂CH₃ |
| B.91 | Cl | H | CH₂CH₂CH₃ |
| B.92 | Cl | CH₃ | CH₂CH₂CH₃ |
| B.93 | Cl | CH₂CH₃ | CH₂CH₂CH₃ |
| B.94 | Cl | CF₃ | CH₂CH₂CH₃ |
| B.95 | Cl | CHF₂ | CH₂CH₂CH₃ |
| B.96 | Cl | CH₂F | CH₂CH₂CH₃ |
| B.97 | Cl | Cl | CH₂CH₂CH₃ |
| B.98 | Cl | OCH₃ | CH₂CH₂CH₃ |
| B.99 | Cl | OCH₂CH₃ | CH₂CH₂CH₃ |
| B.100 | Cl | CN | CH₂CH₂CH₃ |
| B.101 | CH₃ | H | CH₂CH₂CH₃ |
| B.102 | CH₃ | CH₃ | CH₂CH₂CH₃ |
| B.103 | CH₃ | CH₂CH₃ | CH₂CH₂CH₃ |
| B.104 | CH₃ | CF₃ | CH₂CH₂CH₃ |
| B.105 | CH₃ | CHF₂ | CH₂CH₂CH₃ |
| B.106 | CH₃ | CH₂F | CH₂CH₂CH₃ |
| B.107 | CH₃ | Cl | CH₂CH₂CH₃ |
| B.108 | CH₃ | OCH₃ | CH₂CH₂CH₃ |
| B.109 | CH₃ | OCH₂CH₃ | CH₂CH₂CH₃ |
| B.110 | CH₃ | CN | CH₂CH₂CH₃ |
| B.111 | CF₃ | H | CH₂CH₂CH₃ |
| B.112 | CF₃ | CH₃ | CH₂CH₂CH₃ |
| B.113 | CF₃ | CH₂CH₃ | CH₂CH₂CH₃ |
| B.114 | CF₃ | CF₃ | CH₂CH₂CH₃ |
| B.115 | CF₃ | CHF₂ | CH₂CH₂CH₃ |
| B.116 | CF₃ | CH₂F | CH₂CH₂CH₃ |
| B.117 | CF₃ | Cl | CH₂CH₂CH₃ |
| B.118 | CF₃ | OCH₃ | CH₂CH₂CH₃ |
| B.119 | CF₃ | OCH₂CH₃ | CH₂CH₂CH₃ |
| B.120 | CF₃ | CN | CH₂CH₂CH₃ |
| B.121 | Cl | H | CH(CH₃)₂ |
| B.122 | Cl | CH₃ | CH(CH₃)₂ |
| B.123 | Cl | CH₂CH₃ | CH(CH₃)₂ |
| B.124 | Cl | CF₃ | CH(CH₃)₂ |
| B.125 | Cl | CHF₂ | CH(CH₃)₂ |
| B.126 | Cl | CH₂F | CH(CH₃)₂ |
| B.127 | Cl | Cl | CH(CH₃)₂ |
| B.128 | Cl | OCH₃ | CH(CH₃)₂ |
| B.129 | Cl | OCH₂CH₃ | CH(CH₃)₂ |
| B.130 | Cl | CN | CH(CH₃)₂ |
| B.131 | CH₃ | H | CH(CH₃)₂ |
| B.132 | CH₃ | CH₃ | CH(CH₃)₂ |
| B.133 | CH₃ | CH₂CH₃ | CH(CH₃)₂ |
| B.134 | CH₃ | CF₃ | CH(CH₃)₂ |
| B.135 | CH₃ | CHF₂ | CH(CH₃)₂ |
| B.136 | CH₃ | CH₂F | CH(CH₃)₂ |
| B.137 | CH₃ | Cl | CH(CH₃)₂ |
| B.138 | CH₃ | OCH₃ | CH(CH₃)₂ |
| B.139 | CH₃ | OCH₂CH₃ | CH(CH₃)₂ |
| B.140 | CH₃ | CN | CH(CH₃)₂ |
| B.141 | CF₃ | H | CH(CH₃)₂ |
| B.142 | CF₃ | CH₃ | CH(CH₃)₂ |
| B.143 | CF₃ | CH₂CH₃ | CH(CH₃)₂ |
| B.144 | CF₃ | CF₃ | CH(CH₃)₂ |
| B.145 | CF₃ | CHF₂ | CH(CH₃)₂ |
| B.146 | CF₃ | CH₂F | CH(CH₃)₂ |
| B.147 | CF₃ | Cl | CH(CH₃)₂ |
| B.148 | CF₃ | OCH₃ | CH(CH₃)₂ |
| B.149 | CF₃ | OCH₂CH₃ | CH(CH₃)₂ |
| B.150 | CF₃ | CN | CH(CH₃)₂ |
| B.151 | Cl | H | CH₂CH=CH₂ |
| B.152 | Cl | CH₃ | CH₂CH=CH₂ |
| B.153 | Cl | CH₂CH₃ | CH₂CH=CH₂ |
| B.154 | Cl | CF₃ | CH₂CH=CH₂ |
| B.155 | Cl | CHF₂ | CH₂CH=CH₂ |
| B.156 | Cl | CH₂F | CH₂CH=CH₂ |
| B.157 | Cl | Cl | CH₂CH=CH₂ |
| B.158 | Cl | OCH₃ | CH₂CH=CH₂ |
| B.159 | Cl | OCH₂CH₃ | CH₂CH=CH₂ |
| B.160 | Cl | CN | CH₂CH=CH₂ |
| B.161 | CH₃ | H | CH₂CH=CH₂ |
| B.162 | CH₃ | CH₃ | CH₂CH=CH₂ |
| B.163 | CH₃ | CH₂CH₃ | CH₂CH=CH₂ |
| B.164 | CH₃ | CF₃ | CH₂CH=CH₂ |
| B.165 | CH₃ | CHF₂ | CH₂CH=CH₂ |
| B.166 | CH₃ | CH₂F | CH₂CH=CH₂ |
| B.167 | CH₃ | Cl | CH₂CH=CH₂ |
| B.168 | CH₃ | OCH₃ | CH₂CH=CH₂ |
| B.169 | CH₃ | OCH₂CH₃ | CH₂CH=CH₂ |
| B.170 | CH₃ | CN | CH₂CH=CH₂ |
| B.171 | CF₃ | H | CH₂CH=CH₂ |
| B.172 | CF₃ | CH₃ | CH₂CH=CH₂ |
| B.173 | CF₃ | CH₂CH₃ | CH₂CH=CH₂ |
| B.174 | CF₃ | CF₃ | CH₂CH=CH₂ |
| B.175 | CF₃ | CHF₂ | CH₂CH=CH₂ |
| B.176 | CF₃ | CH₂F | CH₂CH=CH₂ |
| B.177 | CF₃ | Cl | CH₂CH=CH₂ |
| B.178 | CF₃ | OCH₃ | CH₂CH=CH₂ |
| B.179 | CF₃ | OCH₂CH₃ | CH₂CH=CH₂ |
| B.180 | CF₃ | CN | CH₂CH=CH₂ |
| B.181 | Cl | H | CH₂CH=CH—Cl (trans) |
| B.182 | Cl | CH₃ | CH₂CH=CH—Cl (trans) |
| B.183 | Cl | CH₂CH₃ | CH₂CH=CH—Cl (trans) |
| B.184 | Cl | CF₃ | CH₂CH=CH—Cl (trans) |
| B.185 | Cl | CHF₂ | CH₂CH=CH—Cl (trans) |
| B.186 | Cl | CH₂F | CH₂CH=CH—Cl (trans) |
| B.187 | Cl | Cl | CH₂CH=CH—Cl (trans) |
| B.188 | Cl | OCH₃ | CH₂CH=CH—Cl (trans) |
| B.189 | Cl | OCH₂CH₃ | CH₂CH=CH—Cl (trans) |
| B.190 | Cl | CN | CH₂CH=CH—Cl (trans) |
| B.191 | CH₃ | H | CH₂CH=CH—Cl (trans) |
| B.192 | CH₃ | CH₃ | CH₂CH=CH—Cl (trans) |
| B.193 | CH₃ | CH₂CH₃ | CH₂CH=CH—Cl (trans) |
| B.194 | CH₃ | CF₃ | CH₂CH=CH—Cl (trans) |
| B.195 | CH₃ | CHF₂ | CH₂CH=CH—Cl (trans) |
| B.196 | CH₃ | CH₂F | CH₂CH=CH—Cl (transY |
| B.197 | CH₃ | Cl | CH₂CH=CH—Cl (trans) |
| B.198 | CH₃ | OCH₃ | CH₂CH=CH—Cl (trans) |
| B.199 | CH₃ | OCH₂CH₃ | CH₂CH=CH—Cl (trans) |
| B.200 | CH₃ | CN | CH₂CH=CH—Cl (trans) |
| B.201 | CF₃ | H | CH₂CH=CH—Cl (trans) |
| B.202 | CF₃ | CH₃ | CH₂CH=CH—Cl (trans) |
| B.203 | CF₃ | CH₂CH₃ | CH₂CH=CH—Cl (trans) |
| B.204 | CF₃ | CF₃ | CH₂CH=CH—Cl (trans) |
| B.205 | CF₃ | CHF₂ | CH₂CH=CH—Cl (trans) |
| B.206 | CF₃ | CH₂F | CH₂CH=CH—Cl (trans) |
| B.207 | CF₃ | Cl | CH₂CH=CH—Cl (trans) |
| B.208 | CF₃ | OCH₃ | CH₂CH=CH—Cl (trans) |
| B.209 | CF₃ | OCH₂CH₃ | CH₂CH=CH—Cl (trans) |
| B.210 | CF₃ | CN | CH₂CH=CH—Cl (trans) |
| B.211 | Cl | H | CH₂CCl=CH₂ |
| B.212 | Cl | CH₃ | CH₂CCl=CH₂ |
| B.213 | Cl | CH₂CH₃ | CH₂CCl=CH₂ |
| B.214 | Cl | CF₃ | CH₂CCl=CH₂ |
| B.215 | Cl | CHF₂ | CH₂CCl=CH₂ |
| B.216 | Cl | CH₂F | CH₂CCl=CH₂ |
| B.217 | Cl | Cl | CH₂CCl=CH₂ |
| B.218 | Cl | OCH₃ | CH₂CCl=CH₂ |
| B.219 | Cl | OCH₂CH₃ | CH₂CCl=CH₂ |
| B.220 | Cl | CN | CH₂CCl=CH₂ |
| B.221 | CH₃ | H | CH₂CCl=CH₂ |
| B.222 | CH₃ | CH₃ | CH₂CCl=CH₂ |
| B.223 | CH₃ | CH₂CH₃ | CH₂CCl=CH₂ |
| B.224 | CH₃ | CF₃ | CH₂CCl=CH₂ |
| B.225 | CH₃ | CHF₂ | CH₂CCl=CH₂ |
| B.226 | CH₃ | CH₂F | CH₂CCl=CH₂ |
| B.227 | CH₃ | Cl | CH₂CCl=CH₂ |
| B.228 | CH₃ | OCH₃ | CH₂CCl=CH₂ |
| B.229 | CH₃ | OCH₂CH₃ | CH₂CCl=CH₂ |
| B.230 | CH₃ | CN | CH₂CCl=CH₂ |
| B.231 | CF₃ | H | CH₂CCl=CH₂ |
| B.232 | CF₃ | CH₃ | CH₂CCl=CH₂ |
| B.233 | CF₃ | CH₂CH₃ | CH₂CCl=CH₂ |
| B.234 | CF₃ | CF₃ | CH₂CCl=CH₂ |

TABLE B-continued

| No. | R¹ | R³ | R⁴ |
|---|---|---|---|
| B.235 | CF₃ | CHF₂ | CH₂CCl=CH₂ |
| B.236 | CF₃ | CH₂F | CH₂CCl=CH₂ |
| B.237 | CF₃ | Cl | CH₂CCl=CH₂ |
| B.238 | CF₃ | OCH₃ | CH₂CCl=CH₂ |
| B.239 | CF₃ | OCH₂CH₃ | CH₂CCl=CH₂ |
| B.240 | CF₃ | CN | CH₂CCl=CH₂ |
| B.241 | Cl | H | CH₂C≡CH |
| B.242 | Cl | CH₃ | CH₂C≡CH |
| B.243 | Cl | CH₂CH₃ | CH₂C≡CH |
| B.244 | Cl | CF₃ | CH₂C≡CH |
| B.245 | Cl | CHF₂ | CH₂C≡CH |
| B.246 | Cl | CH₂F | CH₂C≡CH |
| B.247 | Cl | Cl | CH₂C≡CH |
| B.248 | Cl | OCH₃ | CH₂C≡CH |
| B.249 | Cl | OCH₂CH₃ | CH₂C≡CH |
| B.250 | Cl | CN | CH₂C≡CH |
| B.251 | CH₃ | H | CH₂C≡CH |
| B.252 | CH₃ | CH₃ | CH₂C≡CH |
| B.253 | CH₃ | CH₂CH₃ | CH₂C≡CH |
| B.254 | CH₃ | CF₃ | CH₂C≡CH |
| B.255 | CH₃ | CHF₂ | CH₂C≡CH |
| B.256 | CH₃ | CH₂F | CH₂C≡CH |
| B.257 | CH₃ | Cl | CH₂C≡CH |
| B.258 | CH₃ | OCH₃ | CH₂C≡CH |
| B.259 | CH₃ | OCH₂CH₃ | CH₂C≡CH |
| B.260 | CH₃ | CN | CH₂C≡CH |
| B.261 | CF₃ | H | CH₂C≡CH |
| B.262 | CF₃ | CH₃ | CH₂C≡CH |
| B.263 | CF₃ | CH₂CH₃ | CH₂C≡CH |
| B.264 | CF₃ | CF₃ | CH₂C≡CH |
| B.265 | CF₃ | CHF₂ | CH₂C≡CH |
| B.266 | CF₃ | CH₂F | CH₂C≡CH |
| B.267 | CF₃ | Cl | CH₂C≡CH |
| B.268 | CF₃ | OCH₃ | CH₂C≡CH |
| B.269 | CF₃ | OCH₂CH₃ | CH₂C≡CH |
| B.270 | CF₃ | CN | CH₂C≡CH |
| B.271 | Cl | H | CH₂C≡CCH₃ |
| B.272 | Cl | CH₃ | CH₂C≡CCH₃ |
| B.273 | Cl | CH₂CH₃ | CH₂C≡CCH₃ |
| B.274 | Cl | CF₃ | CH₂C≡CCH₃ |
| B.275 | Cl | CHF₂ | CH₂C≡CCH₃ |
| B.276 | Cl | CH₂F | CH₂C≡CCH₃ |
| B.277 | Cl | Cl | CH₂C≡CCH₃ |
| B.278 | Cl | OCH₃ | CH₂C≡CCH₃ |
| B.279 | Cl | OCH₂CH₃ | CH₂C≡CCH₃ |
| B.280 | Cl | CN | CH₂C≡CCH₃ |
| B.281 | CH₃ | H | CH₂C≡CCH₃ |
| B.282 | CH₃ | CH₃ | CH₂C≡CCH₃ |
| B.283 | CH₃ | CH₂CH₃ | CH₂C≡CCH₃ |
| B.284 | CH₃ | CF₃ | CH₂C≡CCH₃ |
| B.285 | CH₃ | CHF₂ | CH₂C≡CCH₃ |
| B.286 | CH₃ | CH₂F | CH₂C≡CCH₃ |
| B.287 | CH₃ | Cl | CH₂C≡CCH₃ |
| B.288 | CH₃ | OCH₃ | CH₂C≡CCH₃ |
| B.289 | CH₃ | OCH₂CH₃ | CH₂C≡CCH₃ |
| B.290 | CH₃ | CN | CH₂C≡CCH₃ |
| B.291 | CF₃ | H | CH₂C≡CCH₃ |
| B.292 | CF₃ | CH₃ | CH₂C≡CCH₃ |
| B.293 | CF₃ | CH₂CH₃ | CH₂C≡CCH₃ |
| B.294 | CF₃ | CF₃ | CH₂C≡CCH₃ |
| B.295 | CF₃ | CHF₂ | CH₂C≡CCH₃ |
| B.296 | CF₃ | CH₂F | CH₂C≡CCH₃ |
| B.297 | CF₃ | Cl | CH₂C≡CCH₃ |
| B.298 | CF₃ | OCH₃ | CH₂C≡CCH₃ |
| B.299 | CF₃ | OCH₂CH₃ | CH₂C≡CCH₃ |
| B.300 | CF₃ | CN | CH₂C≡CCH₃ |
| B.301 | Cl | H | CH₂C≡C—I |
| B.302 | Cl | CH₃ | CH₂C≡C—I |
| B.303 | Cl | CH₂CH₃ | CH₂C≡C—I |
| B.304 | Cl | CF₃ | CH₂C≡C—I |
| B.305 | Cl | CHF₂ | CH₂C≡C—I |
| B.306 | Cl | CH₂F | CH₂C≡C—I |
| B.307 | Cl | Cl | CH₂C≡C—I |
| B.308 | Cl | OCH₃ | CH₂C≡C—I |
| B.309 | Cl | OCH₂CH₃ | CH₂C≡C—I |
| B.310 | Cl | CN | CH₂C≡C—I |
| B.311 | CH₃ | H | CH₂C≡C—I |
| B.312 | CH₃ | CH₃ | CH₂C≡C—I |
| B.313 | CH₃ | CH₂CH₃ | CH₂C≡C—I |
| B.314 | CH₃ | CF₃ | CH₂C≡C—I |
| B.315 | CH₃ | CHF₂ | CH₂C≡C—I |
| B.316 | CH₃ | CH₂F | CH₂C≡C—I |
| B.317 | CH₃ | Cl | CH₂C≡C—I |
| B.318 | CH₃ | OCH₃ | CH₂C≡C—I |
| B.319 | CH₃ | OCH₂CH₃ | CH₂C≡C—I |
| B.320 | CH₃ | CN | CH₂C≡C—I |
| B.321 | CF₃ | H | CH₂C≡C—I |
| B.322 | CF₃ | CH₃ | CH₂C≡C—I |
| B.323 | CF₃ | CH₂CH₃ | CH₂C≡C—I |
| B.324 | CF₃ | CF₃ | CH₂C≡C—I |
| B.325 | CF₃ | CHF₂ | CH₂C≡C—I |
| B.326 | CF₃ | CH₂F | CH₂C≡C—I |
| B.327 | CF₃ | Cl | CH₂C≡C—I |
| B.328 | CF₃ | OCH₃ | CH₂C≡C—I |
| B.329 | CF₃ | OCH₂CH₃ | CH₂C≡C—I |
| B.330 | CF₃ | CN | CH₂C≡C—I |
| B.331 | Cl | H | CH(CH₃)C≡CH |
| B.332 | Cl | CH₃ | CH(CH₃)C≡CH |
| B.333 | Cl | CH₂CH₃ | CH(CH₃)C≡CH |
| B.334 | Cl | CF₃ | CH(CH₃)C≡CH |
| B.335 | Cl | CHF₂ | CH(CH₃)C≡CH |
| B.336 | Cl | CH₂F | CH(CH₃)C≡CH |
| B.337 | Cl | Cl | CH(CH₃)C≡CH |
| B.338 | Cl | OCH₃ | CH(CH₃)C≡CH |
| B.339 | Cl | OCH₂CH₃ | CH(CH₃)C≡CH |
| B.340 | Cl | CN | CH(CH₃)C≡CH |
| B.341 | CH₃ | H | CH(CH₃)C≡CH |
| B.342 | CH₃ | CH₃ | CH(CH₃)C≡CH |
| B.343 | CH₃ | CH₂CH₃ | CH(CH₃)C≡CH |
| B.344 | CH₃ | CF₃ | CH(CH₃)C≡CH |
| B.345 | CH₃ | CHF₂ | CH(CH₃)C≡CH |
| B.346 | CH₃ | CH₂F | CH(CH₃)C≡CH |
| B.347 | CH₃ | Cl | CH(CH₃)C≡CH |
| B.348 | CH₃ | OCH₃ | CH(CH₃)C≡CH |
| B.349 | CH₃ | OCH₂CH₃ | CH(CH₃)C≡CH |
| B.350 | CH₃ | CN | CH(CH₃)C≡CH |
| B.351 | CF₃ | H | CH(CH₃)C≡CH |
| B.352 | CF₃ | CH₃ | CH(CH₃)C≡CH |
| B.353 | CF₃ | CH₂CH₃ | CH(CH₃)C≡CH |
| B.354 | CF₃ | CF₃ | CH(CH₃)C≡CH |
| B.355 | CF₃ | CHF₂ | CH(CH₃)C≡CH |
| B.356 | CF₃ | CH₂F | CH(CH₃)C≡CH |
| B.357 | CF₃ | Cl | CH(CH₃)C≡CH |
| B.358 | CF₃ | OCH₃ | CH(CH₃)C≡CH |
| B.359 | CF₃ | OCH₂CH₃ | CH(CH₃)C≡CH |
| B.360 | CF₃ | CN | CH(CH₃)C≡CH |
| B.361 | Cl | H | CH₂CH₂—O—CH₂CH₃ |
| B.362 | Cl | CH₃ | CH₂CH₂—O—CH₂CH₃ |
| B.363 | Cl | CH₂CH₃ | CH₂CH₂—O—CH₂CH₃ |
| B.364 | Cl | CF₃ | CH₂CH₂—O—CH₂CH₃ |
| B.365 | Cl | CHF₂ | CH₂CH₂—O—CH₂CH₃ |
| B.366 | Cl | CH₂F | CH₂CH₂—O—CH₂CH₃ |
| B.367 | Cl | Cl | CH₂CH₂—O—CH₂CH₃ |
| B.368 | Cl | OCH₃ | CH₂CH₂—O—CH₂CH₃ |
| B.369 | Cl | OCH₂CH₃ | CH₂CH₂—O—CH₂CH₃ |
| B.370 | Cl | CN | CH₂CH₂—O—CH₂CH₃ |
| B.371 | CH₃ | H | CH₂CH₂—O—CH₂CH₃ |
| B.372 | CH₃ | CH₃ | CH₂CH₂—O—CH₂CH₃ |
| B.373 | CH₃ | CH₂CH₃ | CH₂CH₂—O—CH₂CH₃ |
| B.374 | CH₃ | CF₃ | CH₂CH₂—O—CH₂CH₃ |
| B.375 | CH₃ | CHF₂ | CH₂CH₂—O—CH₂CH₃ |
| B.376 | CH₃ | CH₂F | CH₂CH₂—O—CH₂CH₃ |
| B.377 | CH₃ | Cl | CH₂CH₂—O—CH₂CH₃ |
| B.378 | CH₃ | OCH₃ | CH₂CH₂—O—CH₂CH₃ |
| B.379 | CH₃ | OCH₂CH₃ | CH₂CH₂—O—CH₂CH₃ |
| B.380 | CH₃ | CN | CH₂CH₂—O—CH₂CH₃ |
| B.381 | CF₃ | H | CH₂CH₂—O—CH₂CH₃ |
| B.382 | CF₃ | CH₃ | CH₂CH₂—O—CH₂CH₃ |
| B.383 | CF₃ | CH₂CH₃ | CH₂CH₂—O—CH₂CH₃ |
| B.384 | CF₃ | CF₃ | CH₂CH₂—O—CH₂CH₃ |
| B.385 | CF₃ | CHF₂ | CH₂CH₂—O—CH₂CH₃ |
| B.386 | CF₃ | CH₂F | CH₂CH₂—O—CH₂CH₃ |
| B.387 | CF₃ | Cl | CH₂CH₂—O—CH₂CH₃ |
| B.388 | CF₃ | OCH₃ | CH₂CH₂—O—CH₂CH₃ |

TABLE B-continued

| No. | R¹ | R³ | R⁴ |
|---|---|---|---|
| B.389 | CF$_3$ | OCH$_2$CH$_3$ | CH$_2$CH$_2$—O—CH$_2$CH$_3$ |
| B.390 | CF$_3$ | CN | CH$_2$CH$_2$—O—CH$_2$CH$_3$ |
| B.391 | Cl | H | CH$_2$—C$_6$H$_5$ |
| B.392 | Cl | CH$_3$ | CH$_2$—C$_6$H$_5$ |
| B.393 | Cl | CH$_2$CH$_3$ | CH$_2$—C$_6$H$_5$ |
| B.394 | Cl | CF$_3$ | CH$_2$—C$_6$H$_5$ |
| B.395 | Cl | CHF$_2$ | CH$_2$—C$_6$H$_5$ |
| B.396 | Cl | CH$_2$F | CH$_2$—C$_6$H$_5$ |
| B.397 | Cl | Cl | CH$_2$—C$_6$H$_5$ |
| B.398 | Cl | OCH$_3$ | CH$_2$—C$_6$H$_5$ |
| B.399 | Cl | OCH$_2$CH$_3$ | CH$_2$—C$_6$H$_5$ |
| B.400 | Cl | CN | CH$_2$—C$_6$H$_5$ |
| B.401 | CH$_3$ | H | CH$_2$—C$_6$H$_5$ |
| B.402 | CH$_3$ | CH$_3$ | CH$_2$—C$_6$H$_5$ |
| B.403 | CH$_3$ | CH$_2$CH$_3$ | CH$_2$—C$_6$H$_5$ |
| B.404 | CH$_3$ | CF$_3$ | CH$_2$—C$_6$H$_5$ |
| B.405 | CH$_3$ | CHF$_2$ | CH$_2$—C$_6$H$_5$ |
| B.406 | CH$_3$ | CH$_2$F | CH$_2$—C$_6$H$_5$ |
| B.407 | CH$_3$ | Cl | CH$_2$—C$_6$H$_5$ |
| B.408 | CH$_3$ | OCH$_3$ | CH$_2$—C$_6$H$_5$ |
| B.409 | CH$_3$ | OCH$_2$CH$_3$ | CH$_2$—C$_6$H$_5$ |
| B.410 | CH$_3$ | CN | CH$_2$—C$_6$H$_5$ |
| B.411 | CF$_3$ | H | CH$_2$—C$_6$H$_5$ |
| B.412 | CF$_3$ | CH$_3$ | CH$_2$—C$_6$H$_5$ |
| B.413 | CF$_3$ | CH$_2$CH$_3$ | CH$_2$—C$_6$H$_5$ |
| B.414 | CF$_3$ | CF$_3$ | CH$_2$—C$_6$H$_5$ |
| B.415 | CF$_3$ | CHF$_2$ | CH$_2$—C$_6$H$_5$ |
| B.416 | CF$_3$ | CH$_2$F | CH$_2$—C$_6$H$_5$ |
| B.417 | CF$_3$ | Cl | CH$_2$—C$_6$H$_5$ |
| B.418 | CF$_3$ | OCH$_3$ | CH$_2$—C$_6$H$_5$ |
| B.419 | CF$_3$ | OCH$_2$CH$_3$ | CH$_2$—C$_6$H$_5$ |
| B.420 | CF$_3$ | CN | CH$_2$—C$_6$H$_5$ |
| B.421 | Cl | H | cyclopropyl |
| B.422 | Cl | CH$_3$ | cyclopropyl |
| B.423 | Cl | CH$_2$CH$_3$ | cyclopropyl |
| B.424 | Cl | CF$_3$ | cyclopropyl |
| B.425 | Cl | CHF$_2$ | cyclopropyl |
| B.426 | Cl | CH$_2$F | cyclopropyl |
| B.427 | Cl | Cl | cyclopropyl |
| B.428 | Cl | OCH$_3$ | cyclopropyl |
| B.429 | Cl | OCH$_2$CH$_3$ | cyclopropyl |
| B.430 | Cl | CN | cyclopropyl |
| B.431 | CH$_3$ | H | cyclopropyl |
| B.432 | CH$_3$ | CH$_3$ | cyclopropyl |
| B.433 | CH$_3$ | CH$_2$CH$_3$ | cyclopropyl |
| B.434 | CH$_3$ | CF$_3$ | cyclopropyl |
| B.435 | CH$_3$ | CHF$_2$ | cyclopropyl |
| B.436 | CH$_3$ | CH$_2$F | cyclopropyl |
| B.437 | CH$_3$ | Cl | cyclopropyl |
| B.438 | CH$_3$ | OCH$_3$ | cyclopropyl |
| B.439 | CH$_3$ | OCH$_2$CH$_3$ | cyclopropyl |
| B.440 | CH$_3$ | CN | cyclopropyl |
| B.441 | CF$_3$ | H | cyclopropyl |
| B.442 | CF$_3$ | CH$_3$ | cyclopropyl |
| B.443 | CF$_3$ | CH$_2$CH$_3$ | cyclopropyl |
| B.444 | CF$_3$ | CF$_3$ | cyclopropyl |
| B.445 | CF$_3$ | CHF$_2$ | cyclopropyl |
| B.446 | CF$_3$ | CH$_2$F | cyclopropyl |
| B.447 | CF$_3$ | Cl | cyclopropyl |
| B.448 | CF$_3$ | OCH$_3$ | cyclopropyl |
| B.449 | CF$_3$ | OCH$_2$CH$_3$ | cyclopropyl |
| B.450 | CF$_3$ | CN | cyclopropyl |
| B.451 | Cl | H | CH$_2$-(2,2-Cl$_2$-cyclopropyl) |
| B.452 | Cl | CH$_3$ | CH$_2$-(2,2-Cl$_2$-cyclopropyl) |
| B.453 | Cl | CH$_2$CH$_3$ | CH$_2$-(2,2-Cl$_2$-cyclopropyl) |
| B.454 | Cl | CF$_3$ | CH$_2$-(2,2-Cl$_2$-cyclopropyl) |
| B.455 | Cl | CHF$_2$ | CH$_2$-(2,2-Cl$_2$-cyclopropyl) |
| B.456 | Cl | CH$_2$F | CH$_2$-(2,2-Cl$_2$-cyclopropyl) |
| B.457 | Cl | Cl | CH$_2$-(2,2-Cl$_2$-cyclopropyl) |
| B.458 | Cl | OCH$_3$ | CH$_2$-(2,2-Cl$_2$-cyclopropyl) |
| B.459 | Cl | OCH$_2$CH$_3$ | CH$_2$-(2,2-Cl$_2$-cyclopropyl) |
| B.460 | Cl | CN | CH$_2$-(2,2-Cl$_2$-cyclopropyl) |
| B.461 | CH$_3$ | H | CH$_2$-(2,2-Cl$_2$-cyclopropyl) |
| B.462 | CH$_3$ | CH$_3$ | CH$_2$-(2,2-Cl$_2$-cyclopropyl) |
| B.463 | CH$_3$ | CH$_2$CH$_3$ | CH$_2$-(2,2-Cl$_2$-cyclopropyl) |
| B.464 | CH$_3$ | CF$_3$ | CH$_2$-(2,2-Cl$_2$-cyclopropyl) |
| B.465 | CH$_3$ | CHF$_2$ | CH$_2$-(2,2-Cl$_2$-cyclopropyl) |
| B.466 | CH$_3$ | CH$_2$F | CH$_2$-(2,2-Cl$_2$-cyclopropyl) |
| B.467 | CH$_3$ | Cl | CH$_2$-(2,2-Cl$_2$-cyclopropyl) |
| B.468 | CH$_3$ | OCH$_3$ | CH$_2$-(2,2-Cl$_2$-cyclopropyl) |
| B.469 | CH$_3$ | OCH$_2$CH$_3$ | CH$_2$-(2,2-Cl$_2$-cyclopropyl) |
| B.470 | CH$_3$ | CN | CH$_2$-(2,2-Cl$_2$-cyclopropyl) |
| B.471 | CF$_3$ | H | CH$_2$-(2,2-Cl$_2$-cyclopropyl) |
| B.472 | CF$_3$ | CH$_3$ | CH$_2$-(2,2-Cl$_2$-cyclopropyl) |
| B.473 | CF$_3$ | CH$_2$CH$_3$ | CH$_2$-(2,2-Cl$_2$-cyclopropyl) |
| B.474 | CF$_3$ | CF$_3$ | CH$_2$-(2,2-Cl$_2$-cyclopropyl) |
| B.475 | CF$_3$ | CHF$_2$ | CH$_2$-(2,2-Cl$_2$-cyclopropyl) |
| B.476 | CF$_3$ | CH$_2$F | CH$_2$-(2,2-Cl$_2$-cyclopropyl) |
| B.477 | CF$_3$ | Cl | CH$_2$-(2,2-Cl$_2$-cyclopropyl) |
| B.478 | CF$_3$ | OCH$_3$ | CH$_2$-(2,2-Cl$_2$-cyclopropyl) |
| B.479 | CF$_3$ | OCH$_2$CH$_3$ | CH$_2$-(2,2-Cl$_2$-cyclopropyl) |
| B.480 | CF$_3$ | CN | CH$_2$-(2,2-Cl$_2$-cyclopropyl) |
| B.481 | H | CH$_3$ | H |
| B.482 | H | CH$_2$CH$_3$ | H |
| B.483 | H | CF$_3$ | H |
| B.484 | H | Cl | H |
| B.485 | H | OCH$_3$ | H |
| B.486 | CH$_2$CH$_3$ | CH$_3$ | H |
| B.487 | CH$_2$CH$_3$ | CH$_2$CH$_3$ | H |
| B.488 | CH$_2$CH$_3$ | CF$_3$ | H |
| B.489 | CH$_2$CH$_3$ | Cl | H |
| B.490 | CH$_2$CH$_3$ | OCH$_3$ | H |
| B.491 | CHF$_2$ | CH$_3$ | H |
| B.492 | CHF$_2$ | CH$_2$CH$_3$ | H |
| B.493 | CHF$_2$ | CF$_3$ | H |
| B.494 | CHF$_2$ | Cl | H |
| B.495 | CHF$_2$ | OCH$_3$ | H |
| B.496 | CH$_2$F | CH$_3$ | H |
| B.497 | CH$_2$F | CH$_2$CH$_3$ | H |
| B.498 | CH$_2$F | CF$_3$ | H |
| B.499 | CH$_2$F | Cl | H |
| B.500 | CH$_2$F | OCH$_3$ | H |
| B.501 | OCH$_3$ | CH$_3$ | H |
| B.502 | OCH$_3$ | CH$_2$CH$_3$ | H |
| B.503 | OCH$_3$ | CF$_3$ | H |
| B.504 | OCH$_3$ | Cl | H |
| B.505 | OCH$_3$ | OCH$_3$ | H |
| B.506 | OCH$_2$CH$_3$ | CH$_3$ | H |
| B.507 | OCH$_2$CH$_3$ | CH$_2$CH$_3$ | H |
| B.508 | OCH$_2$CH$_3$ | CF$_3$ | H |
| B.509 | OCH$_2$CH$_3$ | Cl | H |
| B.510 | OCH$_2$CH$_3$ | OCH$_3$ | H |
| B.511 | CN | CH$_3$ | H |
| B.512 | CN | CH$_2$CH$_3$ | H |
| B.513 | CN | CF$_3$ | H |
| B.514 | CN | Cl | H |
| B.515 | CN | OCH$_3$ | H |
| B.516 | H | CH$_3$ | CH$_3$ |
| B.517 | H | CH$_2$CH$_3$ | CH$_3$ |
| B.518 | H | CF$_3$ | CH$_3$ |
| B.519 | H | Cl | CH$_3$ |
| B.520 | H | OCH$_3$ | CH$_3$ |
| B.521 | CH$_2$CH$_3$ | CH$_3$ | CH$_3$ |
| B.522 | CH$_2$CH$_3$ | CH$_2$CH$_3$ | CH$_3$ |
| B.523 | CH$_2$CH$_3$ | CF$_3$ | CH$_3$ |
| B.524 | CH$_2$CH$_3$ | Cl | CH$_3$ |
| B.525 | CH$_2$CH$_3$ | OCH$_3$ | CH$_3$ |
| B.526 | CHF$_2$ | CH$_3$ | CH$_3$ |
| B.527 | CHF$_2$ | CH$_2$CH$_3$ | CH$_3$ |
| B.528 | CHF$_2$ | CF$_3$ | CH$_3$ |
| B.529 | CHF$_2$ | Cl | CH$_3$ |
| B.530 | CHF$_2$ | OCH$_3$ | CH$_3$ |
| B.531 | CH$_2$F | CH$_3$ | CH$_3$ |
| B.532 | CH$_2$F | CH$_2$CH$_3$ | CH$_3$ |
| B.533 | CH$_2$F | CF$_3$ | CH$_3$ |
| B.534 | CH$_2$F | Cl | CH$_3$ |
| B.535 | CH$_2$F | OCH$_3$ | CH$_3$ |
| B.536 | OCH$_3$ | CH$_3$ | CH$_3$ |
| B.537 | OCH$_3$ | CH$_2$CH$_3$ | CH$_3$ |
| B.538 | OCH$_3$ | CF$_3$ | CH$_3$ |
| B.539 | OCH$_3$ | Cl | CH$_3$ |
| B.540 | OCH$_3$ | OCH$_3$ | CH$_3$ |
| B.541 | OCH$_2$CH$_3$ | CH$_3$ | CH$_3$ |
| B.542 | OCH$_2$CH$_3$ | CH$_2$CH$_3$ | CH$_3$ |

TABLE B-continued

| No. | R$^1$ | R$^3$ | R$^4$ |
|---|---|---|---|
| B.543 | OCH$_2$CH$_3$ | CF$_3$ | CH$_3$ |
| B.544 | OCH$_2$CH$_3$ | Cl | CH$_3$ |
| B.545 | OCH$_2$CH$_3$ | OCH$_3$ | CH$_3$ |
| B.546 | CN | CH$_3$ | CH$_3$ |
| B.547 | CN | CH$_2$CH$_3$ | CH$_3$ |
| B.548 | CN | CF$_3$ | CH$_3$ |
| B.549 | CN | Cl | CH$_3$ |
| B.550 | CN | OCH$_3$ | CH$_3$ |
| B.551 | H | CH$_3$ | CH$_2$CH$_3$ |
| B.552 | H | CH$_2$CH$_3$ | CH$_2$CH$_3$ |
| B.553 | H | CF$_3$ | CH$_2$CH$_3$ |
| B.554 | H | Cl | CH$_2$CH$_3$ |
| B.555 | H | OCH$_3$ | CH$_2$CH$_3$ |
| B.556 | CH$_2$CH$_3$ | CH$_3$ | CH$_2$CH$_3$ |
| B.557 | CH$_2$CH$_3$ | CH$_2$CH$_3$ | CH$_2$CH$_3$ |
| B.558 | CH$_2$CH$_3$ | CF$_3$ | CH$_2$CH$_3$ |
| B.559 | CH$_2$CH$_3$ | Cl | CH$_2$CH$_3$ |
| B.560 | CH$_2$CH$_3$ | OCH$_3$ | CH$_2$CH$_3$ |
| B.561 | CHF$_2$ | CH$_3$ | CH$_2$CH$_3$ |
| B.562 | CHF$_2$ | CH$_2$CH$_3$ | CH$_2$CH$_3$ |
| B.563 | CHF$_2$ | CF$_3$ | CH$_2$CH$_3$ |
| B.564 | CHF$_2$ | Cl | CH$_2$CH$_3$ |
| B.565 | CHF$_2$ | OCH$_3$ | CH$_2$CH$_3$ |
| B.566 | CH$_2$F | CH$_3$ | CH$_2$CH$_3$ |
| B.567 | CH$_2$F | CH$_2$CH$_3$ | CH$_2$CH$_3$ |
| B.568 | CH$_2$F | CF$_3$ | CH$_2$CH$_3$ |
| B.569 | CH$_2$F | Cl | CH$_2$CH$_3$ |
| B.570 | CH$_2$F | OCH$_3$ | CH$_2$CH$_3$ |
| B.571 | OCH$_3$ | CH$_3$ | CH$_2$CH$_3$ |
| B.572 | OCH$_3$ | CH$_2$CH$_3$ | CH$_2$CH$_3$ |
| B.573 | OCH$_3$ | CF$_3$ | CH$_2$CH$_3$ |
| B.574 | OCH$_3$ | Cl | CH$_2$CH$_3$ |
| B.575 | OCH$_3$ | OCH$_3$ | CH$_2$CH$_3$ |
| B.576 | OCH$_2$CH$_3$ | CH$_3$ | CH$_2$CH$_3$ |
| B.577 | OCH$_2$CH$_3$ | CH$_2$CH$_3$ | CH$_2$CH$_3$ |
| B.578 | OCH$_2$CH$_3$ | CF$_3$ | CH$_2$CH$_3$ |
| B.579 | OCH$_2$CH$_3$ | Cl | CH$_2$CH$_3$ |
| B.580 | OCH$_2$CH$_3$ | OCH$_3$ | CH$_2$CH$_3$ |
| B.581 | CN | CH$_3$ | CH$_2$CH$_3$ |
| B.582 | CN | CH$_2$CH$_3$ | CH$_2$CH$_3$ |
| B.583 | CN | CF$_3$ | CH$_2$CH$_3$ |
| B.584 | CN | Cl | CH$_2$CH$_3$ |
| B.585 | CN | OCH$_3$ | CH$_2$CH$_3$ |
| B.586 | H | CH$_3$ | CH$_2$CH$_2$CH$_3$ |
| B.587 | H | CH$_2$CH$_3$ | CH$_2$CH$_2$CH$_3$ |
| B.588 | H | CF$_3$ | CH$_2$CH$_2$CH$_3$ |
| B.589 | H | Cl | CH$_2$CH$_2$CH$_3$ |
| B.590 | H | OCH$_3$ | CH$_2$CH$_2$CH$_3$ |
| B.591 | CH$_2$CH$_3$ | CH$_3$ | CH$_2$CH$_2$CH$_3$ |
| B.592 | CH$_2$CH$_3$ | CH$_2$CH$_3$ | CH$_2$CH$_2$CH$_3$ |
| B.593 | CH$_2$CH$_3$ | CF$_3$ | CH$_2$CH$_2$CH$_3$ |
| B.594 | CH$_2$CH$_3$ | Cl | CH$_2$CH$_2$CH$_3$ |
| B.595 | CH$_2$CH$_3$ | OCH$_3$ | CH$_2$CH$_2$CH$_3$ |
| B.596 | CHF$_2$ | CH$_3$ | CH$_2$CH$_2$CH$_3$ |
| B.597 | CHF$_2$ | CH$_2$CH$_3$ | CH$_2$CH$_2$CH$_3$ |
| B.598 | CHF$_2$ | CF$_3$ | CH$_2$CH$_2$CH$_3$ |
| B.599 | CHF$_2$ | Cl | CH$_2$CH$_2$CH$_3$ |
| B.600 | CHF$_2$ | OCH$_3$ | CH$_2$CH$_2$CH$_3$ |
| B.601 | CH$_2$F | CH$_3$ | CH$_2$CH$_2$CH$_3$ |
| B.602 | CH$_2$F | CH$_2$CH$_3$ | CH$_2$CH$_2$CH$_3$ |
| B.603 | CH$_2$F | CF$_3$ | CH$_2$CH$_2$CH$_3$ |
| B.604 | CH$_2$F | Cl | CH$_2$CH$_2$CH$_3$ |
| B.605 | CH$_2$F | OCH$_3$ | CH$_2$CH$_2$CH$_3$ |
| B.606 | OCH$_3$ | CH$_3$ | CH$_2$CH$_2$CH$_3$ |
| B.607 | OCH$_3$ | CH$_2$CH$_3$ | CH$_2$CH$_2$CH$_3$ |
| B.608 | OCH$_3$ | CF$_3$ | CH$_2$CH$_2$CH$_3$ |
| B.609 | OCH$_3$ | Cl | CH$_2$CH$_2$CH$_3$ |
| B.610 | OCH$_3$ | OCH$_3$ | CH$_2$CH$_2$CH$_3$ |
| B.611 | OCH$_2$CH$_3$ | CH$_3$ | CH$_2$CH$_2$CH$_3$ |
| B.612 | OCH$_2$CH$_3$ | CH$_2$CH$_3$ | CH$_2$CH$_2$CH$_3$ |
| B.613 | OCH$_2$CH$_3$ | CF$_3$ | CH$_2$CH$_2$CH$_3$ |
| B.614 | OCH$_2$CH$_3$ | Cl | CH$_2$CH$_2$CH$_3$ |
| B.615 | OCH$_2$CH$_3$ | OCH$_3$ | CH$_2$CH$_2$CH$_3$ |
| B.616 | CN | CH$_3$ | CH$_2$CH$_2$CH$_3$ |
| B.617 | CN | CH$_2$CH$_3$ | CH$_2$CH$_2$CH$_3$ |
| B.618 | CN | CF$_3$ | CH$_2$CH$_2$CH$_3$ |
| B.619 | CN | Cl | CH$_2$CH$_2$CH$_3$ |
| B.620 | CN | OCH$_3$ | CH$_2$CH$_2$CH$_3$ |
| B.621 | H | CH$_3$ | CH(CH$_3$)$_2$ |
| B.622 | H | CH$_2$CH$_3$ | CH(CH$_3$)$_2$ |
| B.623 | H | CF$_3$ | CH(CH$_3$)$_2$ |
| B.624 | H | Cl | CH(CH$_3$)$_2$ |
| B.625 | H | OCH$_3$ | CH(CH$_3$)$_2$ |
| B.626 | CH$_2$CH$_3$ | CH$_3$ | CH(CH$_3$)$_2$ |
| B.627 | CH$_2$CH$_3$ | CH$_2$CH$_3$ | CH(CH$_3$)$_2$ |
| B.628 | CH$_2$CH$_3$ | CF$_3$ | CH(CH$_3$)$_2$ |
| B.629 | CH$_2$CH$_3$ | Cl | CH(CH$_3$)$_2$ |
| B.630 | CH$_2$CH$_3$ | OCH$_3$ | CH(CH$_3$)$_2$ |
| B.631 | CHF$_2$ | CH$_3$ | CH(CH$_3$)$_2$ |
| B.632 | CHF$_2$ | CH$_2$CH$_3$ | CH(CH$_3$)$_2$ |
| B.633 | CHF$_2$ | CF$_3$ | CH(CH$_3$)$_2$ |
| B.634 | CHF$_2$ | Cl | CH(CH$_3$)$_2$ |
| B.635 | CHF$_2$ | OCH$_3$ | CH(CH$_3$)$_2$ |
| B.636 | CH$_2$F | CH$_3$ | CH(CH$_3$)$_2$ |
| B.637 | CH$_2$F | CH$_2$CH$_3$ | CH(CH$_3$)$_2$ |
| B.638 | CH$_2$F | CF$_3$ | CH(CH$_3$)$_2$ |
| B.639 | CH$_2$F | Cl | CH(CH$_3$)$_2$ |
| B.640 | CH$_2$F | OCH$_3$ | CH(CH$_3$)$_2$ |
| B.641 | OCH$_3$ | CH$_3$ | CH(CH$_3$)$_2$ |
| B.642 | OCH$_3$ | CH$_2$CH$_3$ | CH(CH$_3$)$_2$ |
| B.643 | OCH$_3$ | CF$_3$ | CH(CH$_3$)$_2$ |
| B.644 | OCH$_3$ | Cl | CH(CH$_3$)$_2$ |
| B.645 | OCH$_3$ | OCH$_3$ | CH(CH$_3$)$_2$ |
| B.646 | OCH$_2$CH$_3$ | CH$_3$ | CH(CH$_3$)$_2$ |
| B.647 | OCH$_2$CH$_3$ | CH$_2$CH$_3$ | CH(CH$_3$)$_2$ |
| B.648 | OCH$_2$CH$_3$ | CF$_3$ | CH(CH$_3$)$_2$ |
| B.649 | OCH$_2$CH$_3$ | Cl | CH(CH$_3$)$_2$ |
| B.650 | OCH$_2$CH$_3$ | OCH$_3$ | CH(CH$_3$)$_2$ |
| B.651 | CN | CH$_3$ | CH(CH$_3$)$_2$ |
| B.652 | CN | CH$_2$CH$_3$ | CH(CH$_3$)$_2$ |
| B.653 | CN | CF$_3$ | CH(CH$_3$)$_2$ |
| B.654 | CN | Cl | CH(CH$_3$)$_2$ |
| B.655 | CN | OCH$_3$ | CH(CH$_3$)$_2$ |
| B.656 | H | CH$_3$ | CH$_2$CH=CH$_2$ |
| B.657 | H | CH$_2$CH$_3$ | CH$_2$CH=CH$_2$ |
| B.658 | H | CF$_3$ | CH$_2$CH=CH$_2$ |
| B.659 | H | Cl | CH$_2$CH=CH$_2$ |
| B.660 | H | OCH$_3$ | CH$_2$CH=CH$_2$ |
| B.661 | CH$_2$CH$_3$ | CH$_3$ | CH$_2$CH=CH$_2$ |
| B.662 | CH$_2$CH$_3$ | CH$_2$CH$_3$ | CH$_2$CH=CH$_2$ |
| B.663 | CH$_2$CH$_3$ | CF$_3$ | CH$_2$CH=CH$_2$ |
| B.664 | CH$_2$CH$_3$ | Cl | CH$_2$CH=CH$_2$ |
| B.665 | CH$_2$CH$_3$ | OCH$_3$ | CH$_2$CH=CH$_2$ |
| B.666 | CHF$_2$ | CH$_3$ | CH$_2$CH=CH$_2$ |
| B.667 | CHF$_2$ | CH$_2$CH$_3$ | CH$_2$CH=CH$_2$ |
| B.668 | CHF$_2$ | CF$_3$ | CH$_2$CH=CH$_2$ |
| B.669 | CHF$_2$ | Cl | CH$_2$CH=CH$_2$ |
| B.670 | CHF$_2$ | OCH$_3$ | CH$_2$CH=CH$_2$ |
| B.671 | CH$_2$F | CH$_3$ | CH$_2$CH=CH$_2$ |
| B.672 | CH$_2$F | CH$_2$CH$_3$ | CH$_2$CH=CH$_2$ |
| B.673 | CH$_2$F | CF$_3$ | CH$_2$CH=CH$_2$ |
| B.674 | CH$_2$F | Cl | CH$_2$CH=CH$_2$ |
| B.675 | CH$_2$F | OCH$_3$ | CH$_2$CH=CH$_2$ |
| B.676 | OCH$_3$ | CH$_3$ | CH$_2$CH=CH$_2$ |
| B.677 | OCH$_3$ | CH$_2$CH$_3$ | CH$_2$CH=CH$_2$ |
| B.678 | OCH$_3$ | CF$_3$ | CH$_2$CH=CH$_2$ |
| B.679 | OCH$_3$ | Cl | CH$_2$CH=CH$_2$ |
| B.680 | OCH$_3$ | OCH$_3$ | CH$_2$CH=CH$_2$ |
| B.681 | OCH$_2$CH$_3$ | CH$_3$ | CH$_2$CH=CH$_2$ |
| B.682 | OCH$_2$CH$_3$ | CH$_2$CH$_3$ | CH$_2$CH=CH$_2$ |
| B.683 | OCH$_2$CH$_3$ | CF$_3$ | CH$_2$CH=CH$_2$ |
| B.684 | OCH$_2$CH$_3$ | Cl | CH$_2$CH=CH$_2$ |
| B.685 | OCH$_2$CH$_3$ | OCH$_3$ | CH$_2$CH=CH$_2$ |
| B.686 | CN | CH$_3$ | CH$_2$CH=CH$_2$ |
| B.687 | CN | CH$_2$CH$_3$ | CH$_2$CH=CH$_2$ |
| B.688 | CN | CF$_3$ | CH$_2$CH=CH$_2$ |
| B.689 | CN | Cl | CH$_2$CH=CH$_2$ |
| B.690 | CN | OCH$_3$ | CH$_2$CH=CH$_2$ |
| B.691 | H | CH$_3$ | CH$_2$CH=CH—Cl (trans) |
| B.692 | H | CH$_2$CH$_3$ | CH$_2$CH=CH—Cl (trans) |
| B.693 | H | CF$_3$ | CH$_2$CH=CH—Cl (trans) |
| B.694 | H | Cl | CH$_2$CH=CH—Cl (trans) |
| B.695 | H | OCH$_3$ | CH$_2$CH=CH—Cl (trans) |
| B.696 | CH$_2$CH$_3$ | CH$_3$ | CH$_2$CH=CH—Cl (trans) |

TABLE B-continued

| No. | R¹ | R³ | R⁴ |
|---|---|---|---|
| B.697 | CH$_2$CH$_3$ | CH$_2$CH$_3$ | CH$_2$CH=CH—Cl (trans) |
| B.698 | CH$_2$CH$_3$ | CF$_3$ | CH$_2$CH=CH—Cl (trans) |
| B.699 | CH$_2$CH$_3$ | Cl | CH$_2$CH=CH—Cl (trans) |
| B.700 | CH$_2$CH$_3$ | OCH$_3$ | CH$_2$CH=CH—Cl (trans) |
| B.701 | CHF$_2$ | CH$_3$ | CH$_2$CH=CH—Cl (trans) |
| B.702 | CHF$_2$ | CH$_2$CH$_3$ | CH$_2$CH=CH—Cl (trans) |
| B.703 | CHF$_2$ | CF$_3$ | CH$_2$CH=CH—Cl (trans) |
| B.704 | CHF$_2$ | Cl | CH$_2$CH=CH—Cl (trans) |
| B.705 | CHF$_2$ | OCH$_3$ | CH$_2$CH=CH—Cl (trans) |
| B.706 | CH$_2$F | CH$_3$ | CH$_2$CH=CH—Cl (trans) |
| B.707 | CH$_2$F | CH$_2$CH$_3$ | CH$_2$CH=CH—Cl (trans) |
| B.708 | CH$_2$F | CF$_3$ | CH$_2$CH=CH—Cl (trans) |
| B.709 | CH$_2$F | Cl | CH$_2$CH=CH—Cl (trans) |
| B.710 | CH$_2$F | OCH$_3$ | CH$_2$CH=CH—Cl (trans) |
| B.711 | OCH$_3$ | CH$_3$ | CH$_2$CH=CH—Cl (trans) |
| B.712 | OCH$_3$ | CH$_2$CH$_3$ | CH$_2$CH=CH—Cl (trans) |
| B.713 | OCH$_3$ | CF$_3$ | CH$_2$CH=CH—Cl (trans) |
| B.714 | OCH$_3$ | Cl | CH$_2$CH=CH—Cl (trans) |
| B.715 | OCH$_3$ | OCH$_3$ | CH$_2$CH=CH—Cl (trans) |
| B.716 | OCH$_2$CH$_3$ | CH$_3$ | CH$_2$CH=CH—Cl (trans) |
| B.717 | OCH$_2$CH$_3$ | CH$_2$CH$_3$ | CH$_2$CH=CH—Cl (trans) |
| B.718 | OCH$_2$CH$_3$ | CF$_3$ | CH$_2$CH=CH—Cl (trans) |
| B.719 | OCH$_2$CH$_3$ | Cl | CH$_2$CH=CH—Cl (trans) |
| B.720 | OCH$_2$CH$_3$ | OCH$_3$ | CH$_2$CH=CH—Cl (trans) |
| B.721 | CN | CH$_3$ | CH$_2$CH=CH—Cl (trans) |
| B.722 | CN | CH$_2$CH$_3$ | CH$_2$CH=CH—Cl (trans) |
| B.723 | CN | CF$_3$ | CH$_2$CH=CH—Cl (trans) |
| B.724 | CN | Cl | CH$_2$CH=CH—Cl (trans) |
| B.725 | CN | OCH$_3$ | CH$_2$CH=CH—Cl (trans) |
| B.726 | H | CH$_3$ | CH$_2$CCl=CH$_2$ |
| B.727 | H | CH$_2$CH$_3$ | CH$_2$CCl=CH$_2$ |
| B.728 | H | CF$_3$ | CH$_2$CCl=CH$_2$ |
| B.729 | H | Cl | CH$_2$CCl=CH$_2$ |
| B.730 | H | OCH$_3$ | CH$_2$CCl=CH$_2$ |
| B.731 | CH$_2$CH$_3$ | CH$_3$ | CH$_2$CCl=CH$_2$ |
| B.732 | CH$_2$CH$_3$ | CH$_2$CH$_3$ | CH$_2$CCl=CH$_2$ |
| B.733 | CH$_2$CH$_3$ | CF$_3$ | CH$_2$CCl=CH$_2$ |
| B.734 | CH$_2$CH$_3$ | Cl | CH$_2$CCl=CH$_2$ |
| B.735 | CH$_2$CH$_3$ | OCH$_3$ | CH$_2$CCl=CH$_2$ |
| B.736 | CHF$_2$ | CH$_3$ | CH$_2$CCl=CH$_2$ |
| B.737 | CHF$_2$ | CH$_2$CH$_3$ | CH$_2$CCl=CH$_2$ |
| B.738 | CHF$_2$ | CF$_3$ | CH$_2$CCl=CH$_2$ |
| B.739 | CHF$_2$ | Cl | CH$_2$CCl=CH$_2$ |
| B.740 | CHF$_2$ | OCH$_3$ | CH$_2$CCl=CH$_2$ |
| B.741 | CH$_2$F | CH$_3$ | CH$_2$CCl=CH$_2$ |
| B.742 | CH$_2$F | CH$_2$CH$_3$ | CH$_2$CCl=CH$_2$ |
| B.743 | CH$_2$F | CF$_3$ | CH$_2$CCl=CH$_2$ |
| B.744 | CH$_2$F | Cl | CH$_2$CCl=CH$_2$ |
| B.745 | CH$_2$F | OCH$_3$ | CH$_2$CCl=CH$_2$ |
| B.746 | OCH$_3$ | CH$_3$ | CH$_2$CCl=CH$_2$ |
| B.747 | OCH$_3$ | CH$_2$CH$_3$ | CH$_2$CCl=CH$_2$ |
| B.748 | OCH$_3$ | CF$_3$ | CH$_2$CCl=CH$_2$ |
| B.749 | OCH$_3$ | Cl | CH$_2$CCl=CH$_2$ |
| B.750 | OCH$_3$ | OCH$_3$ | CH$_2$CCl=CH$_2$ |
| B.751 | OCH$_2$CH$_3$ | CH$_3$ | CH$_2$CCl=CH$_2$ |
| B.752 | OCH$_2$CH$_3$ | CH$_2$CH$_3$ | CH$_2$CCl=CH$_2$ |
| B.753 | OCH$_2$CH$_3$ | CF$_3$ | CH$_2$CCl=CH$_2$ |
| B.754 | OCH$_2$CH$_3$ | Cl | CH$_2$CCl=CH$_2$ |
| B.755 | OCH$_2$CH$_3$ | OCH$_3$ | CH$_2$CCl=CH$_2$ |
| B.756 | CN | CH$_3$ | CH$_2$CCl=CH$_2$ |
| B.757 | CN | CH$_2$CH$_3$ | CH$_2$CCl=CH$_2$ |
| B.758 | CN | CF$_3$ | CH$_2$CCl=CH$_2$ |
| B.759 | CN | Cl | CH$_2$CCl=CH$_2$ |
| B.760 | CN | OCH$_3$ | CH$_2$CCl=CH$_2$ |
| B.761 | H | CH$_3$ | CH$_2$C≡CH |
| B.762 | H | CH$_2$CH$_3$ | CH$_2$C≡CH |
| B.763 | H | CF$_3$ | CH$_2$C≡CH |
| B.764 | H | Cl | CH$_2$C≡CH |
| B.765 | H | OCH$_3$ | CH$_2$C≡CH |
| B.766 | CH$_2$CH$_3$ | CH$_3$ | CH$_2$C≡CH |
| B.767 | CH$_2$CH$_3$ | CH$_2$CH$_3$ | CH$_2$C≡CH |
| B.768 | CH$_2$CH$_3$ | CF$_3$ | CH$_2$C≡CH |
| B.769 | CH$_2$CH$_3$ | Cl | CH$_2$C≡CH |
| B.770 | CH$_2$CH$_3$ | OCH$_3$ | CH$_2$C≡CH |
| B.771 | CHF$_2$ | CH$_3$ | CH$_2$C≡CH |
| B.772 | CHF$_2$ | CH$_2$CH$_3$ | CH$_2$C≡CH |
| B.773 | CHF$_2$ | CF$_3$ | CH$_2$C≡CH |
| B.774 | CHF$_2$ | Cl | CH$_2$C≡CH |
| B.775 | CHF$_2$ | OCH$_3$ | CH$_2$C≡CH |
| B.776 | CH$_2$F | CH$_3$ | CH$_2$C≡CH |
| B.777 | CH$_2$F | CH$_2$CH$_3$ | CH$_2$C≡CH |
| B.778 | CH$_2$F | CF$_3$ | CH$_2$C≡CH |
| B.779 | CH$_2$F | Cl | CH$_2$C≡CH |
| B.780 | CH$_2$F | OCH$_3$ | CH$_2$C≡CH |
| B.781 | OCH$_3$ | CH$_3$ | CH$_2$C≡CH |
| B.782 | OCH$_3$ | CH$_2$CH$_3$ | CH$_2$C≡CH |
| B.783 | OCH$_3$ | CF$_3$ | CH$_2$C≡CH |
| B.784 | OCH$_3$ | Cl | CH$_2$C≡CH |
| B.785 | OCH$_3$ | OCH$_3$ | CH$_2$C≡CH |
| B.786 | OCH$_2$CH$_3$ | CH$_3$ | CH$_2$C≡CH |
| B.787 | OCH$_2$CH$_3$ | CH$_2$CH$_3$ | CH$_2$C≡CH |
| B.788 | OCH$_2$CH$_3$ | CF$_3$ | CH$_2$C≡CH |
| B.789 | OCH$_2$CH$_3$ | Cl | CH$_2$C≡CH |
| B.790 | OCH$_2$CH$_3$ | OCH$_3$ | CH$_2$C≡CH |
| B.791 | CN | CH$_3$ | CH$_2$C≡CH |
| B.792 | CN | CH$_2$CH$_3$ | CH$_2$C≡CH |
| B.793 | CN | CF$_3$ | CH$_2$C≡CH |
| B.794 | CN | Cl | CH$_2$C≡CH |
| B.795 | CN | OCH$_3$ | CH$_2$C≡CH |
| B.796 | H | CH$_3$ | CH$_2$C≡CCH$_3$ |
| B.797 | H | CH$_2$CH$_3$ | CH$_2$C≡CCH$_3$ |
| B.798 | H | CF$_3$ | CH$_2$C≡CCH$_3$ |
| B.799 | H | Cl | CH$_2$C≡CCH$_3$ |
| B.800 | H | OCH$_3$ | CH$_2$C≡CCH$_3$ |
| B.801 | CH$_2$CH$_3$ | CH$_3$ | CH$_2$C≡CCH$_3$ |
| B.802 | CH$_2$CH$_3$ | CH$_2$CH$_3$ | CH$_2$C≡CCH$_3$ |
| B.803 | CH$_2$CH$_3$ | CF$_3$ | CH$_2$C≡CCH$_3$ |
| B.804 | CH$_2$CH$_3$ | Cl | CH$_2$C≡CCH$_3$ |
| B.805 | CH$_2$CH$_3$ | OCH$_3$ | CH$_2$C≡CCH$_3$ |
| B.806 | CHF$_2$ | CH$_3$ | CH$_2$C≡CCH$_3$ |
| B.807 | CHF$_2$ | CH$_2$CH$_3$ | CH$_2$C≡CCH$_3$ |
| B.808 | CHF$_2$ | CF$_3$ | CH$_2$C≡CCH$_3$ |
| B.809 | CHF$_2$ | Cl | CH$_2$C≡CCH$_3$ |
| B.810 | CHF$_2$ | OCH$_3$ | CH$_2$C≡CCH$_3$ |
| B.811 | CH$_2$F | CH$_3$ | CH$_2$C≡CCH$_3$ |
| B.812 | CH$_2$F | CH$_2$CH$_3$ | CH$_2$C≡CCH$_3$ |
| B.813 | CH$_2$F | CF$_3$ | CH$_2$C≡CCH$_3$ |
| B.814 | CH$_2$F | Cl | CH$_2$C≡CCH$_3$ |
| B.815 | CH$_2$F | OCH$_3$ | CH$_2$C≡CCH$_3$ |
| B.816 | OCH$_3$ | CH$_3$ | CH$_2$C≡CCH$_3$ |
| B.817 | OCH$_3$ | CH$_2$CH$_3$ | CH$_2$C≡CCH$_3$ |
| B.818 | OCH$_3$ | CF$_3$ | CH$_2$C≡CCH$_3$ |
| B.819 | OCH$_3$ | Cl | CH$_2$C≡CCH$_3$ |
| B.820 | OCH$_3$ | OCH$_3$ | CH$_2$C≡CCH$_3$ |
| B.821 | OCH$_2$CH$_3$ | CH$_3$ | CH$_2$C≡CCH$_3$ |
| B.822 | OCH$_2$CH$_3$ | CH$_2$CH$_3$ | CH$_2$C≡CCH$_3$ |
| B.823 | OCH$_2$CH$_3$ | CF$_3$ | CH$_2$C≡CCH$_3$ |
| B.824 | OCH$_2$CH$_3$ | Cl | CH$_2$C≡CCH$_3$ |
| B.825 | OCH$_2$CH$_3$ | OCH$_3$ | CH$_2$C≡CCH$_3$ |
| B.826 | CN | CH$_3$ | CH$_2$C≡CCH$_3$ |
| B.827 | CN | CH$_2$CH$_3$ | CH$_2$C≡CCH$_3$ |
| B.828 | CN | CF$_3$ | CH$_2$C≡CCH$_3$ |
| B.829 | CN | Cl | CH$_2$C≡CCH$_3$ |
| B.830 | CN | OCH$_3$ | CH$_2$C≡CCH$_3$ |
| B.831 | H | CH$_3$ | CH$_2$C≡C—I |
| B.832 | H | CH$_2$CH$_3$ | CH$_2$C≡C—I |
| B.833 | H | CF$_3$ | CH$_2$C≡C—I |
| B.834 | H | Cl | CH$_2$C≡C—I |
| B.835 | H | OCH$_3$ | CH$_2$C≡C—I |
| B.836 | CH$_2$CH$_3$ | CH$_3$ | CH$_2$C≡C—I |
| B.837 | CH$_2$CH$_3$ | CH$_2$CH$_3$ | CH$_2$C≡C—I |
| B.838 | CH$_2$CH$_3$ | CF$_3$ | CH$_2$C≡C—I |
| B.839 | CH$_2$CH$_3$ | Cl | CH$_2$C≡C—I |
| B.840 | CH$_2$CH$_3$ | OCH$_3$ | CH$_2$C≡C—I |
| B.841 | CHF$_2$ | CH$_3$ | CH$_2$C≡C—I |
| B.842 | CHF$_2$ | CH$_2$CH$_3$ | CH$_2$C≡C—I |
| B.843 | CHF$_2$ | CF$_3$ | CH$_2$C≡C—I |
| B.844 | CHF$_2$ | Cl | CH$_2$C≡C—I |
| B.845 | CHF$_2$ | OCH$_3$ | CH$_2$C≡C—I |
| B.846 | CH$_2$F | CH$_3$ | CH$_2$C≡C—I |
| B.847 | CH$_2$F | CH$_2$CH$_3$ | CH$_2$C≡C—I |
| B.848 | CH$_2$F | CF$_3$ | CH$_2$C≡C—I |
| B.849 | CH$_2$F | Cl | CH$_2$C≡C—I |
| B.850 | CH$_2$F | OCH$_3$ | CH$_2$C≡C—I |

TABLE B-continued

| No. | R¹ | R³ | R⁴ |
|---|---|---|---|
| B.851 | OCH₃ | CH₃ | CH₂C≡C—I |
| B.852 | OCH₃ | CH₂CH₃ | CH₂C≡C—I |
| B.853 | OCH₃ | CF₃ | CH₂C≡C—I |
| B.854 | OCH₃ | Cl | CH₂C≡C—I |
| B.855 | OCH₃ | OCH₃ | CH₂C≡C—I |
| B.856 | OCH₂CH₃ | CH₃ | CH₂C≡C—I |
| B.857 | OCH₂CH₃ | CH₂CH₃ | CH₂C≡C—I |
| B.858 | OCH₂CH₃ | CF₃ | CH₂C≡C—I |
| B.859 | OCH₂CH₃ | Cl | CH₂C≡C—I |
| B.860 | OCH₂CH₃ | OCH₃ | CH₂C≡C—I |
| B.861 | CN | CH₃ | CH₂C≡C—I |
| B.862 | CN | CH₂CH₃ | CH₂C≡C—I |
| B.863 | CN | CF₃ | CH₂C≡C—I |
| B.864 | CN | Cl | CH₂C≡C—I |
| B.865 | CN | OCH₃ | CH₂C≡C—I |
| B.866 | H | CH₃ | CH(CH₃)C≡CH |
| B.867 | H | CH₂CH₃ | CH(CH₃)C≡CH |
| B.868 | H | CF₃ | CH(CH₃)C≡CH |
| B.869 | H | Cl | CH(CH₃)C≡CH |
| B.870 | H | OCH₃ | CH(CH₃)C≡CH |
| B.871 | CH₂CH₃ | CH₃ | CH(CH₃)C≡CH |
| B.872 | CH₂CH₃ | CH₂CH₃ | CH(CH₃)C≡CH |
| B.873 | CH₂CH₃ | CF₃ | CH(CH₃)C≡CH |
| B.874 | CH₂CH₃ | Cl | CH(CH₃)C≡CH |
| B.875 | CH₂CH₃ | OCH₃ | CH(CH₃)C≡CH |
| B.876 | CHF₂ | CH₃ | CH(CH₃)C≡CH |
| B.877 | CHF₂ | CH₂CH₃ | CH(CH₃)C≡CH |
| B.878 | CHF₂ | CF₃ | CH(CH₃)C≡CH |
| B.879 | CHF₂ | Cl | CH(CH₃)C≡CH |
| B.880 | CHF₂ | OCH₃ | CH(CH₃)C≡CH |
| B.881 | CH₂F | CH₃ | CH(CH₃)C≡CH |
| B.882 | CH₂F | CH₂CH₃ | CH(CH₃)C≡CH |
| B.883 | CH₂F | CF₃ | CH(CH₃)C≡CH |
| B.884 | CH₂F | Cl | CH(CH₃)C≡CH |
| B.885 | CH₂F | OCH₃ | CH(CH₃)C≡CH |
| B.886 | OCH₃ | CH₃ | CH(CH₃)C≡CH |
| B.887 | OCH₃ | CH₂CH₃ | CH(CH₃)C≡CH |
| B.888 | OCH₃ | CF₃ | CH(CH₃)C≡CH |
| B.889 | OCH₃ | Cl | CH(CH₃)C≡CH |
| B.890 | OCH₃ | OCH₃ | CH(CH₃)C≡CH |
| B.891 | OCH₂CH₃ | CH₃ | CH(CH₃)C≡CH |
| B.892 | OCH₂CH₃ | CH₂CH₃ | CH(CH₃)C≡CH |
| B.893 | OCH₂CH₃ | CF₃ | CH(CH₃)C≡CH |
| B.894 | OCH₂CH₃ | Cl | CH(CH₃)C≡CH |
| B.895 | OCH₂CH₃ | OCH₃ | CH(CH₃)C≡CH |
| B.896 | CN | CH₃ | CH(CH₃)C≡CH |
| B.897 | CN | CH₂CH₃ | CH(CH₃)C≡CH |
| B.898 | CN | CF₃ | CH(CH₃)C≡CH |
| B.899 | CN | Cl | CH(CH₃)C≡CH |
| B.900 | CN | OCH₃ | CH(CH₃)C≡CH |
| B.901 | H | CH₃ | CH₂CH₂—O—CH₂CH₃ |
| B.902 | H | CH₂CH₃ | CH₂CH₂—O—CH₂CH₃ |
| B.903 | H | CF₃ | CH₂CH₂—O—CH₂CH₃ |
| B.904 | H | Cl | CH₂CH₂—O—CH₂CH₃ |
| B.905 | H | OCH₃ | CH₂CH₂—O—CH₂CH₃ |
| B.906 | CH₂CH₃ | CH₃ | CH₂CH₂—O—CH₂CH₃ |
| B.907 | CH₂CH₃ | CH₂CH₃ | CH₂CH₂—O—CH₂CH₃ |
| B.908 | CH₂CH₃ | CF₃ | CH₂CH₂—O—CH₂CH₃ |
| B.909 | CH₂CH₃ | Cl | CH₂CH₂—O—CH₂CH₃ |
| B.910 | CH₂CH₃ | OCH₃ | CH₂CH₂—O—CH₂CH₃ |
| B.911 | CHF₂ | CH₃ | CH₂CH₂—O—CH₂CH₃ |
| B.912 | CHF₂ | CH₂CH₃ | CH₂CH₂—O—CH₂CH₃ |
| B.913 | CHF₂ | CF₃ | CH₂CH₂—O—CH₂CH₃ |
| B.914 | CHF₂ | Cl | CH₂CH₂—O—CH₂CH₃ |
| B.915 | CHF₂ | OCH₃ | CH₂CH₂—O—CH₂CH₃ |
| B.916 | CH₂F | CH₃ | CH₂CH₂—O—CH₂CH₃ |
| B.917 | CH₂F | CH₂CH₃ | CH₂CH₂—O—CH₂CH₃ |
| B.918 | CH₂F | CF₃ | CH₂CH₂—O—CH₂CH₃ |
| B.919 | CH₂F | Cl | CH₂CH₂—O—CH₂CH₃ |
| B.920 | CH₂F | OCH₃ | CH₂CH₂—O—CH₂CH₃ |
| B.921 | OCH₃ | CH₃ | CH₂CH₂—O—CH₂CH₃ |
| B.922 | OCH₃ | CH₂CH₃ | CH₂CH₂—O—CH₂CH₃ |
| B.923 | OCH₃ | CF₃ | CH₂CH₂—O—CH₂CH₃ |
| B.924 | OCH₃ | Cl | CH₂CH₂—O—CH₂CH₃ |
| B.925 | OCH₃ | OCH₃ | CH₂CH₂—O—CH₂CH₃ |
| B.926 | OCH₂CH₃ | CH₃ | CH₂CH₂—O—CH₂CH₃ |
| B.927 | OCH₂CH₃ | CH₂CH₃ | CH₂CH₂—O—CH₂CH₃ |
| B.928 | OCH₂CH₃ | CF₃ | CH₂CH₂—O—CH₂CH₃ |
| B.929 | OCH₂CH₃ | Cl | CH₂CH₂—O—CH₂CH₃ |
| B.930 | OCH₂CH₃ | OCH₃ | CH₂CH₂—O—CH₂CH₃ |
| B.931 | CN | CH₃ | CH₂CH₂—O—CH₂CH₃ |
| B.932 | CN | CH₂CH₃ | CH₂CH₂—O—CH₂CH₃ |
| B.933 | CN | CF₃ | CH₂CH₂—O—CH₂CH₃ |
| B.934 | CN | Cl | CH₂CH₂—O—CH₂CH₃ |
| B.935 | CN | OCH₃ | CH₂CH₂—O—CH₂CH₃ |
| B.936 | H | CH₃ | CH₂—C₆H₅ |
| B.937 | H | CH₂CH₃ | CH₂—C₆H₅ |
| B.938 | H | CF₃ | CH₂—C₆H₅ |
| B.939 | H | Cl | CH₂—C₆H₅ |
| B.940 | H | OCH₃ | CH₂—C₆H₅ |
| B.941 | CH₂CH₃ | CH₃ | CH₂—C₆H₅ |
| B.942 | CH₂CH₃ | CH₂CH₃ | CH₂—C₆H₅ |
| B.943 | CH₂CH₃ | CF₃ | CH₂—C₆H₅ |
| B.944 | CH₂CH₃ | Cl | CH₂—C₆H₅ |
| B.945 | CH₂CH₃ | OCH₃ | CH₂—C₆H₅ |
| B.946 | CHF₂ | CH₃ | CH₂—C₆H₅ |
| B.947 | CHF₂ | CH₂CH₃ | CH₂—C₆H₅ |
| B.948 | CHF₂ | CF₃ | CH₂—C₆H₅ |
| B.949 | CHF₂ | Cl | CH₂—C₆H₅ |
| B.950 | CHF₂ | OCH₃ | CH₂—C₆H₅ |
| B.951 | CH₂F | CH₃ | CH₂—C₆H₅ |
| B.952 | CH₂F | CH₂CH₃ | CH₂—C₆H₅ |
| B.953 | CH₂F | CF₃ | CH₂—C₆H₅ |
| B.954 | CH₂F | Cl | CH₂—C₆H₅ |
| B.955 | CH₂F | OCH₃ | CH₂—C₆H₅ |
| B.956 | OCH₃ | CH₃ | CH₂—C₆H₅ |
| B.957 | OCH₃ | CH₂CH₃ | CH₂—C₆H₅ |
| B.958 | OCH₃ | CF₃ | CH₂—C₆H₅ |
| B.959 | OCH₃ | Cl | CH₂—C₆H₅ |
| B.960 | OCH₃ | OCH₃ | CH₂—C₆H₅ |
| B.961 | OCH₂CH₃ | CH₃ | CH₂—C₆H₅ |
| B.962 | OCH₂CH₃ | CH₂CH₃ | CH₂—C₆H₅ |
| B.963 | OCH₂CH₃ | CF₃ | CH₂—C₆H₅ |
| B.964 | OCH₂CH₃ | Cl | CH₂—C₆H₅ |
| B.965 | OCH₂CH₃ | OCH₃ | CH₂—C₆H₅ |
| B.966 | CN | CH₃ | CH₂—C₆H₅ |
| B.967 | CN | CH₂CH₃ | CH₂—C₆H₅ |
| B.968 | CN | CF₃ | CH₂—C₆H₅ |
| B.969 | CN | Cl | CH₂—C₆H₅ |
| B.970 | CN | OCH₃ | CH₂—C₆H₅ |
| B.971 | H | CH₃ | cyclopropyl |
| B.972 | H | CH₂CH₃ | cyclopropyl |
| B.973 | H | CF₃ | cyclopropyl |
| B.974 | H | Cl | cyclopropyl |
| B.975 | H | OCH₃ | cyclopropyl |
| B.976 | CH₂CH₃ | CH₃ | cyclopropyl |
| B.977 | CH₂CH₃ | CH₂CH₃ | cyclopropyl |
| B.978 | CH₂CH₃ | CF₃ | cyclopropyl |
| B.979 | CH₂CH₃ | Cl | cyclopropyl |
| B.980 | CH₂CH₃ | OCH₃ | cyclopropyl |
| B.981 | CHF₂ | CH₃ | cyclopropyl |
| B.982 | CHF₂ | CH₂CH₃ | cyclopropyl |
| B.983 | CHF₂ | CF₃ | cyclopropyl |
| B.984 | CHF₂ | Cl | cyclopropyl |
| B.985 | CHF₂ | OCH₃ | cyclopropyl |
| B.986 | CH₂F | CH₃ | cyclopropyl |
| B.987 | CH₂F | CH₂CH₃ | cyclopropyl |
| B.988 | CH₂F | CF₃ | cyclopropyl |
| B.989 | CH₂F | Cl | cyclopropyl |
| B.990 | CH₂F | OCH₃ | cyclopropyl |
| B.991 | OCH₃ | CH₃ | cyclopropyl |
| B.992 | OCH₃ | CH₂CH₃ | cyclopropyl |
| B.993 | OCH₃ | CF₃ | cyclopropyl |
| B.994 | OCH₃ | Cl | cyclopropyl |
| B.995 | OCH₃ | OCH₃ | cyclopropyl |
| B.996 | OCH₂CH₃ | CH₃ | cyclopropyl |
| B.997 | OCH₂CH₃ | CH₂CH₃ | cyclopropyl |
| B.998 | OCH₂CH₃ | CF₃ | cyclopropyl |
| B.999 | OCH₂CH₃ | Cl | cyclopropyl |
| B.1000 | OCH₂CH₃ | OCH₃ | cyclopropyl |
| B.1001 | CN | CH₃ | cyclopropyl |
| B.1002 | CN | CH₂CH₃ | cyclopropyl |
| B.1003 | CN | CF₃ | cyclopropyl |
| B.1004 | CN | Cl | cyclopropyl |

TABLE B-continued

| No. | R¹ | R³ | R⁴ |
|---|---|---|---|
| B.1005 | CN | OCH₃ | cyclopropyl |
| B.1006 | H | CH₃ | CH₂-(2,2-Cl₂-cyclopropyl) |
| B.1007 | H | CH₂CH₃ | CH₂-(2,2-Cl₂-cyclopropyl) |
| B.1008 | H | CF₃ | CH₂-(2,2-Cl₂-cyclopropyl) |
| B.1009 | H | Cl | CH₂-(2,2-Cl₂-cyclopropyl) |
| B.1010 | H | OCH₃ | CH₂-(2,2-Cl₂-cyclopropyl) |
| B.1011 | CH₂CH₃ | CH₃ | CH₂-(2,2-Cl₂-cyclopropyl) |
| B.1012 | CH₂CH₃ | CH₂CH₃ | CH₂-(2,2-Cl₂-cyclopropyl) |
| B.1013 | CH₂CH₃ | CF₃ | CH₂-(2,2-Cl₂-cyclopropyl) |
| B.1014 | CH₂CH₃ | Cl | CH₂-(2,2-Cl₂-cyclopropyl) |
| B.1015 | CH₂CH₃ | OCH₃ | CH₂-(2,2-Cl₂-cyclopropyl) |
| B.1016 | CHF₂ | CH₃ | CH₂-(2,2-Cl₂-cyclopropyl) |
| B.1017 | CHF₂ | CH₂CH₃ | CH₂-(2,2-Cl₂-cyclopropyl) |
| B.1018 | CHF₂ | CF₃ | CH₂-(2,2-Cl₂-cyclopropyl) |
| B.1019 | CHF₂ | Cl | CH₂-(2,2-Cl₂-cyclopropyl) |
| B.1020 | CHF₂ | OCH₃ | CH₂-(2,2-Cl₂-cyclopropyl) |
| B.1021 | CH₂F | CH₃ | CH₂-(2,2-Cl₂-cyclopropyl) |
| B.1022 | CH₂F | CH₂CH₃ | CH₂-(2,2-Cl₂-cyclopropyl) |
| B.1023 | CH₂F | CF₃ | CH₂-(2,2-Cl₂-cyclopropyl) |
| B.1024 | CH₂F | Cl | CH₂-(2,2-Cl₂-cyclopropyl) |
| B.1025 | CH₂F | OCH₃ | CH₂-(2,2-Cl₂-cyclopropyl) |
| B.1026 | OCH₃ | CH₃ | CH₂-(2,2-Cl₂-cyclopropyl) |
| B 1027 | OCH₃ | CH₂CH₃ | CH₂-(2,2-Cl₂-cyclopropyl) |
| B.1028 | CCH₃ | CF₃ | CH₂-(2,2-Cl₂-cyclopropyl) |
| B.1029 | OCH₃ | Cl | CH₂-(2,2-Cl₂-cyclopropyl) |
| B.1030 | OCH₃ | OCH₃ | CH₂-(2,2-Cl₂-cyclopropyl) |
| B.1031 | OCH₂CH₃ | CH₃ | CH₂-(2,2-Cl₂-cyclopropyl) |
| B.1032 | OCH₂CH₃ | CH₂CH₃ | CH₂-(2,2-Cl₂-cyclopropyl) |
| B.1033 | OCH₂CH₃ | CF₃ | CH₂-(2,2-Cl₂-cyclopropyl) |
| B.2067 | OCH₂CH₃ | Cl | CH₂-(2,2-Cl₂-cyclopropyl) |
| B.2068 | OCH₂CH₃ | OCH₃ | CH₂-(2,2-Cl₂-cyclopropyl) |
| B.2069 | CN | CH₃ | CH₂-(2,2-Cl₂-cyclopropyl) |
| B.2070 | CN | CH₂CH₃ | CH₂-(2,2-Cl₂-cyclopropyl) |
| B.2071 | CN | CF₃ | CH₂-(2,2-Cl₂-cyclopropyl) |
| B.2072 | CN | Cl | CH₂-(2,2-Cl₂-cyclopropyl) |
| B.2073 | CN | OCH₃ | CH₂-(2,2-Cl₂-cyclopropyl) |

TABLE C

| No. | R¹ | Rˣ | Rʸ | Rᶻ |
|---|---|---|---|---|
| C.1 | CH₃ | H | H | H |
| C.2 | CH₃ | H | CH₃ | H |
| C.3 | CH₃ | H | C₂H₅ | H |
| C.4 | CH₃ | H | C₃H₇ | H |
| C.5 | CH₃ | H | C₄H₉ | H |
| C.6 | CH₃ | H | CH(CH₃)₂ | H |
| C.7 | CH₃ | H | cyclopropyl | H |
| C.8 | CH₃ | H | CF₃ | H |
| C.9 | CH₃ | H | OCH₃ | H |
| C.10 | CH₃ | H | OC₂H₅ | H |
| C.11 | CH₃ | H | CH₂—C₆H₅ | H |
| C.12 | CH₃ | H | CH(CH₃)C₆H₅ | H |
| C.13 | CH₃ | H | C₆H₅ | H |
| C.14 | CH₃ | H | 4-F—C₆H₅ | H |
| C.15 | CH₃ | H | 4-Cl-2-pyridyl | H |
| C.16 | CH₃ | H | F | H |
| C.17 | CH₃ | H | CN | H |
| C.18 | CH₃ | CH₃ | H | H |
| C.19 | CH₃ | CH₃ | CH₃ | H |
| C.20 | CH₃ | CH₃ | C₂H₅ | H |
| C.21 | CH₃ | CH₃ | C₃H₇ | H |
| C.22 | CH₃ | CH₃ | C₄H₉ | H |
| C.23 | CH₃ | CH₃ | CH(CH₃)₂ | H |
| C.24 | CH₃ | CH₃ | cyclopropyl | H |
| C.25 | CH₃ | CH₃ | CF₃ | H |
| C.26 | CH₃ | CH₃ | OCH₃ | H |
| C.27 | CH₃ | CH₃ | OC₂H₅ | H |
| C.28 | CH₃ | CH₃ | CH₂—C₆H₅ | H |
| C.29 | CH₃ | CH₃ | CH(CH₃)C₆H₅ | H |
| C.30 | CH₃ | CH₃ | C₆H₅ | H |
| C.31 | CH₃ | CH₃ | 4-F—C₆H₅ | H |
| C.32 | CH₃ | CH₃ | 4-Cl-2-pyridyl | H |
| C.33 | CH₃ | CH₃ | F | H |

TABLE C-continued

| No. | R¹ | Rˣ | Rʸ | Rᶻ |
|---|---|---|---|---|
| C.34 | CH₃ | CH₃ | CN | H |
| C.35 | CH₃ | C₂H₅ | H | H |
| C.36 | CH₃ | C₂H₅ | CH₃ | H |
| C.37 | CH₃ | C₂H₅ | C₂H₅ | H |
| C.38 | CH₃ | C₂H₅ | C₃H₇ | H |
| C.39 | CH₃ | C₂H₅ | C₄H₉ | H |
| C.40 | CH₃ | C₂H₅ | CH(CH₃)₂ | H |
| C.41 | CH₃ | C₂H₅ | cyclopropyl | H |
| C.42 | CH₃ | C₂H₅ | CF₃ | H |
| C.43 | CH₃ | C₂H₅ | OCH₃ | H |
| C.44 | CH₃ | C₂H₅ | OC₂H₅ | H |
| C.45 | CH₃ | C₂H₅ | CH₂—C₆H₅ | H |
| C.46 | CH₃ | C₂H₅ | CH(CH₃)C₆H₅ | H |
| C.47 | CH₃ | C₂H₅ | C₆H₅ | H |
| C.48 | CH₃ | C₂H₅ | 4-F—C₆H₅ | H |
| C.49 | CH₃ | C₂H₅ | 4-Cl-2-pyridyl | H |
| C.50 | CH₃ | C₂H₅ | F | H |
| C.51 | CH₃ | C₂H₅ | CN | H |
| C.52 | CH₃ | cyclopropyl | H | H |
| C.53 | CH₃ | cyclopropyl | CH₃ | H |
| C.54 | CH₃ | cyclopropyl | C₂H₅ | H |
| C.55 | CH₃ | cyclopropyl | C₃H₇ | H |
| C.56 | CH₃ | cyclopropyl | C₄H₉ | H |
| C.57 | CH₃ | cyclopropyl | CH(CH₃)₂ | H |
| C.58 | CH₃ | cyclopropyl | cyclopropyl | H |
| C.59 | CH₃ | cyclopropyl | CF₃ | H |
| C.60 | CH₃ | cyclopropyl | OCH₃ | H |
| C.61 | CH₃ | cyclopropyl | OC₂H₅ | H |
| C.62 | CH₃ | cyclopropyl | CH₂—C₆H₅ | H |
| C.63 | CH₃ | cyclopropyl | CH(CH₃)C₆H₅ | H |
| C.64 | CH₃ | cyclopropyl | C₆H₅ | H |
| C.65 | CH₃ | cyclopropyl | 4-F—C₆H₅ | H |
| C.66 | CH₃ | cyclopropyl | 4-Cl-2-pyridyl | H |
| C.67 | CH₃ | cyclopropyl | F | H |
| C.68 | CH₃ | cyclopropyl | CN | H |
| C.69 | CH₃ | CF₃ | H | H |
| C.70 | CH₃ | CF₃ | CH₃ | H |
| C.71 | CH₃ | CF₃ | C₂H₅ | H |
| C.72 | CH₃ | CF₃ | C₃H₇ | H |
| C.73 | CH₃ | CF₃ | C₄H₉ | H |
| C.74 | CH₃ | CF₃ | CH(CH₃)₂ | H |
| C.75 | CH₃ | CF₃ | cyclopropyl | H |
| C.76 | CH₃ | CF₃ | CF₃ | H |
| C.77 | CH₃ | CF₃ | OCH₃ | H |
| C.78 | CH₃ | CF₃ | OC₂H₅ | H |
| C.79 | CH₃ | CF₃ | CH₂—C₆H₅ | H |
| C.80 | CH₃ | CF₃ | CH(CH₃)C₆H₅ | H |
| C.81 | CH₃ | CF₃ | C₆H₅ | H |
| C.82 | CH₃ | CF₃ | 4-F—C₆H₅ | H |
| C.83 | CH₃ | CF₃ | 4-Cl-2-pyridyl | H |
| C.84 | CH₃ | CF₃ | F | H |
| C.85 | CH₃ | CF₃ | CN | H |
| C.86 | CH₃ | Cl | H | H |
| C.87 | CH₃ | Cl | CH₃ | H |
| C.88 | CH₃ | Cl | C₂H₅ | H |
| C.89 | CH₃ | Cl | C₃H₇ | H |
| C.90 | CH₃ | Cl | C₄H₉ | H |
| C.91 | CH₃ | Cl | CH(CH₃)2 | H |
| C.92 | CH₃ | Cl | cyclopropyl | H |
| C.93 | CH₃ | Cl | CF₃ | H |
| C.94 | CH₃ | Cl | OCH₃ | H |
| C.95 | CH₃ | Cl | OC₂H₅ | H |
| C.96 | CH₃ | Cl | CH₂—C₆H₅ | H |
| C.97 | CH₃ | Cl | CH(CH₃)C₆H₅ | H |
| C.98 | CH₃ | Cl | C₆H₅ | H |
| C.99 | CH₃ | Cl | 4-F—C₆H₅ | H |
| C.100 | CH₃ | Cl | 4-Cl-2-pyridyl | H |
| C.101 | CH₃ | Cl | F | H |
| C.102 | CH₃ | Cl | CN | H |
| C.103 | CH₃ | F | H | H |
| C.104 | CH₃ | F | CH₃ | H |
| C.105 | CH₃ | F | C₂H₅ | H |
| C.106 | CH₃ | F | C₃H₇ | H |
| C.107 | CH₃ | F | C₄H₉ | H |
| C.108 | CH₃ | F | CH(CH₃)₂ | H |
| C.109 | CH₃ | F | cyclopropyl | H |
| C.110 | CH₃ | F | CF₃ | H |

TABLE C-continued

| No. | $R^1$ | $R^x$ | $R^y$ | $R^z$ |
|---|---|---|---|---|
| C.111 | $CH_3$ | F | $OCH_3$ | H |
| C.112 | $CH_3$ | F | $OC_2H_5$ | H |
| C.113 | $CH_3$ | F | $CH_2$—$C_6H_5$ | H |
| C.114 | $CH_3$ | F | $CH(CH_3)C_6H_5$ | H |
| C.115 | $CH_3$ | F | $C_6H_5$ | H |
| C.116 | $CH_3$ | F | 4-F—$C_6H_5$ | H |
| C.117 | $CH_3$ | F | 4-Cl-2-pyridyl | H |
| C.118 | $CH_3$ | F | F | H |
| C.119 | $CH_3$ | F | CN | H |
| C.120 | $CH_3$ | $OCH_3$ | H | H |
| C.121 | $CH_3$ | $OCH_3$ | $CH_3$ | H |
| C.122 | $CH_3$ | $OCH_3$ | $C_2H_5$ | H |
| C.123 | $CH_3$ | $OCH_3$ | $C_3H_7$ | H |
| C.124 | $CH_3$ | $OCH_3$ | $C_4H_9$ | H |
| C.125 | $CH_3$ | $OCH_3$ | $CH(CH_3)2$ | H |
| C.126 | $CH_3$ | $OCH_3$ | cyclopropyl | H |
| C.127 | $CH_3$ | $OCH_3$ | $CF_3$ | H |
| C.128 | $CH_3$ | $OCH_3$ | $OCH_3$ | H |
| C.129 | $CH_3$ | $OCH_3$ | $OC_2H_5$ | H |
| C.130 | $CH_3$ | $OCH_3$ | $CH_2$—$C_6H_5$ | H |
| C.131 | $CH_3$ | $OCH_3$ | $CH(CH_3)C_6H_5$ | H |
| C.132 | $CH_3$ | $OCH_3$ | $C_6H_5$ | H |
| C.133 | $CH_3$ | $OCH_3$ | 4-F—$C_6H_5$ | H |
| C.134 | $CH_3$ | $OCH_3$ | 4-Cl-2-pyridyl | H |
| C.135 | $CH_3$ | $OCH_3$ | F | H |
| C.136 | $CH_3$ | $OCH_3$ | CN | H |
| C.137 | $CH_3$ | H | H | $CH_3$ |
| C.138 | $CH_3$ | H | $CH_3$ | $CH_3$ |
| C.139 | $CH_3$ | H | $C_2H_5$ | $CH_3$ |
| C.140 | $CH_3$ | H | $C_3H_7$ | $CH_3$ |
| C.141 | $CH_3$ | H | $C_4H_9$ | $CH_3$ |
| C.142 | $CH_3$ | H | $CH(CH_3)2$ | $CH_3$ |
| C.143 | $CH_3$ | H | cyclopropyl | $CH_3$ |
| C.144 | $CH_3$ | H | $CF_3$ | $CH_3$ |
| C.145 | $CH_3$ | H | $OCH_3$ | $CH_3$ |
| C.146 | $CH_3$ | H | $OC_2H_5$ | $CH_3$ |
| C.147 | $CH_3$ | H | $CH_2$—$C_6H_5$ | $CH_3$ |
| C.148 | $CH_3$ | H | $CH(CH_3)C_6H_5$ | $CH_3$ |
| C.149 | $CH_3$ | H | $C_6H_5$ | $CH_3$ |
| C.150 | $CH_3$ | H | 4-F—$C_6H_5$ | $CH_3$ |
| C.151 | $CH_3$ | H | 4-Cl-2-pyridyl | $CH_3$ |
| C.152 | $CH_3$ | H | F | $CH_3$ |
| C.153 | $CH_3$ | H | CN | $CH_3$ |
| C.154 | $CH_3$ | $CH_3$ | H | $CH_3$ |
| C.155 | $CH_3$ | $CH_3$ | $CH_3$ | $CH_3$ |
| C.156 | $CH_3$ | $CH_3$ | $C_2H_5$ | $CH_3$ |
| C.157 | $CH_3$ | $CH_3$ | $C_3H_7$ | $CH_3$ |
| C.158 | $CH_3$ | $CH_3$ | $C_4H_9$ | $CH_3$ |
| C.159 | $CH_3$ | $CH_3$ | $CH(CH_3)_2$ | $CH_3$ |
| C.160 | $CH_3$ | $CH_3$ | cyclopropyl | $CH_3$ |
| C.161 | $CH_3$ | $CH_3$ | $CF_3$ | $CH_3$ |
| C.162 | $CH_3$ | $CH_3$ | $OCH_3$ | $CH_3$ |
| C.163 | $CH_3$ | $CH_3$ | $OC_2H_5$ | $CH_3$ |
| C.164 | $CH_3$ | $CH_3$ | $CH_2$—$C_6H_5$ | $CH_3$ |
| C.165 | $CH_3$ | $CH_3$ | $CH(CH_3)C_6H_5$ | $CH_3$ |
| C.166 | $CH_3$ | $CH_3$ | $C_6H_5$ | $CH_3$ |
| C.167 | $CH_3$ | $CH_3$ | 4-F—$C_6H_5$ | $CH_3$ |
| C.168 | $CH_3$ | $CH_3$ | 4-Cl-2-pyridyl | $CH_3$ |
| C.169 | $CH_3$ | $CH_3$ | F | $CH_3$ |
| C.170 | $CH_3$ | $CH_3$ | CN | $CH_3$ |
| C.171 | $CH_3$ | $C_2H_5$ | H | $CH_3$ |
| C.172 | $CH_3$ | $C_2H_5$ | $CH_3$ | $CH_3$ |
| C.173 | $CH_3$ | $C_2H_5$ | $C_2H_5$ | $CH_3$ |
| C.174 | $CH_3$ | $C_2H_5$ | $C_3H_7$ | $CH_3$ |
| C.175 | $CH_3$ | $C_2H_5$ | $C_4H_9$ | $CH_3$ |
| C.176 | $CH_3$ | $C_2H_5$ | $CH(CH_3)_2$ | $CH_3$ |
| C.177 | $CH_3$ | $C_2H_5$ | cyclopropyl | $CH_3$ |
| C.178 | $CH_3$ | $C_2H_5$ | $CF_3$ | $CH_3$ |
| C.179 | $CH_3$ | $C_2H_5$ | $OCH_3$ | $CH_3$ |
| C.180 | $CH_3$ | $C_2H_5$ | $OC_2H_5$ | $CH_3$ |
| C.181 | $CH_3$ | $C_2H_5$ | $CH_2$—$C_6H_5$ | $CH_3$ |
| C.182 | $CH_3$ | $C_2H_5$ | $CH(CH_3)C_6H_5$ | $CH_3$ |
| C.183 | $CH_3$ | $C_2H_5$ | $C_6H_5$ | $CH_3$ |
| C.184 | $CH_3$ | $C_2H_5$ | 4-F—$C_6H_5$ | $CH_3$ |
| C.185 | $CH_3$ | $C_2H_5$ | 4-Cl-2-pyridyl | $CH_3$ |
| C.186 | $CH_3$ | $C_2H_5$ | F | $CH_3$ |
| C.187 | $CH_3$ | $C_2H_5$ | CN | $CH_3$ |
| C.188 | $CH_3$ | cyclopropyl | H | $CH_3$ |
| C.189 | $CH_3$ | cyclopropyl | $CH_3$ | $CH_3$ |
| C.190 | $CH_3$ | cyclopropyl | $C_2H_5$ | $CH_3$ |
| C.191 | $CH_3$ | cyclopropyl | $C_3H_7$ | $CH_3$ |
| C.192 | $CH_3$ | cyclopropyl | $C_4H_9$ | $CH_3$ |
| C.193 | $CH_3$ | cyclopropyl | $CH(CH_3)_2$ | $CH_3$ |
| C.194 | $CH_3$ | cyclopropyl | cyclopropyl | $CH_3$ |
| C.195 | $CH_3$ | cyclopropyl | $CF_3$ | $CH_3$ |
| C.196 | $CH_3$ | cyclopropyl | $OCH_3$ | $CH_3$ |
| C.197 | $CH_3$ | cyclopropyl | $OC_2H_5$ | $CH_3$ |
| C.198 | $CH_3$ | cyclopropyl | $CH_2$—$C_6H_5$ | $CH_3$ |
| C.199 | $CH_3$ | cyclopropyl | $CH(CH_3)C_6H_5$ | $CH_3$ |
| C.200 | $CH_3$ | cyclopropyl | $C_6H_5$ | $CH_3$ |
| C.201 | $CH_3$ | cyclopropyl | 4-F—$C_6H_5$ | $CH_3$ |
| C.202 | $CH_3$ | cyclopropyl | 4-Cl-2-pyridyl | $CH_3$ |
| C.203 | $CH_3$ | cyclopropyl | F | $CH_3$ |
| C.204 | $CH_3$ | cyclopropyl | CN | $CH_3$ |
| C.205 | $CH_3$ | $CF_3$ | H | $CH_3$ |
| C.206 | $CH_3$ | $CF_3$ | $CH_3$ | $CH_3$ |
| C.207 | $CH_3$ | $CF_3$ | $C_2H_5$ | $CH_3$ |
| C.208 | $CH_3$ | $CF_3$ | $C_3H_7$ | $CH_3$ |
| C.209 | $CH_3$ | $CF_3$ | $C_4H_9$ | $CH_3$ |
| C.210 | $CH_3$ | $CF_3$ | $CH(CH_3)_2$ | $CH_3$ |
| C.211 | $CH_3$ | $CF_3$ | cyclopropyl | $CH_3$ |
| C.212 | $CH_3$ | $CF_3$ | $CF_3$ | $CH_3$ |
| C.213 | $CH_3$ | $CF_3$ | $OCH_3$ | $CH_3$ |
| C.214 | $CH_3$ | $CF_3$ | $OC_2H_5$ | $CH_3$ |
| C.215 | $CH_3$ | $CF_3$ | $CH_2$—$C_6H_5$ | $CH_3$ |
| C.216 | $CH_3$ | $CF_3$ | $CH(CH_3)C_6H_5$ | $CH_3$ |
| C.217 | $CH_3$ | $CF_3$ | $C_6H_5$ | $CH_3$ |
| C.218 | $CH_3$ | $CF_3$ | 4-F—$C_6H_5$ | $CH_3$ |
| C.219 | $CH_3$ | $CF_3$ | 4-Cl-2-pyridyl | $CH_3$ |
| C.220 | $CH_3$ | $CF_3$ | F | $CH_3$ |
| C.221 | $CH_3$ | $CF_3$ | CN | $CH_3$ |
| C.222 | $CH_3$ | Cl | H | $CH_3$ |
| C.223 | $CH_3$ | Cl | $CH_3$ | $CH_3$ |
| C.224 | $CH_3$ | Cl | $C_2H_5$ | $CH_3$ |
| C.225 | $CH_3$ | Cl | $C_3H_7$ | $CH_3$ |
| C.226 | $CH_3$ | Cl | $C_4H_9$ | $CH_3$ |
| C.227 | $CH_3$ | Cl | $CH(CH_3)_2$ | $CH_3$ |
| C.228 | $CH_3$ | Cl | cyclopropyl | $CH_3$ |
| C.229 | $CH_3$ | Cl | $CF_3$ | $CH_3$ |
| C.230 | $CH_3$ | Cl | $OCH_3$ | $CH_3$ |
| C.231 | $CH_3$ | Cl | $OC_2H_5$ | $CH_3$ |
| C.232 | $CH_3$ | Cl | $CH_2$—$C_6H_5$ | $CH_3$ |
| C.233 | $CH_3$ | Cl | $CH(CH_3)C_6H_5$ | $CH_3$ |
| C.234 | $CH_3$ | Cl | $C_6H_5$ | $CH_3$ |
| C.235 | $CH_3$ | Cl | 4-F—$C_6H_5$ | $CH_3$ |
| C.236 | $CH_3$ | Cl | 4-Cl-2-pyridyl | $CH_3$ |
| C.237 | $CH_3$ | Cl | F | $CH_3$ |
| C.238 | $CH_3$ | Cl | CN | $CH_3$ |
| C.239 | $CH_3$ | F | H | $CH_3$ |
| C.240 | $CH_3$ | F | $CH_3$ | $CH_3$ |
| C.241 | $CH_3$ | F | $C_2H_5$ | $CH_3$ |
| C.242 | $CH_3$ | F | $C_3H_7$ | $CH_3$ |
| C.243 | $CH_3$ | F | $C_4H_9$ | $CH_3$ |
| C.244 | $CH_3$ | F | $CH(CH_3)_2$ | $CH_3$ |
| C.245 | $CH_3$ | F | cyclopropyl | $CH_3$ |
| C.246 | $CH_3$ | F | $CF_3$ | $CH_3$ |
| C.247 | $CH_3$ | F | $OCH_3$ | $CH_3$ |
| C.248 | $CH_3$ | F | $OC_2H_5$ | $CH_3$ |
| C.249 | $CH_3$ | F | $CH_2$—$C_6H_5$ | $CH_3$ |
| C.250 | $CH_3$ | F | $CH(CH_3)C_6H_5$ | $CH_3$ |
| C.251 | $CH_3$ | F | $C_6H_5$ | $CH_3$ |
| C.252 | $CH_3$ | F | 4-F—$C_6H_5$ | $CH_3$ |
| C.253 | $CH_3$ | F | 4-Cl-2-pyridyl | $CH_3$ |
| C.254 | $CH_3$ | F | F | $CH_3$ |
| C.255 | $CH_3$ | F | CN | $CH_3$ |
| C.256 | $CH_3$ | $OCH_3$ | H | $CH_3$ |
| C.257 | $CH_3$ | $OCH_3$ | $CH_3$ | $CH_3$ |
| C.258 | $CH_3$ | $OCH_3$ | $C_2H_5$ | $CH_3$ |
| C.259 | $CH_3$ | $OCH_3$ | $C_3H_7$ | $CH_3$ |
| C.260 | $CH_3$ | $OCH_3$ | $C_4H_9$ | $CH_3$ |
| C.261 | $CH_3$ | $OCH_3$ | $CH(CH_3)_2$ | $CH_3$ |
| C.262 | $CH_3$ | $OCH_3$ | cyclopropyl | $CH_3$ |
| C.263 | $CH_3$ | $OCH_3$ | $CF_3$ | $CH_3$ |
| C.264 | $CH_3$ | $OCH_3$ | $OCH_3$ | $CH_3$ |

TABLE C-continued

| No. | R¹ | Rˣ | Rʸ | Rᶻ |
|---|---|---|---|---|
| C.265 | CH₃ | OCH₃ | OC₂H₅ | CH₃ |
| C.266 | CH₃ | OCH₃ | CH₂—C₆H₅ | CH₃ |
| C.267 | CH₃ | OCH₃ | CH(CH₃)C₆H₅ | CH₃ |
| C.268 | CH₃ | OCH₃ | C₆H₅ | CH₃ |
| C.269 | CH₃ | OCH₃ | 4-F—C₆H₅ | CH₃ |
| C.270 | CH₃ | OCH₃ | 4-Cl-2-pyridyl | CH₃ |
| C.271 | CH₃ | OCH₃ | F | CH₃ |
| C.272 | CH₃ | OCH₃ | CN | CH₃ |
| C.273 | H | CH₃ | H | H |
| C.274 | H | CH₃ | CH₃ | H |
| C.275 | H | CH₃ | C₂H₅ | H |
| C.276 | H | CH₃ | C₃H₇ | H |
| C.277 | H | CH₃ | C₄H₉ | H |
| C.278 | H | CH₃ | CH(CH₃)₂ | H |
| C.279 | H | CH₃ | cyclopropyl | H |
| C.280 | H | CH₃ | CF₃ | H |
| C.281 | H | CH₃ | OCH₃ | H |
| C.282 | H | CH₃ | OC₂H₅ | H |
| C.283 | H | CH₃ | CH₂—C₆H₅ | H |
| C.284 | H | CH₃ | CH(CH₃)C₆H₅ | H |
| C.285 | H | CH₃ | C₆H₅ | H |
| C.286 | H | CH₃ | 4-F—C₆H₅ | H |
| C.287 | H | CH₃ | 4-Cl-2-pyridyl | H |
| C.288 | H | CH₃ | F | H |
| C.289 | H | CH₃ | CN | H |
| C.290 | H | CH₃ | H | CH₃ |
| C.291 | H | CH₃ | CH₃ | CH₃ |
| C.292 | H | CH₃ | C₂H₅ | CH₃ |
| C.293 | H | CH₃ | C₃H₇ | CH₃ |
| C.294 | H | CH₃ | C₄H₉ | CH₃ |
| C.295 | H | CH₃ | CH(CH₃)₂ | CH₃ |
| C.296 | H | CH₃ | cyclopropyl | CH₃ |
| C.297 | H | CH₃ | CF₃ | CH₃ |
| C.298 | H | CH₃ | OCH₃ | CH₃ |
| C.299 | H | CH₃ | OC₂H₅ | CH₃ |
| C.300 | H | CH₃ | CH₂—C₆H₅ | CH₃ |
| C.301 | H | CH₃ | CH(CH₃)C₆H₅ | CH₃ |
| C.302 | H | CH₃ | C₆H₅ | CH₃ |
| C.303 | H | CH₃ | 4-F—C₆H₅ | CH₃ |
| C.304 | H | CH₃ | 4-Cl-2-pyridyl | CH₃ |
| C.305 | H | CH₃ | F | CH₃ |
| C.306 | H | CH₃ | CN | CH₃ |
| C.307 | H | CF₃ | H | H |
| C.308 | H | CF₃ | CH₃ | H |
| C.309 | H | CF₃ | C₂H₅ | H |
| C.310 | H | CF₃ | C₃H₇ | H |
| C.311 | H | CF₃ | C₄H₉ | H |
| C.312 | H | CF₃ | CH(CH₃)₂ | H |
| C.313 | H | CF₃ | cyclopropyl | H |
| C.314 | H | CF₃ | CF₃ | H |
| C.315 | H | CF₃ | OCH₃ | H |
| C.316 | H | CF₃ | OC₂H₅ | H |
| C.317 | H | CF₃ | CH₂—C₆H₅ | H |
| C.318 | H | CF₃ | CH(CH₃)C₆H₅ | H |
| C.319 | H | CF₃ | C₆H₅ | H |
| C.320 | H | CF₃ | 4-F—C₆H₅ | H |
| C.321 | H | CF₃ | 4-Cl-2-pyridyl | H |
| C.322 | H | CF₃ | F | H |
| C.323 | H | CF₃ | CN | H |
| C.324 | H | CF₃ | H | CH₃ |
| C.325 | H | CF₃ | CH₃ | CH₃ |
| C.326 | H | CF₃ | C₂H₅ | CH₃ |
| C.327 | H | CF₃ | C₃H₇ | CH₃ |
| C.328 | H | CF₃ | C₄H₉ | CH₃ |
| C.329 | H | CF₃ | CH(CH₃)₂ | CH₃ |
| C.330 | H | CF₃ | cyclopropyl | CH₃ |
| C.331 | H | CF₃ | CF₃ | CH₃ |
| C.332 | H | CF₃ | OCH₃ | CH₃ |
| C.333 | H | CF₃ | OC₂H₅ | CH₃ |
| C.334 | H | CF₃ | CH₂—C₆H₅ | CH₃ |
| C.335 | H | CF₃ | CH(CH₃)C₆H₅ | CH₃ |
| C.336 | H | CF₃ | C₆H₅ | CH₃ |
| C.337 | H | CF₃ | 4-F—C₆H₅ | CH₃ |
| C.338 | H | CF₃ | 4-Cl-2-pyridyl | CH₃ |
| C.339 | H | CF₃ | F | CH₃ |
| C.340 | H | CF₃ | CN | CH₃ |
| C.341 | CF₃ | CH₃ | H | H |
| C.342 | CF₃ | CH₃ | CH₃ | H |
| C.343 | CF₃ | CH₃ | C₂H₅ | H |
| C.344 | CF₃ | CH₃ | C₃H₇ | H |
| C.345 | CF₃ | CH₃ | C₄H₉ | H |
| C.346 | CF₃ | CH₃ | CH(CH₃)₂ | H |
| C.347 | CF₃ | CH₃ | cyclopropyl | H |
| C.348 | CF₃ | CH₃ | CF₃ | H |
| C.349 | CF₃ | CH₃ | OCH₃ | H |
| C.350 | CF₃ | CH₃ | OC₂H₅ | H |
| C.351 | CF₃ | CH₃ | CH₂—C₆H₅ | H |
| C.352 | CF₃ | CH₃ | CH(CH₃)C₆H₅ | H |
| C.353 | CF₃ | CH₃ | C₆H₅ | H |
| C.354 | CF₃ | CH₃ | 4-F—C₆H₅ | H |
| C.355 | CF₃ | CH₃ | 4-Cl-2-pyridyl | H |
| C.356 | CF₃ | CH₃ | F | H |
| C.357 | CF₃ | CH₃ | CN | H |
| C.358 | CF₃ | CH₃ | H | CH₃ |
| C.359 | CF₃ | CH₃ | CH₃ | CH₃ |
| C.360 | CF₃ | CH₃ | C₂H₅ | CH₃ |
| C.361 | CF₃ | CH₃ | C₃H₇ | CH₃ |
| C.362 | CF₃ | CH₃ | C₄H₉ | CH₃ |
| C.363 | CF₃ | CH₃ | CH(CH₃)₂ | CH₃ |
| C.364 | CF₃ | CH₃ | cyclopropyl | CH₃ |
| C.365 | CF₃ | CH₃ | CF₃ | CH₃ |
| C.366 | CF₃ | CH₃ | OCH₃ | CH₃ |
| C.367 | CF₃ | CH₃ | OC₂H₅ | CH₃ |
| C.368 | CF₃ | CH₃ | CH₂—C₆H₅ | CH₃ |
| C.369 | CF₃ | CH₃ | CH(CH₃)C₆H₅ | CH₃ |
| C.370 | CF₃ | CH₃ | C₆H₅ | CH₃ |
| C.371 | CF₃ | CH₃ | 4-F—C₆H₅ | CH₃ |
| C.372 | CF₃ | CH₃ | 4-Cl-2-pyridyl | CH₃ |
| C.373 | CF₃ | CH₃ | F | CH₃ |
| C.374 | CF₃ | CH₃ | CN | CH₃ |
| C.375 | CF₃ | CF₃ | H | H |
| C.376 | CF₃ | CF₃ | CH₃ | H |
| C.377 | CF₃ | CF₃ | C₂H₅ | H |
| C.378 | CF₃ | CF₃ | C₃H₇ | H |
| C.379 | CF₃ | CF₃ | C₄H₉ | H |
| C.380 | CF₃ | CF₃ | CH(CH₃)₂ | H |
| C.381 | CF₃ | CF₃ | cyclopropyl | H |
| C.382 | CF₃ | CF₃ | CF₃ | H |
| C.383 | CF₃ | CF₃ | OCH₃ | H |
| C.384 | CF₃ | CF₃ | OC₂H₅ | H |
| C.385 | CF₃ | CF₃ | CH₂—C₆H₅ | H |
| C.386 | CF₃ | CF₃ | CH(CH₃)C₆H₅ | H |
| C.387 | CF₃ | CF₃ | C₆H₅ | H |
| C.388 | CF₃ | CF₃ | 4-F—C₆H₅ | H |
| C.389 | CF₃ | CF₃ | 4-Cl-2-pyridyl | H |
| C.390 | CF₃ | CF₃ | F | H |
| C.391 | CF₃ | CF₃ | CN | H |
| C.392 | CF₃ | CF₃ | H | CH₃ |
| C.393 | CF₃ | CF₃ | CH₃ | CH₃ |
| C.394 | CF₃ | CF₃ | C₂H₅ | CH₃ |
| C.395 | CF₃ | CF₃ | C₃H₇ | CH₃ |
| C.396 | CF₃ | CF₃ | C₄H₉ | CH₃ |
| C.397 | CF₃ | CF₃ | CH(CH₃)₂ | CH₃ |
| C.398 | CF₃ | CF₃ | cyclopropyl | CH₃ |
| C.399 | CF₃ | CF₃ | CF₃ | CH₃ |
| C.400 | CF₃ | CF₃ | OCH₃ | CH₃ |
| C.401 | CF₃ | CF₃ | OC₂H₅ | CH₃ |
| C.402 | CF₃ | CF₃ | CH₂—C₆H₅ | CH₃ |
| C.403 | CF₃ | CF₃ | CH(CH₃)C₆H₅ | CH₃ |
| C.404 | CF₃ | CF₃ | C₆H₅ | CH₃ |
| C.405 | CF₃ | CF₃ | 4-F—C₆H₅ | CH₃ |
| C.406 | CF₃ | CF₃ | 4-Cl-2-pyridyl | CH₃ |
| C.407 | CF₃ | CF₃ | F | CH₃ |
| C.408 | CF₃ | CF₃ | CN | CH₃ |
| C.409 | Cl | CH₃ | H | H |
| C.410 | Cl | CH₃ | CH₃ | H |
| C.411 | Cl | CH₃ | C₂H₅ | H |
| C.412 | Cl | CH₃ | C₃H₇ | H |
| C.413 | Cl | CH₃ | C₄H₉ | H |
| C.414 | Cl | CH₃ | CH(CH₃)₂ | H |
| C.415 | Cl | CH₃ | cyclopropyl | H |
| C.416 | Cl | CH₃ | CF₃ | H |
| C.417 | Cl | CH₃ | OCH₃ | H |
| C.418 | Cl | CH₃ | OC₂H₅ | H |

TABLE C-continued

| No. | $R^1$ | $R^x$ | $R^y$ | $R^z$ |
|---|---|---|---|---|
| C.419 | Cl | $CH_3$ | $CH_2-C_6H_5$ | H |
| C.420 | Cl | $CH_3$ | $CH(CH_3)C_6H_5$ | H |
| C.421 | Cl | $CH_3$ | $C_6H_5$ | H |
| C.422 | Cl | $CH_3$ | $4-F-C_6H_5$ | H |
| C.423 | Cl | $CH_3$ | 4-Cl-2-pyridyl | H |
| C.424 | Cl | $CH_3$ | F | H |
| C.425 | Cl | $CH_3$ | CN | H |
| C.426 | Cl | $CH_3$ | H | $CH_3$ |
| C.427 | Cl | $CH_3$ | $CH_3$ | $CH_3$ |
| C.428 | Cl | $CH_3$ | $C_2H_5$ | $CH_3$ |
| C.429 | Cl | $CH_3$ | $C_3H_7$ | $CH_3$ |
| C.430 | Cl | $CH_3$ | $C_4H_9$ | $CH_3$ |
| C.431 | Cl | $CH_3$ | $CH(CH_3)_2$ | $CH_3$ |
| C.432 | Cl | $CH_3$ | cyclopropyl | $CH_3$ |
| C.433 | Cl | $CH_3$ | $CF_3$ | $CH_3$ |
| C.434 | Cl | $CH_3$ | $OCH_3$ | $CH_3$ |
| C.435 | Cl | $CH_3$ | $OC_2H_5$ | $CH_3$ |
| C.436 | Cl | $CH_3$ | $CH_2-C_6H_5$ | $CH_3$ |
| C.437 | Cl | $CH_3$ | $CH(CH_3)C_6H_5$ | $CH_3$ |
| C.438 | Cl | $CH_3$ | $C_6H_5$ | $CH_3$ |
| C.439 | Cl | $CH_3$ | $4-F-C_6H_5$ | $CH_3$ |
| C.440 | Cl | $CH_3$ | 4-Cl-2-pyridyl | $CH_3$ |
| C.441 | Cl | $CH_3$ | F | $CH_3$ |
| C.442 | Cl | $CH_3$ | CN | $CH_3$ |
| C.443 | Cl | $CF_3$ | H | H |
| C.444 | Cl | $CF_3$ | $CH_3$ | H |
| C.445 | Cl | $CF_3$ | $C_2H_5$ | H |
| C.446 | Cl | $CF_3$ | $C_3H_7$ | H |
| C.447 | Cl | $CF_3$ | $C_4H_9$ | H |
| C.448 | Cl | $CF_3$ | $CH(CH_3)_2$ | H |
| C.449 | Cl | $CF_3$ | cyclopropyl | H |
| C.450 | Cl | $CF_3$ | $CF_3$ | H |
| C.451 | Cl | $CF_3$ | $OCH_3$ | H |
| C.452 | Cl | $CF_3$ | $OC_2H_5$ | H |
| C.453 | Cl | $CF_3$ | $CH_2-C_6H_5$ | H |
| C.454 | Cl | $CF_3$ | $CH(CH_3)C_6H_5$ | H |
| C.455 | Cl | $CF_3$ | $C_6H_5$ | H |
| C.456 | Cl | $CF_3$ | $4-F-C_6H_5$ | H |
| C.457 | Cl | $CF_3$ | 4-Cl-2-pyridyl | H |
| C.458 | Cl | $CF_3$ | F | H |
| C.459 | Cl | $CF_3$ | CN | H |
| C.460 | Cl | $CF_3$ | H | $CH_3$ |
| C.461 | Cl | $CF_3$ | $CH_3$ | $CH_3$ |
| C.462 | Cl | $CF_3$ | $C_2H_5$ | $CH_3$ |
| C.463 | Cl | $CF_3$ | $C_3H_7$ | $CH_3$ |
| C.464 | Cl | $CF_3$ | $C_4H_9$ | $CH_3$ |
| C.465 | Cl | $CF_3$ | $CH(CH_3)_2$ | $CH_3$ |
| C.466 | Cl | $CF_3$ | cyclopropyl | $CH_3$ |
| C.467 | Cl | $CF_3$ | $CF_3$ | $CH_3$ |
| C.468 | Cl | $CF_3$ | $OCH_3$ | $CH_3$ |
| C.469 | Cl | $CF_3$ | $OC_2H_5$ | $CH_3$ |
| C.470 | Cl | $CF_3$ | $CH_2-C_6H_5$ | $CH_3$ |
| C.471 | Cl | $CF_3$ | $CH(CH_3)C_6H_5$ | $CH_3$ |
| C.472 | Cl | $CF_3$ | $C_6H_5$ | $CH_3$ |
| C.473 | Cl | $CF_3$ | $4-F-C_6H_5$ | $CH_3$ |
| C.474 | Cl | $CF_3$ | 4-Cl-2-pyridyl | $CH_3$ |
| C.475 | Cl | $CF_3$ | F | $CH_3$ |
| C.476 | Cl | $CF_3$ | CN | $CH_3$ |
| C.477 | H | $CH_3$ | H | F |
| C.478 | H | $CH_3$ | $CH_3$ | F |
| C.479 | H | $CH_3$ | $C_2H_5$ | F |
| C.480 | H | $CH_3$ | $C_3H_7$ | F |
| C.481 | H | $CH_3$ | $CH(CH_3)_2$ | F |
| C.482 | H | $CH_3$ | cyclopropyl | F |
| C.483 | H | $CH_3$ | $CF_3$ | F |
| C.484 | H | $CH_3$ | $OCH_3$ | F |
| C.485 | H | $CH_3$ | $C_6H_5$ | F |
| C.486 | H | $CH_3$ | $4-F-C_6H_5$ | F |
| C.487 | H | $CH_3$ | H | $C_2H_5$ |
| C.488 | H | $CH_3$ | $CH_3$ | $C_2H_5$ |
| C.489 | H | $CH_3$ | $C_2H_5$ | $C_2H_5$ |
| C.490 | H | $CH_3$ | $C_3H_7$ | $C_2H_5$ |
| C.491 | H | $CH_3$ | $CH(CH_3)_2$ | $C_2H_5$ |
| C.492 | H | $CH_3$ | cyclopropyl | $C_2H_5$ |
| C.493 | H | $CH_3$ | $CF_3$ | $C_2H_5$ |
| C.494 | H | $CH_3$ | $OCH_3$ | $C_2H_5$ |
| C.495 | H | $CH_3$ | $C_6H_5$ | $C_2H_5$ |
| C.496 | H | $CH_3$ | $4-F-C_6H_5$ | $C_2H_5$ |
| C.497 | H | $CH_3$ | H | $CF_3$ |
| C.498 | H | $CH_3$ | $CH_3$ | $CF_3$ |
| C.499 | H | $CH_3$ | $C_2H_5$ | $CF_3$ |
| C.500 | H | $CH_3$ | $C_3H_7$ | $CF_3$ |
| C.501 | H | $CH_3$ | $CH(CH_3)_2$ | $CF_3$ |
| C.502 | H | $CH_3$ | cyclopropyl | $CF_3$ |
| C.503 | H | $CH_3$ | $CF_3$ | $CF_3$ |
| C.504 | H | $CH_3$ | $OCH_3$ | $CF_3$ |
| C.505 | H | $CH_3$ | $C_6H_5$ | $CF_3$ |
| C.506 | H | $CH_3$ | $4-F-C_6H_5$ | $CF_3$ |
| C.507 | H | $CH_3$ | H | CN |
| C.508 | H | $CH_3$ | $CH_3$ | CN |
| C.509 | H | $CH_3$ | $C_2H_5$ | CN |
| C.510 | H | $CH_3$ | $C_3H_7$ | CN |
| C.511 | H | $CH_3$ | $CH(CH_3)_2$ | CN |
| C.512 | H | $CH_3$ | cyclopropyl | CN |
| C.513 | H | $CH_3$ | $CF_3$ | CN |
| C.514 | H | $CH_3$ | $OCH_3$ | CN |
| C.515 | H | $CH_3$ | $C_6H_5$ | CN |
| C.516 | H | $CH_3$ | $4-F-C_6H_5$ | CN |
| C.517 | H | $CH_3$ | H | Cl |
| C.518 | H | $CH_3$ | $CH_3$ | Cl |
| C.519 | H | $CH_3$ | $C_2H_5$ | Cl |
| C.520 | H | $CH_3$ | $C_3H_7$ | Cl |
| C.521 | H | $CH_3$ | $CH(CH_3)_2$ | Cl |
| C.522 | H | $CH_3$ | cyclopropyl | Cl |
| C.523 | H | $CH_3$ | $CF_3$ | Cl |
| C.524 | H | $CH_3$ | $OCH_3$ | Cl |
| C.525 | H | $CH_3$ | $C_6H_5$ | Cl |
| C.526 | H | $CH_3$ | $4-F-C_6H_5$ | Cl |
| C.527 | H | $CF_3$ | H | F |
| C.528 | H | $CF_3$ | $CH_3$ | F |
| C.529 | H | $CF_3$ | $C_2H_5$ | F |
| C.530 | H | $CF_3$ | $C_3H_7$ | F |
| C.531 | H | $CF_3$ | $CH(CH_3)_2$ | F |
| C.532 | H | $CF_3$ | cyclopropyl | F |
| C.533 | H | $CF_3$ | $CF_3$ | F |
| C.534 | H | $CF_3$ | $OCH_3$ | F |
| C.535 | H | $CF_3$ | $C_6H_5$ | F |
| C.536 | H | $CF_3$ | $4-F-C_6H_5$ | F |
| C.537 | H | $CF_3$ | H | $C_2H_5$ |
| C.538 | H | $CF_3$ | $CH_3$ | $C_2H_5$ |
| C.539 | H | $CF_3$ | $C_2H_5$ | $C_2H_5$ |
| C.540 | H | $CF_3$ | $C_3H_7$ | $C_2H_5$ |
| C.541 | H | $CF_3$ | $CH(CH_3)_2$ | $C_2H_5$ |
| C.542 | H | $CF_3$ | cyclopropyl | $C_2H_5$ |
| C.543 | H | $CF_3$ | $CF_3$ | $C_2H_5$ |
| C.544 | H | $CF_3$ | $OCH_3$ | $C_2H_5$ |
| C.545 | H | $CF_3$ | $C_6H_5$ | $C_2H_5$ |
| C.546 | H | $CF_3$ | $4-F-C_6H_5$ | $C_2H_5$ |
| C.547 | H | $CF_3$ | H | $CF_3$ |
| C.548 | H | $CF_3$ | $CH_3$ | $CF_3$ |
| C.549 | H | $CF_3$ | $C_2H_5$ | $CF_3$ |
| C.550 | H | $CF_3$ | $C_3H_7$ | $CF_3$ |
| C.551 | H | $CF_3$ | $CH(CH_3)_2$ | $CF_3$ |
| C.552 | H | $CF_3$ | cyclopropyl | $CF_3$ |
| C.553 | H | $CF_3$ | $CF_3$ | $CF_3$ |
| C.554 | H | $CF_3$ | $OCH_3$ | $CF_3$ |
| C.555 | H | $CF_3$ | $C_6H_5$ | $CF_3$ |
| C.556 | H | $CF_3$ | $4-F-C_6H_5$ | $CF_3$ |
| C.557 | H | $CF_3$ | H | CN |
| C.558 | H | $CF_3$ | $CH_3$ | CN |
| C.559 | H | $CF_3$ | $C_2H_5$ | CN |
| C.560 | H | $CF_3$ | $C_3H_7$ | CN |
| C.561 | H | $CF_3$ | $CH(CH_3)_2$ | CN |
| C.562 | H | $CF_3$ | cyclopropyl | CN |
| C.563 | H | $CF_3$ | $CF_3$ | CN |
| C.564 | H | $CF_3$ | $OCH_3$ | CN |
| C.565 | H | $CF_3$ | $C_6H_5$ | CN |
| C.566 | H | $CF_3$ | $4-F-C_6H_5$ | CN |
| C.567 | H | $CF_3$ | H | Cl |
| C.568 | H | $CF_3$ | $CH_3$ | Cl |
| C.569 | H | $CF_3$ | $C_2H_5$ | Cl |
| C.570 | H | $CF_3$ | $C_3H_7$ | Cl |
| C.571 | H | $CF_3$ | $CH(CH_3)_2$ | Cl |
| C.572 | H | $CF_3$ | cyclopropyl | Cl |

TABLE C-continued

| No. | $R^1$ | $R^x$ | $R^y$ | $R^z$ |
|---|---|---|---|---|
| C.573 | H | $CF_3$ | $CF_3$ | Cl |
| C.574 | H | $CF_3$ | $OCH_3$ | Cl |
| C.575 | H | $CF_3$ | $C_6H_5$ | Cl |
| C.576 | H | $CF_3$ | 4-F—$C_6H_5$ | Cl |
| C.577 | $CF_3$ | $CH_3$ | H | F |
| C.578 | $CF_3$ | $CH_3$ | $CH_3$ | F |
| C.579 | $CF_3$ | $CH_3$ | $C_2H_5$ | F |
| C.580 | $CF_3$ | $CH_3$ | $C_3H_7$ | F |
| C.581 | $CF_3$ | $CH_3$ | $CH(CH_3)_2$ | F |
| C.582 | $CF_3$ | $CH_3$ | cyclopropyl | F |
| C.583 | $CF_3$ | $CH_3$ | $CF_3$ | F |
| C.584 | $CF_3$ | $CH_3$ | $OCH_3$ | F |
| C.585 | $CF_3$ | $CH_3$ | $C_6H_5$ | F |
| C.586 | $CF_3$ | $CH_3$ | 4-F—$C_6H_5$ | F |
| C.587 | $CF_3$ | $CH_3$ | H | $C_2H_5$ |
| C.588 | $CF_3$ | $CH_3$ | $CH_3$ | $C_2H_5$ |
| C.589 | $CF_3$ | $CH_3$ | $C_2H_5$ | $C_2H_5$ |
| C.590 | $CF_3$ | $CH_3$ | $C_3H_7$ | $C_2H_5$ |
| C.591 | $CF_3$ | $CH_3$ | $CH(CH_3)_2$ | $C_2H_5$ |
| C.592 | $CF_3$ | $CH_3$ | cyclopropyl | $C_2H_5$ |
| C.593 | $CF_3$ | $CH_3$ | $CF_3$ | $C_2H_5$ |
| C.594 | $CF_3$ | $CH_3$ | $OCH_3$ | $C_2H_5$ |
| C.595 | $CF_3$ | $CH_3$ | $C_6H_5$ | $C_2H_5$ |
| C.596 | $CF_3$ | $CH_3$ | 4-F—$C_6H_5$ | $C_2H_5$ |
| C.597 | $CF_3$ | $CH_3$ | H | $CF_3$ |
| C.598 | $CF_3$ | $CH_3$ | $CH_3$ | $CF_3$ |
| C.599 | $CF_3$ | $CH_3$ | $C_2H_5$ | $CF_3$ |
| C.600 | $CF_3$ | $CH_3$ | $C_3H_7$ | $CF_3$ |
| C.601 | $CF_3$ | $CH_3$ | $CH(CH_3)_2$ | $CF_3$ |
| C.602 | $CF_3$ | $CH_3$ | cyclopropyl | $CF_3$ |
| C.603 | $CF_3$ | $CH_3$ | $CF_3$ | $CF_3$ |
| C.604 | $CF_3$ | $CH_3$ | $OCH_3$ | $CF_3$ |
| C.605 | $CF_3$ | $CH_3$ | $C_6H_5$ | $CF_3$ |
| C.606 | $CF_3$ | $CH_3$ | 4-F—$C_6H_5$ | $CF_3$ |
| C.607 | $CF_3$ | $CH_3$ | H | CN |
| C.608 | $CF_3$ | $CH_3$ | $CH_3$ | CN |
| C.609 | $CF_3$ | $CH_3$ | $C_2H_5$ | CN |
| C.610 | $CF_3$ | $CH_3$ | $C_3H_7$ | CN |
| C.611 | $CF_3$ | $CH_3$ | $CH(CH_3)_2$ | CN |
| C.612 | $CF_3$ | $CH_3$ | cyclopropyl | CN |
| C.613 | $CF_3$ | $CH_3$ | $CF_3$ | CN |
| C.614 | $CF_3$ | $CH_3$ | $OCH_3$ | CN |
| C.615 | $CF_3$ | $CH_3$ | $C_6H_5$ | CN |
| C.616 | $CF_3$ | $CH_3$ | 4-F—$C_6H_5$ | CN |
| C.617 | $CF_3$ | $CH_3$ | H | Cl |
| C.618 | $CF_3$ | $CH_3$ | $CH_3$ | Cl |
| C.619 | $CF_3$ | $CH_3$ | $C_2H_5$ | Cl |
| C.620 | $CF_3$ | $CH_3$ | $C_3H_7$ | Cl |
| C.621 | $CF_3$ | $CH_3$ | $CH(CH_3)_2$ | Cl |
| C.622 | $CF_3$ | $CH_3$ | cyclopropyl | Cl |
| C.623 | $CF_3$ | $CH_3$ | $CF_3$ | Cl |
| C.624 | $CF_3$ | $CH_3$ | $OCH_3$ | Cl |
| C.625 | $CF_3$ | $CH_3$ | $C_6H_5$ | Cl |
| C.626 | $CF_3$ | $CH_3$ | 4-F—$C_6H_5$ | Cl |
| C.627 | $CF_3$ | $CF_3$ | H | F |
| C.628 | $CF_3$ | $CF_3$ | $CH_3$ | F |
| C.629 | $CF_3$ | $CF_3$ | $C_2H_5$ | F |
| C.630 | $CF_3$ | $CF_3$ | $C_3H_7$ | F |
| C.631 | $CF_3$ | $CF_3$ | $CH(CH_3)_2$ | F |
| C.632 | $CF_3$ | $CF_3$ | cyclopropyl | F |
| C.633 | $CF_3$ | $CF_3$ | $CF_3$ | F |
| C.634 | $CF_3$ | $CF_3$ | $OCH_3$ | F |
| C.635 | $CF_3$ | $CF_3$ | $C_6H_5$ | F |
| C.636 | $CF_3$ | $CF_3$ | 4-F—$C_6H_5$ | F |
| C.637 | $CF_3$ | $CF_3$ | H | $C_2H_5$ |
| C.638 | $CF_3$ | $CF_3$ | $CH_3$ | $C_2H_5$ |
| C.639 | $CF_3$ | $CF_3$ | $C_2H_5$ | $C_2H_5$ |
| C.640 | $CF_3$ | $CF_3$ | $C_3H_7$ | $C_2H_5$ |
| C.641 | $CF_3$ | $CF_3$ | $CH(CH_3)_2$ | $C_2H_5$ |
| C.642 | $CF_3$ | $CF_3$ | cyclopropyl | $C_2H_5$ |
| C.643 | $CF_3$ | $CF_3$ | $CF_3$ | $C_2H_5$ |
| C.644 | $CF_3$ | $CF_3$ | $OCH_3$ | $C_2H_5$ |
| C.645 | $CF_3$ | $CF_3$ | $C_6H_5$ | $C_2H_5$ |
| C.646 | $CF_3$ | $CF_3$ | 4-F—$C_6H_5$ | $C_2H_5$ |
| C.647 | $CF_3$ | $CF_3$ | H | $CF_3$ |
| C.648 | $CF_3$ | $CF_3$ | $CH_3$ | $CF_3$ |
| C.649 | $CF_3$ | $CF_3$ | $C_2H_5$ | $CF_3$ |
| C.650 | $CF_3$ | $CF_3$ | $C_3H_7$ | $CF_3$ |
| C.651 | $CF_3$ | $CF_3$ | $CH(CH_3)_2$ | $CF_3$ |
| C.652 | $CF_3$ | $CF_3$ | cyclopropyl | $CF_3$ |
| C.653 | $CF_3$ | $CF_3$ | $CF_3$ | $CF_3$ |
| C.654 | $CF_3$ | $CF_3$ | $OCH_3$ | $CF_3$ |
| C.655 | $CF_3$ | $CF_3$ | $C_6H_5$ | $CF_3$ |
| C.656 | $CF_3$ | $CF_3$ | 4-F—$C_6H_5$ | $CF_3$ |
| C.657 | $CF_3$ | $CF_3$ | H | CN |
| C.658 | $CF_3$ | $CF_3$ | $CH_3$ | CN |
| C.659 | $CF_3$ | $CF_3$ | $C_2H_5$ | CN |
| C.660 | $CF_3$ | $CF_3$ | $C_3H_7$ | CN |
| C.661 | $CF_3$ | $CF_3$ | $CH(CH_3)_2$ | CN |
| C.662 | $CF_3$ | $CF_3$ | cyclopropyl | CN |
| C.663 | $CF_3$ | $CF_3$ | $CF_3$ | CN |
| C.664 | $CF_3$ | $CF_3$ | $OCH_3$ | CN |
| C.665 | $CF_3$ | $CF_3$ | $C_6H_5$ | CN |
| C.666 | $CF_3$ | $CF_3$ | 4-F—$C_6H_5$ | CN |
| C.667 | $CF_3$ | $CF_3$ | H | Cl |
| C.668 | $CF_3$ | $CF_3$ | $CH_3$ | Cl |
| C.669 | $CF_3$ | $CF_3$ | $C_2H_5$ | Cl |
| C.670 | $CF_3$ | $CF_3$ | $C_3H_7$ | Cl |
| C.671 | $CF_3$ | $CF_3$ | $CH(CH_3)_2$ | Cl |
| C.672 | $CF_3$ | $CF_3$ | cyclopropyl | Cl |
| C.673 | $CF_3$ | $CF_3$ | $CF_3$ | Cl |
| C.674 | $CF_3$ | $CF_3$ | $OCH_3$ | Cl |
| C.675 | $CF_3$ | $CF_3$ | $C_6H_5$ | Cl |
| C.676 | $CF_3$ | $CF_3$ | 4-F—$C_6H_5$ | Cl |
| C.677 | Cl | $CH_3$ | H | F |
| C.678 | Cl | $CH_3$ | $CH_3$ | F |
| C.679 | Cl | $CH_3$ | $C_2H_5$ | F |
| C.680 | Cl | $CH_3$ | $C_3H_7$ | F |
| C.681 | Cl | $CH_3$ | $CH(CH_3)_2$ | F |
| C.682 | Cl | $CH_3$ | cyclopropyl | F |
| C.683 | Cl | $CH_3$ | $CF_3$ | F |
| C.684 | Cl | $CH_3$ | $OCH_3$ | F |
| C.685 | Cl | $CH_3$ | $C_6H_5$ | F |
| C.686 | Cl | $CH_3$ | 4-F—$C_6H_5$ | F |
| C.687 | Cl | $CH_3$ | H | $C_2H_5$ |
| C.688 | Cl | $CH_3$ | $CH_3$ | $C_2H_5$ |
| C.689 | Cl | $CH_3$ | $C_2H_5$ | $C_2H_5$ |
| C.690 | Cl | $CH_3$ | $C_3H_7$ | $C_2H_5$ |
| C.691 | Cl | $CH_3$ | $CH(CH_3)_2$ | $C_2H_5$ |
| C.692 | Cl | $CH_3$ | cyclopropyl | $C_2H_5$ |
| C.693 | Cl | $CH_3$ | $CF_3$ | $C_2H_5$ |
| C.694 | Cl | $CH_3$ | $OCH_3$ | $C_2H_5$ |
| C.695 | Cl | $CH_3$ | $C_6H_5$ | $C_2H_5$ |
| C.696 | Cl | $CH_3$ | 4-F—$C_6H_5$ | $C_2H_5$ |
| C.697 | Cl | $CH_3$ | H | $CF_3$ |
| C.698 | Cl | $CH_3$ | $CH_3$ | $CF_3$ |
| C.699 | Cl | $CH_3$ | $C_2H_5$ | $CF_3$ |
| C.700 | Cl | $CH_3$ | $C_3H_7$ | $CF_3$ |
| C.701 | Cl | $CH_3$ | $CH(CH_3)_2$ | $CF_3$ |
| C.702 | Cl | $CH_3$ | cyclopropyl | $CF_3$ |
| C.703 | Cl | $CH_3$ | $CF_3$ | $CF_3$ |
| C.704 | Cl | $CH_3$ | $OCH_3$ | $CF_3$ |
| C.705 | Cl | $CH_3$ | $C_6H_5$ | $CF_3$ |
| C.706 | Cl | $CH_3$ | 4-F—$C_6H_5$ | $CF_3$ |
| C.707 | Cl | $CH_3$ | H | CN |
| C.708 | Cl | $CH_3$ | $CH_3$ | CN |
| C.709 | Cl | $CH_3$ | $C_2H_5$ | CN |
| C.710 | Cl | $CH_3$ | $C_3H_7$ | CN |
| C.711 | Cl | $CH_3$ | $CH(CH_3)_2$ | CN |
| C.712 | Cl | $CH_3$ | cyclopropyl | CN |
| C.713 | Cl | $CH_3$ | $CF_3$ | CN |
| C.714 | Cl | $CH_3$ | $OCH_3$ | CN |
| C.715 | Cl | $CH_3$ | $C_6H_5$ | CN |
| C.716 | Cl | $CH_3$ | 4-F—$C_6H_5$ | CN |
| C.717 | Cl | $CH_3$ | H | Cl |
| C.718 | Cl | $CH_3$ | $CH_3$ | Cl |
| C.719 | Cl | $CH_3$ | $C_2H_5$ | Cl |
| C.720 | Cl | $CH_3$ | $C_3H_7$ | Cl |
| C.721 | Cl | $CH_3$ | $CH(CH_3)_2$ | Cl |
| C.722 | Cl | $CH_3$ | cyclopropyl | Cl |
| C.723 | Cl | $CH_3$ | $CF_3$ | Cl |
| C.724 | Cl | $CH_3$ | $OCH_3$ | Cl |
| C.725 | Cl | $CH_3$ | $C_6H_5$ | Cl |
| C.726 | Cl | $CH_3$ | 4-F—$C_6H_5$ | Cl |

TABLE C-continued

| No. | R¹ | Rˣ | Rʸ | Rᶻ |
|---|---|---|---|---|
| C.727 | Cl | CF₃ | H | F |
| C.728 | Cl | CF₃ | CH₃ | F |
| C.729 | Cl | CF₃ | C₂H₅ | F |
| C.730 | Cl | CF₃ | C₃H₇ | F |
| C.731 | Cl | CF₃ | CH(CH₃)₂ | F |
| C.732 | Cl | CF₃ | cyclopropyl | F |
| C.733 | Cl | CF₃ | CF₃ | F |
| C.734 | Cl | CF₃ | OCH₃ | F |
| C.735 | Cl | CF₃ | C₆H₅ | F |
| C.736 | Cl | CF₃ | 4-F—C₆H₅ | F |
| C.737 | Cl | CF₃ | H | C₂H₅ |
| C.738 | Cl | CF₃ | CH₃ | C₂H₅ |
| C.739 | Cl | CF₃ | C₂H₅ | C₂H₅ |
| C.740 | Cl | CF₃ | C₃H₇ | C₂H₅ |
| C.741 | Cl | CF₃ | CH(CH₃)₂ | C₂H₅ |
| C.742 | Cl | CF₃ | cyclopropyl | C₂H₅ |
| C.743 | Cl | CF₃ | CF₃ | C₂H₅ |
| C.744 | Cl | CF₃ | OCH₃ | C₂H₅ |
| C.745 | Cl | CF₃ | C₆H₅ | C₂H₅ |
| C.746 | Cl | CF₃ | 4-F—C₆H₅ | C₂H₅ |
| C.747 | Cl | CF₃ | H | CF₃ |
| C.748 | Cl | CF₃ | CH₃ | CF₃ |
| C.749 | Cl | CF₃ | C₂H₅ | CF₃ |
| C.750 | Cl | CF₃ | C₃H₇ | CF₃ |
| C.751 | Cl | CF₃ | CH(CH₃)₂ | CF₃ |
| C.752 | Cl | CF₃ | cyclopropyl | CF₃ |
| C.753 | Cl | CF₃ | CF₃ | CF₃ |
| C.754 | Cl | CF₃ | OCH₃ | CF₃ |
| C.755 | Cl | CF₃ | C₆H₅ | CF₃ |
| C.756 | Cl | CF₃ | 4-F—C₆H₅ | CF₃ |
| C.757 | Cl | CF₃ | H | CN |
| C.758 | Cl | CF₃ | CH₃ | CN |
| C.759 | Cl | CF₃ | C₂H₅ | CN |
| C.760 | Cl | CF₃ | C₃H₇ | CN |
| C.761 | Cl | CF₃ | CH(CH₃)₂ | CN |
| C.762 | Cl | CF₃ | cyclopropyl | CN |
| C.763 | Cl | CF₃ | CF₃ | CN |
| C.764 | Cl | CF₃ | OCH₃ | CN |
| C.765 | Cl | CF₃ | C₆H₅ | CN |
| C.766 | Cl | CF₃ | 4-F—C₆H₅ | CN |
| C.767 | Cl | CF₃ | H | Cl |
| C.768 | Cl | CF₃ | CH₃ | Cl |
| C.769 | Cl | CF₃ | C₂H₅ | Cl |
| C.770 | Cl | CF₃ | C₃H₇ | Cl |
| C.771 | Cl | CF₃ | CH(CH₃)₂ | Cl |
| C.772 | Cl | CF₃ | cyclopropyl | Cl |
| C.773 | Cl | CF₃ | CF₃ | Cl |
| C.774 | Cl | CF₃ | OCH₃ | Cl |
| C.775 | Cl | CF₃ | C₆H₅ | Cl |
| C.776 | Cl | CF₃ | 4-F—C₆H₅ | Cl |
| C.777 | CH₃ | H | H | F |
| C.778 | CH₃ | H | CH₃ | F |
| C.779 | CH₃ | H | C₂H₅ | F |
| C.780 | CH₃ | H | C₃H₇ | F |
| C.781 | CH₃ | H | CH(CH₃)₂ | F |
| C.782 | CH₃ | H | cyclopropyl | F |
| C.783 | CH₃ | H | CF₃ | F |
| C.784 | CH₃ | H | OCH₃ | F |
| C.785 | CH₃ | H | C₆H₅ | F |
| C.786 | CH₃ | H | 4-F—C₆H₅ | F |
| C.787 | CH₃ | CH₃ | H | F |
| C.788 | CH₃ | CH₃ | CH₃ | F |
| C.789 | CH₃ | CH₃ | C₂H₅ | F |
| C.790 | CH₃ | CH₃ | C₃H₇ | F |
| C.791 | CH₃ | CH₃ | CH(CH₃)₂ | F |
| C.792 | CH₃ | CH₃ | cyclopropyl | F |
| C.793 | CH₃ | CH₃ | CF₃ | F |
| C.794 | CH₃ | CH₃ | OCH₃ | F |
| C.795 | CH₃ | CH₃ | C₆H₅ | F |
| C.796 | CH₃ | CH₃ | 4-F—C₆H₅ | F |
| C.797 | CH₃ | C₂H₅ | H | F |
| C.798 | CH₃ | C₂H₅ | CH₃ | F |
| C.799 | CH₃ | C₂H₅ | C₂H₅ | F |
| C.800 | CH₃ | C₂H₅ | C₃H₇ | F |
| C.801 | CH₃ | C₂H₅ | CH(CH₃)₂ | F |
| C.802 | CH₃ | C₂H₅ | cyclopropyl | F |
| C.803 | CH₃ | C₂H₅ | CF₃ | F |
| C.804 | CH₃ | C₂H₅ | OCH₃ | F |
| C.805 | CH₃ | C₂H₅ | C₆H₅ | F |
| C.806 | CH₃ | C₂H₅ | 4-F—C₆H₅ | F |
| C.807 | CH₃ | cyclopropyl | H | F |
| C.808 | CH₃ | cyclopropyl | CH₃ | F |
| C.809 | CH₃ | cyclopropyl | C₂H₅ | F |
| C.810 | CH₃ | cyclopropyl | C₃H₇ | F |
| C.811 | CH₃ | cyclopropyl | CH(CH₃)₂ | F |
| C.812 | CH₃ | cyclopropyl | cyclopropyl | F |
| C.813 | CH₃ | cyclopropyl | CF₃ | F |
| C.814 | CH₃ | cyclopropyl | OCH₃ | F |
| C.815 | CH₃ | cyclopropyl | C₆H₅ | F |
| C.816 | CH₃ | cyclopropyl | 4-F—C₆H₅ | F |
| C.817 | CH₃ | CF₃ | H | F |
| C.818 | CH₃ | CF₃ | CH₃ | F |
| C.819 | CH₃ | CF₃ | C₂H₅ | F |
| C.820 | CH₃ | CF₃ | C₃H₇ | F |
| C.821 | CH₃ | CF₃ | CH(CH₃)₂ | F |
| C.822 | CH₃ | CF₃ | cyclopropyl | F |
| C.823 | CH₃ | CF₃ | CF₃ | F |
| C.824 | CH₃ | CF₃ | OCH₃ | F |
| C.825 | CH₃ | CF₃ | C₆H₅ | F |
| C.826 | CH₃ | CF₃ | 4-F—C₆H₅ | F |
| C.827 | CH₃ | Cl | H | F |
| C.828 | CH₃ | Cl | CH₃ | F |
| C.829 | dH3 | Cl | C₂H₅ | F |
| C.830 | CH₃ | Cl | C₃H₇ | F |
| C.831 | CH₃ | Cl | CH(CH₃)₂ | F |
| C.832 | CH₃ | Cl | cyclopropyl | F |
| C.833 | CH₃ | Cl | CF₃ | F |
| C.834 | CH₃ | Cl | OCH₃ | F |
| C.835 | CH₃ | Cl | C₆H₅ | F |
| C.836 | CH₃ | Cl | 4-F—C₆H₅ | F |
| C.837 | CH₃ | F | H | F |
| C.838 | CH₃ | F | CH₃ | F |
| C.839 | CH₃ | F | C₂H₅ | F |
| C.840 | CH₃ | F | C₃H₇ | F |
| C.841 | CH₃ | F | CH(CH₃)₂ | F |
| C.842 | CH₃ | F | cyclopropyl | F |
| C.843 | CH₃ | F | CF₃ | F |
| C.844 | CH₃ | F | OCH₃ | F |
| C.845 | CH₃ | F | C₆H₅ | F |
| C.846 | CH₃ | F | 4-F—C₆H₅ | F |
| C.847 | CH₃ | OCH₃ | H | F |
| C.848 | CH₃ | OCH₃ | CH₃ | F |
| C.849 | CH₃ | OCH₃ | C₂H₅ | F |
| C.850 | CH₃ | OCH₃ | C₃H₇ | F |
| C.851 | CH₃ | OCH₃ | CH(CH₃)₂ | F |
| C.852 | CH₃ | OCH₃ | cyclopropyl | F |
| C.853 | CH₃ | OCH₃ | CF₃ | F |
| C.854 | CH₃ | OCH₃ | OCH₃ | F |
| C.855 | CH₃ | OCH₃ | C₆H₅ | F |
| C.856 | CH₃ | OCH₃ | 4-F—C₆H₅ | F |
| C.857 | CH₃ | H | H | C₂H₅ |
| C.858 | CH₃ | H | CH₃ | C₂H₅ |
| C.859 | CH₃ | H | C₂H₅ | C₂H₅ |
| C.860 | CH₃ | H | C₃H₇ | C₂H₅ |
| C.861 | CH₃ | H | CH(CH₃)₂ | C₂H₅ |
| C.862 | CH₃ | H | cyclopropyl | C₂H₅ |
| C.863 | CH₃ | H | CF₃ | C₂H₅ |
| C.864 | CH₃ | H | OCH₃ | C₂H₅ |
| C.865 | CH₃ | H | C₆H₅ | C₂H₅ |
| C.866 | CH₃ | H | 4-F—C₆H₅ | C₂H₅ |
| C.867 | CH₃ | CH₃ | H | C₂H₅ |
| C.868 | CH₃ | CH₃ | CH₃ | C₂H₅ |
| C.869 | CH₃ | CH₃ | C₂H₅ | C₂H₅ |
| C.870 | CH₃ | CH₃ | C₃H₇ | C₂H₅ |
| C.871 | CH₃ | CH₃ | CH(CH₃)₂ | C₂H₅ |
| C.872 | CH₃ | CH₃ | cyclopropyl | C₂H₅ |
| C.873 | CH₃ | CH₃ | CF₃ | C₂H₅ |
| C.874 | CH₃ | CH₃ | OCH₃ | C₂H₅ |
| C.875 | CH₃ | CH₃ | C₆H₅ | C₂H₅ |
| C.876 | CH₃ | CH₃ | 4-F—C₆H₅ | C₂H₅ |
| C.877 | CH₃ | C₂H₅ | H | C₂H₅ |
| C.878 | CH₃ | C₂H₅ | CH₃ | C₂H₅ |
| C.879 | CH₃ | C₂H₅ | C₂H₅ | C₂H₅ |
| C.880 | CH₃ | C₂H₅ | C₃H₇ | C₂H₅ |

TABLE C-continued

| No. | R¹ | Rˣ | Rʸ | Rᶻ |
|---|---|---|---|---|
| C.881 | $CH_3$ | $C_2H_5$ | $CH(CH_3)_2$ | $C_2H_5$ |
| C.882 | $CH_3$ | $C_2H_5$ | cyclopropyl | $C_2H_5$ |
| C.883 | $CH_3$ | $C_2H_5$ | $CF_3$ | $C_2H_5$ |
| C.884 | $CH_3$ | $C_2H_5$ | $OCH_3$ | $C_2H_5$ |
| C.885 | $CH_3$ | $C_2H_5$ | $C_6H_5$ | $C_2H_5$ |
| C.886 | $CH_3$ | $C_2H_5$ | 4-F—$C_6H_5$ | $C_2H_5$ |
| C.887 | $CH_3$ | cyclopropyl | H | $C_2H_5$ |
| C.888 | $CH_3$ | cyclopropyl | $CH_3$ | $C_2H_5$ |
| C.889 | $CH_3$ | cyclopropyl | $C_2H_5$ | $C_2H_5$ |
| C.890 | $CH_3$ | cyclopropyl | $C_3H_7$ | $C_2H_5$ |
| C.891 | $CH_3$ | cyclopropyl | $CH(CH_3)_2$ | $C_2H_5$ |
| C.892 | $CH_3$ | cyclopropyl | cyclopropyl | $C_2H_5$ |
| C.893 | $CH_3$ | cyclopropyl | $CF_3$ | $C_2H_5$ |
| C.894 | $CH_3$ | cyclopropyl | $OCH_3$ | $C_2H_5$ |
| C.895 | $CH_3$ | cyclopropyl | $C_6H_5$ | $C_2H_5$ |
| C.896 | $CH_3$ | cyclopropyl | 4-F—$C_6H_5$ | $C_2H_5$ |
| C.897 | $CH_3$ | $CF_3$ | H | $C_2H_5$ |
| C.898 | $CH_3$ | $CF_3$ | $CH_3$ | $C_2H_5$ |
| C.899 | $CH_3$ | $CF_3$ | $C_2H_5$ | $C_2H_5$ |
| C.900 | $CH_3$ | $CF_3$ | $C_3H_7$ | $C_2H_5$ |
| C.901 | $CH_3$ | $CF_3$ | $CH(CH_3)_2$ | $C_2H_5$ |
| C.902 | $CH_3$ | $CF_3$ | cyclopropyl | $C_2H_5$ |
| C.903 | $CH_3$ | $CF_3$ | $CF_3$ | $C_2H_5$ |
| C.904 | $CH_3$ | $CF_3$ | $OCH_3$ | $C_2H_5$ |
| C.905 | $CH_3$ | $CF_3$ | $C_6H_5$ | $C_2H_5$ |
| C.906 | $CH_3$ | $CF_3$ | 4-F—$C_6H_5$ | $C_2H_5$ |
| C.907 | $CH_3$ | Cl | H | $C_2H_5$ |
| C.908 | $CH_3$ | Cl | $CH_3$ | $C_2H_5$ |
| C.909 | $CH_3$ | Cl | $C_2H_5$ | $C_2H_5$ |
| C.910 | $CH_3$ | Cl | $C_3H_7$ | $C_2H_5$ |
| C.911 | $CH_3$ | Cl | $CH(CH_3)_2$ | $C_2H_5$ |
| C.912 | $CH_3$ | Cl | cyclopropyl | $C_2H_5$ |
| C.913 | $CH_3$ | Cl | $CF_3$ | $C_2H_5$ |
| C.914 | $CH_3$ | Cl | $OCH_3$ | $C_2H_5$ |
| C.915 | $CH_3$ | Cl | $C_6H_5$ | $C_2H_5$ |
| C.916 | $CH_3$ | Cl | 4-F—$C_6H_5$ | $C_2H_5$ |
| C.917 | $CH_3$ | F | H | $C_2H_5$ |
| C.918 | $CH_3$ | F | $CH_3$ | $C_2H_5$ |
| C.919 | $CH_3$ | F | $C_2H_5$ | $C_2H_5$ |
| C.920 | $CH_3$ | F | $C_3H_7$ | $C_2H_5$ |
| C.921 | $CH_3$ | F | $CH(CH_3)_2$ | $C_2H_5$ |
| C.922 | $CH_3$ | F | cyclopropyl | $C_2H_5$ |
| C.923 | $CH_3$ | F | $CF_3$ | $C_2H_5$ |
| C.924 | $CH_3$ | F | $OCH_3$ | $C_2H_5$ |
| C.925 | $CH_3$ | F | $C_6H_5$ | $C_2H_5$ |
| C.926 | $CH_3$ | F | 4-F—$C_6H_5$ | $C_2H_5$ |
| C.927 | $CH_3$ | $OCH_3$ | H | $C_2H_5$ |
| C.928 | $CH_3$ | $OCH_3$ | $CH_3$ | $C_2H_5$ |
| C.929 | $CH_3$ | $OCH_3$ | $C_2H_5$ | $C_2H_5$ |
| C.930 | $CH_3$ | $OCH_3$ | $C_3H_7$ | $C_2H_5$ |
| C.931 | $CH_3$ | $OCH_3$ | $CH(CH_3)_2$ | $C_2H_5$ |
| C.932 | $CH_3$ | $OCH_3$ | cyclopropyl | $C_2H_5$ |
| C.933 | $CH_3$ | $OCH_3$ | $CF_3$ | $C_2H_5$ |
| C.934 | $CH_3$ | $OCH_3$ | $OCH_3$ | $C_2H_5$ |
| C.935 | $CH_3$ | $OCH_3$ | $C_6H_5$ | $C_2H_5$ |
| C.936 | $CH_3$ | $OCH_3$ | 4-F—$C_6H_5$ | $C_2H_5$ |
| C.937 | $CH_3$ | H | H | $CF_3$ |
| C.938 | $CH_3$ | H | $CH_3$ | $CF_3$ |
| C.939 | $CH_3$ | H | $C_2H_5$ | $CF_3$ |
| C.940 | $CH_3$ | H | $C_3H_7$ | $CF_3$ |
| C.941 | $CH_3$ | H | $CH(CH_3)_2$ | $CF_3$ |
| C.942 | $CH_3$ | H | cyclopropyl | $CF_3$ |
| C.943 | $CH_3$ | H | $CF_3$ | $CF_3$ |
| C.944 | $CH_3$ | H | $OCH_3$ | $CF_3$ |
| C.945 | $CH_3$ | H | $C_6H_5$ | $CF_3$ |
| C.946 | $CH_3$ | H | 4-F—$C_6H_5$ | $CF_3$ |
| C.947 | $CH_3$ | $CH_3$ | H | $CF_3$ |
| C.948 | $CH_3$ | $CH_3$ | $CH_3$ | $CF_3$ |
| C.949 | $CH_3$ | $CH_3$ | $C_2H_5$ | $CF_3$ |
| C.950 | $CH_3$ | $CH_3$ | $C_3H_7$ | $CF_3$ |
| C.951 | $CH_3$ | $CH_3$ | $CH(CH_3)_2$ | $CF_3$ |
| C.952 | $CH_3$ | $CH_3$ | cyclopropyl | $CF_3$ |
| C.953 | $CH_3$ | $CH_3$ | $CF_3$ | $CF_3$ |
| C.954 | $CH_3$ | $CH_3$ | $OCH_3$ | $CF_3$ |
| C.955 | $CH_3$ | $CH_3$ | $C_6H_5$ | $CF_3$ |
| C.956 | $CH_3$ | $CH_3$ | 4-F—$C_6H_5$ | $CF_3$ |
| C.957 | $CH_3$ | $C_2H_5$ | H | $CF_3$ |
| C.958 | $CH_3$ | $C_2H_5$ | $CH_3$ | $CF_3$ |
| C.959 | $CH_3$ | $C_2H_5$ | $C_2H_5$ | $CF_3$ |
| C.960 | $CH_3$ | $C_2H_5$ | $C_3H_7$ | $CF_3$ |
| C.961 | $CH_3$ | $C_2H_5$ | $CH(CH_3)_2$ | $CF_3$ |
| C.962 | $CH_3$ | $C_2H_5$ | cyclopropyl | $CF_3$ |
| C.963 | $CH_3$ | $C_2H_5$ | $CF_3$ | $CF_3$ |
| C.964 | $CH_3$ | $C_2H_5$ | $OCH_3$ | $CF_3$ |
| C.965 | $CH_3$ | $C_2H_5$ | $C_6H_5$ | $CF_3$ |
| C.966 | $CH_3$ | $C_2H_5$ | 4-F—$C_6H_5$ | $CF_3$ |
| C.967 | $CH_3$ | cyclopropyl | H | $CF_3$ |
| C.968 | $CH_3$ | cyclopropyl | $CH_3$ | $CF_3$ |
| C.969 | $CH_3$ | cyclopropyl | $C_2H_5$ | $CF_3$ |
| C.970 | $CH_3$ | cyclopropyl | $C_3H_7$ | $CF_3$ |
| C.971 | $CH_3$ | cyclopropyl | $CH(CH_3)_2$ | $CF_3$ |
| C.972 | $CH_3$ | cyclopropyl | cyclopropyl | $CF_3$ |
| C.973 | $CH_3$ | cyclopropyl | $CF_3$ | $CF_3$ |
| C.974 | $CH_3$ | cyclopropyl | $OCH_3$ | $CF_3$ |
| C.975 | $CH_3$ | cyclopropyl | $C_6H_5$ | $CF_3$ |
| C.976 | $CH_3$ | cyclopropyl | 4-F—$C_6H_5$ | $CF_3$ |
| C.977 | $CH_3$ | $CF_3$ | H | $CF_3$ |
| C.978 | $CH_3$ | $CF_3$ | $CH_3$ | $CF_3$ |
| C.979 | $CH_3$ | $CF_3$ | $C_2H_5$ | $CF_3$ |
| C.980 | $CH_3$ | $CF_3$ | $C_3H_7$ | $CF_3$ |
| C.981 | $CH_3$ | $CF_3$ | $CH(CH_3)_2$ | $CF_3$ |
| C.982 | $CH_3$ | $CF_3$ | cyclopropyl | $CF_3$ |
| C.983 | $CH_3$ | $CF_3$ | $CF_3$ | $CF_3$ |
| C.984 | $CH_3$ | $CF_3$ | $OCH_3$ | $CF_3$ |
| C.985 | $CH_3$ | $CF_3$ | $C_6H_5$ | $CF_3$ |
| C.986 | $CH_3$ | $CF_3$ | 4-F—$C_6H_5$ | $CF_3$ |
| C.987 | $CH_3$ | Cl | H | $CF_3$ |
| C.988 | $CH_3$ | Cl | $CH_3$ | $CF_3$ |
| C.989 | $CH_3$ | Cl | $C_2H_5$ | $CF_3$ |
| C.990 | $CH_3$ | Cl | $C_3H_7$ | $CF_3$ |
| C.991 | $CH_3$ | Cl | $CH(CH_3)_2$ | $CF_3$ |
| C.992 | $CH_3$ | Cl | cyclopropyl | $CF_3$ |
| C.993 | $CH_3$ | Cl | $CF_3$ | $CF_3$ |
| C.994 | $CH_3$ | Cl | $OCH_3$ | $CF_3$ |
| C.995 | $CH_3$ | Cl | $C_6H_5$ | $CF_3$ |
| C.996 | $CH_3$ | Cl | 4-F—$C_6H_5$ | $CF_3$ |
| C.997 | $CH_3$ | F | H | $CF_3$ |
| C.998 | $CH_3$ | F | $CH_3$ | $CF_3$ |
| C.999 | $CH_3$ | F | $C_2H_5$ | $CF_3$ |
| C.1000 | $CH_3$ | F | $C_3H_7$ | $CF_3$ |
| C.1001 | $CH_3$ | F | $CH(CH_3)_2$ | $CF_3$ |
| C.1002 | $CH_3$ | F | cyclopropyl | $CF_3$ |
| C.1003 | $CH_3$ | F | $CF_3$ | $CF_3$ |
| C.1004 | $CH_3$ | F | $OCH_3$ | $CF_3$ |
| C.1005 | $CH_3$ | F | $C_6H_5$ | $CF_3$ |
| C.1006 | $CH_3$ | F | 4-F—$C_6H_5$ | $CF_3$ |
| C.1007 | $CH_3$ | $OCH_3$ | H | $CF_3$ |
| C.1008 | $CH_3$ | $OCH_3$ | $CH_3$ | $CF_3$ |
| C.1009 | $CH_3$ | $OCH_3$ | $C_2H_5$ | $CF_3$ |
| C.1010 | $CH_3$ | $OCH_3$ | $C_3H_7$ | $CF_3$ |
| C.1011 | $CH_3$ | $OCH_3$ | $CH(CH_3)_2$ | $CF_3$ |
| C.1012 | $CH_3$ | $OCH_3$ | cyclopropyl | $CF_3$ |
| C.1013 | $CH_3$ | $OCH_3$ | $CF_3$ | $CF_3$ |
| C.1014 | $CH_3$ | $OCH_3$ | $OCH_3$ | $CF_3$ |
| C.1015 | $CH_3$ | $OCH_3$ | $C_6H_5$ | $CF_3$ |
| C.1016 | $CH_3$ | $OCH_3$ | 4-F—$C_6H_5$ | $CF_3$ |
| C.1017 | $CH_3$ | H | H | CN |
| C.1018 | $CH_3$ | H | $CH_3$ | CN |
| C.1019 | $CH_3$ | H | $C_2H_5$ | CN |
| C.1020 | $CH_3$ | H | $C_3H_7$ | CN |
| C.1021 | $CH_3$ | H | $CH(CH_3)_2$ | CN |
| C.1022 | $CH_3$ | H | cyclopropyl | CN |
| C.1023 | $CH_3$ | H | $CF_3$ | CN |
| C.1024 | $CH_3$ | H | $OCH_3$ | CN |
| C.1025 | $CH_3$ | H | $C_6H_5$ | CN |
| C.1026 | $CH_3$ | H | 4-F—$C_6H_5$ | CN |
| C.1027 | $CH_3$ | $CH_3$ | H | CN |
| C.1028 | $CH_3$ | $CH_3$ | $CH_3$ | CN |
| C.1029 | $CH_3$ | $CH_3$ | $C_2H_5$ | CN |
| C.1030 | $CH_3$ | $CH_3$ | $C_3H_7$ | CN |
| C.1031 | $CH_3$ | $CH_3$ | $CH(CH_3)_2$ | CN |
| C.1032 | $CH_3$ | $CH_3$ | cyclopropyl | CN |
| C.1033 | $CH_3$ | $CH_3$ | $CF_3$ | CN |
| C.1034 | $CH_3$ | $CH_3$ | $OCH_3$ | CN |

TABLE C-continued

| No. | R¹ | Rˣ | Rʸ | Rᶻ |
|---|---|---|---|---|
| C.1035 | CH₃ | CH₃ | C₆H₅ | CN |
| C.1036 | CH₃ | CH₃ | 4-F—C₆H₅ | CN |
| C.1037 | CH₃ | C₂H₅ | H | CN |
| C.1038 | CH₃ | C₂H₅ | CH₃ | CN |
| C.1039 | CH₃ | C₂H₅ | C₂H₅ | CN |
| C.1040 | CH₃ | C₂H₅ | C₃H₇ | CN |
| C.1041 | CH₃ | C₂H₅ | CH(CH₃)₂ | CN |
| C.1042 | CH₃ | C₂H₅ | cyclopropyl | CN |
| C.1043 | CH₃ | C₂H₅ | CF₃ | CN |
| C.1044 | CH₃ | C₂H₅ | OCH₃ | CN |
| C.1045 | CH₃ | C₂H₅ | C₆H₅ | CN |
| C.1046 | CH₃ | C₂H₅ | 4-F—C₆H₅ | CN |
| C.1047 | CH₃ | cyclopropyl | H | CN |
| C.1048 | CH₃ | cyclopropyl | CH₃ | CN |
| C.1049 | CH₃ | cyclopropyl | C₂H₅ | CN |
| C.1050 | CH₃ | cyclopropyl | C₃H₇ | CN |
| C.1051 | CH₃ | cyclopropyl | CH(CH₃)₂ | CN |
| C.1052 | CH₃ | cyclopropyl | cyclopropyl | CN |
| C.1053 | CH₃ | cyclopropyl | CF₃ | CN |
| C.1054 | CH₃ | cyclopropyl | OCH₃ | CN |
| C.1055 | CH₃ | cyclopropyl | C₆H₅ | CN |
| C.1056 | CH₃ | cyclopropyl | 4-F—C₆H₅ | CN |
| C.1057 | CH₃ | CF₃ | H | CN |
| C.1058 | CH₃ | CF₃ | CH₃ | CN |
| C.1059 | CH₃ | CF₃ | C₂H₅ | CN |
| C.1060 | CH₃ | CF₃ | C₃H₇ | CN |
| C.1061 | CH₃ | CF₃ | CH(CH₃)₂ | CN |
| C.1062 | CH₃ | CF₃ | cyclopropyl | CN |
| C.1063 | CH₃ | CF₃ | CF₃ | CN |
| C.1064 | CH₃ | CF₃ | OCH₃ | CN |
| C.1065 | CH₃ | CF₃ | C₆H₅ | CN |
| C.1066 | CH₃ | CF₃ | 4-F—C₆H₅ | CN |
| C.1067 | CH₃ | Cl | H | CN |
| C.1068 | CH₃ | Cl | CH₃ | CN |
| C.1069 | CH₃ | Cl | C₂H₅ | CN |
| C.1070 | CH₃ | Cl | C₃H₇ | CN |
| C.1071 | CH₃ | Cl | CH(CH₃)₂ | CN |
| C.1072 | CH₃ | Cl | cyclopropyl | CN |
| C.1073 | CH₃ | Cl | CF₃ | CN |
| C.1074 | CH₃ | Cl | OCH₃ | CN |
| C.1075 | CH₃ | Cl | C₆H₅ | CN |
| C.1076 | CH₃ | Cl | 4-F—C₆H₅ | CN |
| C.1077 | CH₃ | F | H | CN |
| C.1078 | CH₃ | F | CH₃ | CN |
| C.1079 | CH₃ | F | C₂H₅ | CN |
| C.1080 | CH₃ | F | C₃H₇ | CN |
| C.1081 | CH₃ | F | CH(CH₃)₂ | CN |
| C.1082 | CH₃ | F | cyclopropyl | CN |
| C.1083 | CH₃ | F | CF₃ | CN |
| C.1084 | CH₃ | F | OCH₃ | CN |
| C.1085 | CH₃ | F | C₆H₅ | CN |
| C.1086 | CH₃ | F | 4-F—C₆H₅ | CN |
| C.1087 | CH₃ | OCH₃ | H | CN |
| C.1088 | CH₃ | OCH₃ | CH₃ | CN |
| C.1089 | CH₃ | OCH₃ | C₂H₅ | CN |
| C.1090 | CH₃ | OCH₃ | C₃H₇ | CN |
| C.1091 | CH₃ | OCH₃ | CH(CH₃)₂ | CN |
| C.1092 | CH₃ | OCH₃ | cyclopropyl | CN |
| C.1093 | CH₃ | OCH₃ | CF₃ | CN |
| C.1094 | CH₃ | OCH₃ | OCH₃ | CN |
| C.1095 | CH₃ | OCH₃ | C₆H₅ | CN |
| C.1096 | CH₃ | OCH₃ | 4-F—C₆H₅ | CN |
| C.1097 | CH₃ | H | H | Cl |
| C.1098 | CH₃ | H | CH₃ | Cl |
| C.1099 | CH₃ | H | C₂H₅ | Cl |
| C.1100 | CH₃ | H | C₃H₇ | Cl |
| C.1101 | CH₃ | H | CH(CH₃)₂ | Cl |
| C.1102 | CH₃ | H | cyclopropyl | Cl |
| C.1103 | CH₃ | H | CF₃ | Cl |
| C.1104 | CH₃ | H | OCH₃ | Cl |
| C.1105 | CH₃ | H | C₆H₅ | Cl |
| C.1106 | CH₃ | H | 4-F—C₆H₅ | Cl |
| C.1107 | CH₃ | CH₃ | H | Cl |
| C.1108 | CH₃ | CH₃ | CH₃ | Cl |
| C.1109 | CH₃ | CH₃ | C₂H₅ | Cl |
| C.1110 | CH₃ | CH₃ | C₃H₇ | Cl |
| C.1111 | CH₃ | CH₃ | CH(CH₃)₂ | Cl |
| C.1112 | CH₃ | CH₃ | cyclopropyl | Cl |
| C.1113 | CH₃ | CH₃ | CF₃ | Cl |
| C.1114 | CH₃ | CH₃ | OCH₃ | Cl |
| C.1115 | CH₃ | CH₃ | C₆H₅ | Cl |
| C.1116 | CH₃ | CH₃ | 4-F—C₆H₅ | Cl |
| C.1117 | CH₃ | C₂H₅ | H | Cl |
| C.1118 | CH₃ | C₂H₅ | CH₃ | Cl |
| C.1119 | CH₃ | C₂H₅ | C₂H₅ | Cl |
| C.2239 | CH₃ | C₂H₅ | C₃H₇ | Cl |
| C.2240 | CH₃ | C₂H₅ | CH(CH₃)₂ | Cl |
| C.2241 | CH₃ | C₂H₅ | cyclopropyl | Cl |
| C.2242 | CH₃ | C₂H₅ | CF₃ | Cl |
| C.2243 | CH₃ | C₂H₅ | OCH₃ | Cl |
| C.2244 | CH₃ | C₂H₅ | C₆H₅ | Cl |
| C.2245 | CH₃ | C₂H₅ | 4-F—C₆H₅ | Cl |
| C.2246 | CH₃ | cyclopropyl | H | Cl |
| C.2247 | CH₃ | cyclopropyl | CH₃ | Cl |
| C.2248 | CH₃ | cyclopropyl | C₂H₅ | Cl |
| C.2249 | CH₃ | cyclopropyl | C₃H₇ | Cl |
| C.2250 | CH₃ | cyclopropyl | CH(CH₃)₂ | Cl |
| C.2251 | CH₃ | cyclopropyl | cyclopropyl | Cl |
| C.2252 | CH₃ | cyclopropyl | CF₃ | Cl |
| C.2253 | CH₃ | cyclopropyl | OCH₃ | Cl |
| C.2254 | CH₃ | cyclopropyl | C₆H₅ | Cl |
| C.2255 | CH₃ | cyclopropyl | 4-F—C₆H₅ | Cl |
| C.2256 | CH₃ | CF₃ | H | Cl |
| C.2257 | CH₃ | CF₃ | CH₃ | Cl |
| C.2258 | CH₃ | CF₃ | C₂H₅ | Cl |
| C.2259 | CH₃ | CF₃ | C₃H₇ | Cl |
| C.2260 | CH₃ | CF₃ | CH(CH₃)₂ | Cl |
| C.2261 | CH₃ | CF₃ | cyclopropyl | Cl |
| C.2262 | CH₃ | CF₃ | CF₃ | Cl |
| C.2263 | CH₃ | CF₃ | OCH₃ | Cl |
| C.2264 | CH₃ | CF₃ | C₆H₅ | Cl |
| C.2265 | CH₃ | CF₃ | 4-F—C₆H₅ | Cl |
| C.2266 | CH₃ | Cl | H | Cl |
| C.2267 | CH₃ | Cl | CH₃ | Cl |
| C.2268 | CH₃ | Cl | C₂H₅ | Cl |
| C.2269 | CH₃ | Cl | C₃H₇ | Cl |
| C.2270 | CH₃ | Cl | CH(CH₃)₂ | Cl |
| C.2271 | CH₃ | Cl | cyclopropyl | Cl |
| C.2272 | CH₃ | Cl | CF₃ | Cl |
| C.2273 | CH₃ | Cl | OCH₃ | Cl |
| C.2274 | CH₃ | Cl | C₆H₅ | Cl |
| C.2275 | CH₃ | Cl | 4-F—C₆H₅ | Cl |
| C.2276 | CH₃ | F | H | Cl |
| C.2277 | CH₃ | F | CH₃ | Cl |
| C.2278 | CH₃ | F | C₂H₅ | Cl |
| C.2279 | CH₃ | F | C₃H₇ | Cl |
| C.2280 | CH₃ | F | CH(CH₃)₂ | Cl |
| C.2281 | CH₃ | F | cyclopropyl | Cl |
| C.2282 | CH₃ | F | CF₃ | Cl |
| C.2283 | CH₃ | F | OCH₃ | Cl |
| C.2284 | CH₃ | F | C₆H₅ | Cl |
| C.2285 | CH₃ | F | 4-F—C₆H₅ | Cl |
| C.2286 | CH₃ | OCH₃ | H | Cl |
| C.2287 | CH₃ | OCH₃ | CH₃ | Cl |
| C.2288 | CH₃ | OCH₃ | C₂H₅ | Cl |
| C.2289 | CH₃ | OCH₃ | C₃H₇ | Cl |
| C.2290 | CH₃ | OCH₃ | CH(CH₃)₂ | Cl |
| C.2291 | CH₃ | OCH₃ | cyclopropyl | Cl |
| C.2292 | CH₃ | OCH₃ | CF₃ | Cl |
| C.2293 | CH₃ | OCH₃ | OCH₃ | Cl |
| C.2294 | CH₃ | CCH₃ | C₆H₅ | Cl |
| C.2295 | CH₃ | OCH₃ | 4-F—C₆H₅ | Cl |
| C.2296 | CH₃ | CH₃ | CH₂CH₂ | |
| C.2297 | CH₃ | CF₃ | CH₂CH₂ | |
| C.2298 | CF₃ | CH₃ | CH₂CH₂ | |
| C.2299 | CH₃ | C₂H₅ | CH₂CH₂ | |
| C.2300 | C₂H₅ | CH₃ | CH₂CH₂ | |
| C.2301 | Cl | CH₃ | CH₂CH₂ | |
| C.2302 | CH₃ | Cl | CH₂CH₂ | |
| C.2303 | CH₃ | CH₃ | CH₂CH₂CH₂ | |
| C.2304 | CH₃ | CF₃ | CH₂CH₂CH₂ | |
| C.2305 | CF₃ | CH₃ | CH₂CH₂CH₂ | |
| C.2306 | CH₃ | C₂H₅ | CH₂CH₂CH₂ | |
| C.2307 | C₂H₅ | CH₃ | CH₂CH₂CH₂ | |

TABLE C-continued

| No. | R¹ | Rˣ | Rʸ | Rᶻ |
|---|---|---|---|---|
| C.2308 | Cl | CH₃ | CH₂CH₂CH₂ | |
| C.2309 | CH₃ | Cl | CH₂CH₂CH₂ | |
| C.2310 | CH₃ | CH₃ | CH₂CH₂CH₂CH₂ | |
| C.2311 | CH₃ | CF₃ | CH₂CH₂CH₂CH₂ | |
| C.2312 | CF₃ | CH₃ | CH₂CH₂CH₂CH₂ | |
| C.2313 | CH₃ | C₂H₅ | CH₂CH₂CH₂CH₂ | |
| C.2314 | C₂H₅ | CH₃ | CH₂CH₂CH₂CH₂ | |
| C.2315 | Cl | CH₃ | CH₂CH₂CH₂CH₂ | |
| C.2316 | CH₃ | Cl | CH₂CH₂CH₂CH₂ | |
| C.2317 | CH₂CH₃ | CH₃ | H | H |
| C.2318 | CH₂CH₃ | CH₃ | CH₃ | H |
| C.2319 | CH₂CH₃ | CH₃ | C₂H₅ | H |
| C.2320 | CH₂CH₃ | CH₃ | C₃H₇ | H |
| C.2321 | CH₂CH₃ | CH₃ | C₄H₉ | H |
| C.2322 | CH₂CH₃ | CH₃ | CH(CH₃)₂ | H |
| C.2323 | CH₂CH₃ | CH₃ | cyclopropyl | H |
| C.2324 | CH₂CH₃ | CH₃ | CF₃ | H |
| C.2325 | CH₂CH₃ | CH₃ | OCH₃ | H |
| C.2326 | CH₂CH₃ | CH₃ | OC₂H₅ | H |
| C.2327 | CH₂CH₃ | CH₃ | CH₂—C₆H₅ | H |
| C.2328 | CH₂CH₃ | CH₃ | CH(CH₃)C₆H₅ | H |
| C.2329 | CH₂CH₃ | CH₃ | C₆H₅ | H |
| C.2330 | CH₂CH₃ | CH₃ | 4-F—C₆H₅ | H |
| C.2331 | CH₂CH₃ | CH₃ | 4-Cl-2-pyridyl | H |
| C.2332 | CH₂CH₃ | CH₃ | F | H |
| C.2333 | CH₂CH₃ | CH₃ | CN | H |
| C.2334 | CH₂CH₃ | C₂H₅ | H | H |
| C.2335 | CH₂CH₃ | C₂H₅ | CH₃ | H |
| C.2336 | CH₂CH₃ | C₂H₅ | C₂H₅ | H |
| C.2337 | CH₂CH₃ | C₂H₅ | C₃H₇ | H |
| C.2338 | CH₂CH₃ | C₂H₅ | C₄H₉ | H |
| C.2339 | CH₂CH₃ | C₂H₅ | CH(CH₃)₂ | H |
| C.2340 | CH₂CH₃ | C₂H₅ | cyclopropyl | H |
| C.2341 | CH₂CH₃ | C₂H₅ | CF₃ | H |
| C.2342 | CH₂CH₃ | C₂H₅ | OCH₃ | H |
| C.2343 | CH₂CH₃ | C₂H₅ | OC₂H₅ | H |
| C.2344 | CH₂CH₃ | C₂H₅ | CH₂—C₆H₅ | H |
| C.2345 | CH₂CH₃ | C₂H₅ | CH(CH₃)C₆H₅ | H |
| C.2346 | CH₂CH₃ | C₂H₅ | C₆H₅ | H |
| C.2347 | CH₂CH₃ | C₂H₅ | 4-F—C₆H₅ | H |
| C.2348 | CH₂CH₃ | C₂H₅ | 4-Cl-2-pyridyl | H |
| C.2349 | CH₂CH₃ | C₂H₅ | F | H |
| C.2350 | CH₂CH₃ | C₂H₅ | CN | H |
| C.2351 | CH₂CH₃ | CF₃ | H | H |
| C.2352 | CH₂CH₃ | CF₃ | CH₃ | H |
| C.2353 | CH₂CH₃ | CF₃ | C₂H₅ | H |
| C.2354 | CH₂CH₃ | CF₃ | C₃H₇ | H |
| C.2355 | CH₂CH₃ | CF₃ | C₄H₉ | H |
| C.2356 | CH₂CH₃ | CF₃ | CH(CH₃)₂ | H |
| C.2357 | CH₂CH₃ | CF₃ | cyclopropyl | H |
| C.2358 | CH₂CH₃ | CF₃ | CF₃ | H |
| C.2359 | CH₂CH₃ | CF₃ | OCH₃ | H |
| C.2360 | CH₂CH₃ | CF₃ | OC₂H₅ | H |
| C.2361 | CH₂CH₃ | CF₃ | CH₂—C₆H₅ | H |
| C.2362 | CH₂CH₃ | CF₃ | CH(CH₃)C₆H₅ | H |
| C.2363 | CH₂CH₃ | CF₃ | C₆H₅ | H |
| C.2364 | CH₂CH₃ | CF₃ | 4-F—C₆H₅ | H |
| C.2365 | CH₂CH₃ | CF₃ | 4-Cl-2-pyridyl | H |
| C.2366 | CH₂CH₃ | CF₃ | F | H |
| C.2367 | CH₂CH₃ | CF₃ | CN | H |
| C.2368 | CH₂CH₃ | Cl | H | H |
| C.2369 | CH₂CH₃ | Cl | CH₃ | H |
| C.2370 | CH₂CH₃ | Cl | C₂H₅ | H |
| C.2371 | CH₂CH₃ | Cl | C₃H₇ | H |
| C.2372 | CH₂CH₃ | Cl | C₄H₉ | H |
| C.2373 | CH₂CH₃ | Cl | CH(CH₃)₂ | H |
| C.2374 | CH₂CH₃ | Cl | cyclopropyl | H |
| C.2375 | CH₂CH₃ | Cl | CF₃ | H |
| C.2376 | CH₂CH₃ | Cl | OCH₃ | H |
| C.2377 | CH₂CH₃ | Cl | OC₂H₅ | H |
| C.2378 | CH₂CH₃ | Cl | CH₂—C₆H₅ | H |
| C.2379 | CH₂CH₃ | Cl | CH(CH₃)C₆H₅ | H |
| C.2380 | CH₂CH₃ | Cl | C₆H₅ | H |
| C.2381 | CH₂CH₃ | Cl | 4-F—C₆H₅ | H |
| C.2382 | CH₂CH₃ | Cl | 4-Cl-2-pyridyl | H |
| C.2383 | CH₂CH₃ | Cl | F | H |
| C.2384 | CH₂CH₃ | Cl | CN | H |
| C.2385 | CH₂CH₃ | OCH₃ | H | H |
| C.2386 | CH₂CH₃ | OCH₃ | CH₃ | H |
| C.2387 | CH₂CH₃ | OCH₃ | C₂H₅ | H |
| C.2388 | CH₂CH₃ | OCH₃ | C₃H₇ | H |
| C.2389 | CH₂CH₃ | OCH₃ | C₄H₉ | H |
| C.2390 | CH₂CH₃ | OCH₃ | CH(CH₃)₂ | H |
| C.2391 | CH₂CH₃ | OCH₃ | cyclopropyl | H |
| C.2392 | CH₂CH₃ | OCH₃ | CF₃ | H |
| C.2393 | CH₂CH₃ | OCH₃ | OCH₃ | H |
| C.2394 | CH₂CH₃ | OCH₃ | OC₂H₅ | H |
| C.2395 | CH₂CH₃ | OCH₃ | CH₂—C₆H₅ | H |
| C.2396 | CH₂CH₃ | OCH₃ | CH(CH₃)C₆H₅ | H |
| C.2397 | CH₂CH₃ | OCH₃ | C₆H₅ | H |
| C.2398 | CH₂CH₃ | OCH₃ | 4-F—C₆H₅ | H |
| C.2399 | CH₂CH₃ | OCH₃ | 4-Cl-2-pyridyl | H |
| C.2400 | CH₂CH₃ | OCH₃ | F | H |
| C.2401 | CH₂CH₃ | OCH₃ | CN | H |
| C.2402 | CH₂CH₃ | CH₃ | H | CH₃ |
| C.2403 | CH₂CH₃ | CH₃ | CH₃ | CH₃ |
| C.2404 | CH₂CH₃ | CH₃ | C₂H₅ | CH₃ |
| C.2405 | CH₂CH₃ | CH₃ | C₃H₇ | CH₃ |
| C.2406 | CH₂CH₃ | CH₃ | C₄H₉ | CH₃ |
| C.2407 | CH₂CH₃ | CH₃ | CH(CH₃)₂ | CH₃ |
| C.2408 | CH₂CH₃ | CH₃ | cyclopropyl | CH₃ |
| C.2409 | CH₂CH₃ | CH₃ | CF₃ | CH₃ |
| C.2410 | CH₂CH₃ | CH₃ | OCH₃ | CH₃ |
| C.2411 | CH₂CH₃ | CH₃ | OC₂H₅ | CH₃ |
| C.2412 | CH₂CH₃ | CH₃ | CH₂—C₆H₅ | CH₃ |
| C.2413 | CH₂CH₃ | CH₃ | CH(CH₃)C₆H₅ | CH₃ |
| C.2414 | CH₂CH₃ | CH₃ | C₆H₅ | CH₃ |
| C.2415 | CH₂CH₃ | CH₃ | 4-F—C₆H₅ | CH₃ |
| C.2416 | CH₂CH₃ | CH₃ | 4-Cl-2-pyridyl | CH₃ |
| C.2417 | CH₂CH₃ | CH₃ | F | CH₃ |
| C.2418 | CH₂CH₃ | CH₃ | CN | CH₃ |
| C.2419 | CH₂CH₃ | C₂H₅ | H | CH₃ |
| C.2420 | CH₂CH₃ | C₂H₅ | CH₃ | CH₃ |
| C.2421 | CH₂CH₃ | C₂H₅ | C₂H₅ | CH₃ |
| C.2422 | CH₂CH₃ | C₂H₅ | C₃H₇ | CH₃ |
| C.2423 | CH₂CH₃ | C₂H₅ | C₄H₉ | CH₃ |
| C.2424 | CH₂CH₃ | C₂H₅ | CH(CH₃)₂ | CH₃ |
| C.2425 | CH₂CH₃ | C₂H₅ | cyclopropyl | CH₃ |
| C.2426 | CH₂CH₃ | C₂H₅ | CF₃ | CH₃ |
| C.2427 | CH₂CH₃ | C₂H₅ | OCH₃ | CH₃ |
| C.2428 | CH₂CH₃ | C₂H₅ | OC₂H₅ | CH₃ |
| C.2429 | CH₂CH₃ | C₂H₅ | CH₂—C₆H₅ | CH₃ |
| C.2430 | CH₂CH₃ | C₂H₅ | CH(CH₃)C₆H₅ | CH₃ |
| C.2431 | CH₂CH₃ | C₂H₅ | C₆H₅ | CH₃ |
| C.2432 | CH₂CH₃ | C₂H₅ | 4-F-C₆H₅ | CH₃ |
| C.2433 | CH₂CH₃ | C₂H₅ | 4-Cl-2-pyridyl | CH₃ |
| C.2434 | CH₂CH₃ | C₂H₅ | F | CH₃ |
| C.2435 | CH₂CH₃ | C₂H₅ | CN | CH₃ |
| C.2436 | CH₂CH₃ | CF₃ | H | CH₃ |
| C.2437 | CH₂CH₃ | CF₃ | CH₃ | CH₃ |
| C.2438 | CH₂CH₃ | CF₃ | C₂H₅ | CH₃ |
| C.2439 | CH₂CH₃ | CF₃ | C₃H₇ | CH₃ |
| C.2440 | CH₂CH₃ | CF₃ | C₄H₉ | CH₃ |
| C.2441 | CH₂CH₃ | CF₃ | CH(CH₃)₂ | CH₃ |
| C.2442 | CH₂CH₃ | CF₃ | cyclopropyl | CH₃ |
| C.2443 | CH₂CH₃ | CF₃ | CF₃ | CH₃ |
| C.2444 | CH₂CH₃ | CF₃ | OCH₃ | CH₃ |
| C.2445 | CH₂CH₃ | CF₃ | OC₂H₅ | CH₃ |
| C.2446 | CH₂CH₃ | CF₃ | CH₂—C₆H₅ | CH₃ |
| C.2447 | CH₂CH₃ | CF₃ | CH(CH₃)C₆H₅ | CH₃ |
| C.2448 | CH₂CH₃ | CF₃ | C₆H₅ | CH₃ |
| C.2449 | CH₂CH₃ | CF₃ | 4-F—C₆H₅ | CH₃ |
| C.2450 | CH₂CH₃ | CF₃ | 4-Cl-2-pyridyl | CH₃ |
| C.2451 | CH₂CH₃ | CF₃ | F | CH₃ |
| C.2452 | CH₂CH₃ | CF₃ | CN | CH₃ |
| C.2453 | CH₂CH₃ | Cl | H | CH₃ |
| C.2454 | CH₂CH₃ | Cl | CH₃ | CH₃ |
| C.2455 | CH₂CH₃ | Cl | C₂H₅ | CH₃ |
| C.2456 | CH₂CH₃ | Cl | C₃H₇ | CH₃ |
| C.2457 | CH₂CH₃ | Cl | C₄H₉ | CH₃ |
| C.2458 | CH₂CH₃ | Cl | CH(CH₃)₂ | CH₃ |
| C.2459 | CH₂CH₃ | Cl | cyclopropyl | CH₃ |
| C.2460 | CH₂CH₃ | Cl | CF₃ | CH₃ |
| C.2461 | CH₂CH₃ | Cl | OCH₃ | CH₃ |

TABLE C-continued

| No. | R¹ | Rˣ | Rʸ | Rᶻ |
|---|---|---|---|---|
| C.2462 | CH₂CH₃ | Cl | OC₂H₅ | CH₃ |
| C.2463 | CH₂CH₃ | Cl | CH₂—C₆H₅ | CH₃ |
| C.2464 | CH₂CH₃ | Cl | CH(CH₃)C₆H₅ | CH₃ |
| C.2465 | CH₂CH₃ | Cl | C₆H₅ | CH₃ |
| C.2466 | CH₂CH₃ | Cl | 4-F—C₆H₅ | CH₃ |
| C.2467 | CH₂CH₃ | Cl | 4-Cl-2-pyridyl | CH₃ |
| C.2468 | CH₂CH₃ | Cl | F | CH₃ |
| C.2469 | CH₂CH₃ | Cl | CN | CH₃ |
| C.2470 | CH₂CH₃ | OCH₃ | H | CH₃ |
| C.2471 | CH₂CH₃ | OCH₃ | CH₃ | CH₃ |
| C.2472 | CH₂CH₃ | OCH₃ | C₂H₅ | CH₃ |
| C.2473 | CH₂CH₃ | OCH₃ | C₃H₇ | CH₃ |
| C.2474 | CH₂CH₃ | OCH₃ | C₄H₉ | CH₃ |
| C.2475 | CH₂CH₃ | OCH₃ | CH(CH₃)₂ | CH₃ |
| C.2476 | CH₂CH₃ | OCH₃ | cyclopropyl | CH₃ |
| C.2477 | CH₂CH₃ | OCH₃ | CF₃ | CH₃ |
| C.2478 | CH₂CH₃ | OCH₃ | OCH₃ | CH₃ |
| C.2479 | CH₂CH₃ | OCH₃ | OC₂H₅ | CH₃ |
| C.2480 | CH₂CH₃ | OCH₃ | CH₂—C₆H₅ | CH₃ |
| C.2481 | CH₂CH₃ | OCH₃ | CH(CH₃)C₆H₅ | CH₃ |
| C.2482 | CH₂CH₃ | OCH₃ | C₆H₅ | CH₃ |
| C.2483 | CH₂CH₃ | OCH₃ | 4-F—C₆H₅ | CH₃ |
| C.2484 | CH₂CH₃ | OCH₃ | 4-Cl-2-pyridyl | CH₃ |
| C.2485 | CH₂CH₃ | OCH₃ | F | CH₃ |
| C.2486 | CH₂CH₃ | OCH₃ | CN | CH₃ |

The compounds I are suitable as fungicides.

The compounds I are distinguished by outstanding efficacy against a broad spectrum of phytopathogenic fungi, in particular from the classes of the Ascomycetes, Deuteromycetes, Phycomycetes and Basidiomycetes. Some of them act systemically and can be employed as foliar- and soil-acting fungicides.

They are especially important for controlling a large number of fungi on a variety of crop plants such as wheat, rye, barley, oats, rice, maize, grass, bananas, cotton, soybeans, coffee, sugar cane, grapevines, fruit species, ornamentals and vegetables such as cucumbers, beans, tomatoes, potatoes and cucurbits, and on the seeds of these plants.

Specifically, they are suitable for controlling the following plant diseases: *Erysiphe graminis* (powdery mildew) in cereals, *Erysiphe cichoracearum* and *Sphaerotheca fuliginea* on cucurbits, *Podosphaera leucotricha* on apples, *Uncinula necator* on grapevines, Puccinia species on cereals, Rhizoctonia species on cotton, rice and lawns, Ustilago species on cereals and sugar cane, *Venturia inaequalis* (scab) on apples, Helminthosporium species on cereals, *Septoria nodorum* on wheat, *Botrytis cinerea* (gray mold) on strawberries, vegetables, ornamentals and grapevines, *Cercospora arachidicola* on peanuts, *Pseudocercosporella herpotrichoides* on wheat, barley, *Pyricularia oryzae* on rice, *Phytophthora infestans* on potatoes and tomatoes, Fusarium and Verticillium species on a variety of plants, *Plasmopara viticola* on grapevines, Pseudocercosporella species in hops and cucumbers, Alternaria species on vegetables and fruit and Mycosphaerella species in bananas.

Moreover, the compounds I are suitable for controlling harmful fungi in the protection of materials (eg. wood, paper, paint dispersions, fibers or tissues) and in the protection of stored products.

The compounds I are applied by treating the fungi, or the plants, seeds, materials or the soil to be protected against fungal infection, with a fungicidally active amount of the active ingredients. Application is effected before or after infection of the materials, plants or seeds by the fungi.

They can be converted into the customary formulations, such as solutions, emulsions, suspensions, dusts, powders, pastes and granules. The use form depends on the specific intended use; in any case, it should guarantee fine and uniform distribution of the compound according to the invention. The formulations are prepared in a known manner, eg. by extending the active ingredient with solvents and/or carriers, if desired using emulsifiers and dispersants, it also being possible to use other organic solvents as auxiliary solvents if water is used as the diluent. Suitable auxiliaries are essentially: solvents such as aromatics (eg. xylene), chlorinated aromatics (eg. chlorobenzenes), paraffins (eg. mineral oil fractions), alcohols (eg. methanol, butanol), ketones (eg. cyclohexanone), amines (eg. ethanolamine, dimethylformamide) and water; carriers such as ground natural minerals (eg. kaolins, clays, talc, chalk) and ground synthetic minerals (eg. highly disperse silica, silicates); emulsifiers such as nonionic and anionic emulsifiers (eg. polyoxyethylene fatty alcohol ethers, alkylsulfonates and arylsulfonates), and dispersants such as ligninsulfite waste liquors and methylcellulose.

The fungicidal compositions generally comprise from 0.1 to 95, preferably from 0.5 to 90, % by weight of active ingredient.

Depending on the nature of the desired effect, the rates of application in crop protection are from 0.01 to 2.0 kg of active ingredient per ha.

In the treatment of seed, amounts of active ingredient of from 0.001 to 0.1 g, preferably 0.01 to 0.05 g, are generally required per kilogram of seed.

When used in the protection of materials or stored products, the rate of application of active ingredient depends on the nature of the field of application and on the desired effect. Normal rates of application in the protection of materials are, for example, 0.001 g to 2 kg, preferably 0.005 g to 1 kg, of active ingredient per cubic meter of material treated.

In the use form as fungicides, the compositions according to the invention can also exist together with other active ingredients, eg. with herbicides, insecticides, growth regulators, fungicides, or else with fertilizers.

A mixture with fungicides frequently results in a widened fungicidal spectrum of action.

The following list of fungicides together with which the compounds according to the invention can be used is intended to illustrate the possible combinations, but not to impose any limitation:

sulfur, dithiocarbamates and their derivatives, such as iron (III) dimethyldithiocarbamate, zinc dimethyldithiocarbamate, zinc ethylenebisdithiocarbamate, manganese ethylenebisdithiocarbamate, manganese zinc ethylenediaminebisdithiocarbamate, tetramethylthiuram disulfide, ammonia complex of zinc (N,N-ethylenebisdithiocarbamate), ammonia complex of zinc (N,N'-propylenebisdithiocarbamate), zinc (N,N'-propylenebisdithiocarbamate), N,N'-polypropylenebis (thiocarbamoyl) disulfide;

nitro derivatives, such as dinitro(1-methylheptyl)phenyl crotonate, 2-sec-butyl-4,6-dinitrophenyl 3,3-dimethyl acrylate, 2-sec-butyl-4,6-dinitrophenylisopropyl carbonate, diisopropyl 5-nitro-isophthalate;

heterocyclic substances, such as 2-heptadecyl-2-imidazoline acetate, 2,4-dichloro-6-(o-chloroanilino)-2-triazine, O,O-di-ethyl phthalimidophosphonothioate, 5-amino-1-[bis(dimethylamino)phosphinyl]-3-phenyl-1,2,4-triazole, 2,3-dicyano-1,4-dithioanthraquinone, 2-thio-1,3-dithiolo[4,5-b]quinoxaline, methyl 1-(butylcarbamoyl)-2-benzimidazolecarbamate, 2-methoxycarbonyl-aminobenzimidazole, 2-(2-furyl) benzimidazole, 2-(4-thiazolyl)-benzimidazole, N-(1,1,2,2-tetrachloroethylthio)-tetrahydrophthalimide, N-trichloromethylthiotetrahydrophthalimide, N-trichloromethylthiophthalimide, N-dichlorofluoromethylthio-N',N'-dimethyl-N-phenylsulfodiamide, 5-ethoxy-3-trichloromethyl-1,2,3-thiadiazole, 2-thiocyanatomethylthiobenzothiazole, 1,4-dichloro-2,5-dimethoxybenzene, 4-(2-chlorophenylhydrazono)-3-methyl-5-isoxazolone, pyridine-2-thiol oxide, 8-hydroxyquinoline or its copper salt, 2,3-dihydro-5-carboxanilido-6-methyl-1,4-oxathiine, 2,3-di-hydro-5-carboxanilido-6-methyl-1,4-oxathiine 4,4-dioxide, 2-methyl-5,6-dihydro-4H-pyran-3-carboxanilide, 2-methylfuran-3-carboxanilide, 2,5-dimethylfuran-3-carboxanilide, 2,4,5-trimethylfuran-3-carboxanilide, N-cyclohexyl-2,5-dimethylfuran-3-carboxamide, N-cyclohexyl-N-methoxy-2,5-dimethylfuran-3-carboxamide, 2-methylbenzanilide, 2-iodobenzanilide, N-formyl-N-morpholine-2,2,2-trichloroethyl acetal, piperazine-1,4-diylbis(2,2,2-trichloroethyl)formamide, 1-(3,4-dichloroanilino)-1-formylamino-2,2,2-trichloroethane, 2,6-dimethyl-N-tridecylmorpholine or its salts, 2,6-dimethyl-N-cyclododecylmorpholine or its salts, N-[3-(p-tert-butylphenyl)-2-methylpropyl]-cis-2,6-dimethylmorpholine, N-[3-(p-tert-butylphenyl)-2-methylpropyl]piperidine, 1-[2-(2,4-dichlorophenyl)-4-ethyl-1,3-dioxolan-2-ylethyl]-1H-1,2,4-triazole, 1-[2-(2,4-dichlorophenyl)-4-n-propyl-1,3-dioxolan-2-ylethyl]-1H-1,2,4-triazole, N-(n-propyl)-N-(2,4,6-trichlorophenoxy-ethyl)-N'-imidazolylurea, 1-(4-chlorophenoxy)-3,3-dimethyl-1-(1H-1,2,4-triazol-1-yl)-2-butanone, 1-(4-chlorophenoxy)-3,3-dimethyl-1-(1H-1,2,4-triazol-1-yl)-2-butanol, (2RS,3RS)-1-[3-(2-chlorophenyl)-2-(4-fluorophenyl)oxiran-2-ylmethyl]-1H-1,2,4-triazole, α-(2-chlorophenyl)-α-(4-chlorophenyl)-5-pyrimidinemethanol, 5-butyl-2-dimethylamino-4-hydroxy-6-methylpyrimidine, bis(p-chlorophenyl)-3-pyridinemethanol, 1,2-bis(3-ethoxycarbonyl-2-thioureido)benzene, 1,2-bis(3-methoxycarbonyl-2-thioureido)benzene, strobilurins such as methyl E-methoxyimino-[α-(o-tolyloxy)-o-tolyl]acetate, methyl E-2-{2-[6-[(2-cyanophenoxy)pyrimidin-4-yloxy]phenyl}-3-methoxyacrylate, N-methyl-E-methoxyimino-[α-(2-phenoxyphenyl]acetamide, N-methyl-E-methoxyimino-[α-(2,5-dimethylphenoxy)-o-tolyl] acetamide, anilinopyrimidines such as N-(4,6-dimethylpyrimidin-2-yl)-aniline, N-[4-methyl-6-(1-propynyl)pyrimidin-2-yl]aniline, N-[4-methyl-6-cyclopropylpyrimidin-2-yl]aniline, phenylpyrroles such as 4-(2,2-difluoro-1,3-benzodioxol-4-yl)-pyrrole-3-carbonitrile, cinnamamides such as 3-(4-chlorophenyl)-3-(3,4-dimethoxyphenyl)acryloylmorpholine, and a variety of fungicides such as dodecylguanidine acetate, 3-[3-(3,5-dimethyl-2-oxycyclohexyl)-2-hydroxyethyl]-glutarimide, hexachlorobenzene, methyl-N-(2,6-dimethylphenyl)-N-(2-furoyl)-DL-alaninate, DL-N-(2,6-dimethylphenyl)-N-(2'-methoxyacetyl)-alanine methyl ester, N-(2,6-dimethylphenyl)-N-chloroacetyl-D,L-2-aminobutyrolactone, DL-N-(2,6-dimethylphenyl)-N-(phenylacetyl)-alanine methyl ester, 5-methyl-5-vinyl-3-(3,5-dichlorophenyl)-2,4-dioxo-1,3-oxazolidine, 3-[3,5-dichlorophenyl-(5-methyl-5-methoxymethyl]-1,3-oxazolidine-2,4-dione, 3-(3,5-dichlorophenyl)-1-isopropylcarbamoylhydantoin, N-(3,5-dichlorophenyl)-1,2-dimethylcyclopropane-1,2-dicarboximide, 2-cyano-[N-(ethylaminocarbonyl)-2-methoximino]-acetamide, 1-[2-(2,4-dichlorophenyl)-pentyl]-1H-1,2,4-triazole, 2,4-difluoro-a-(1H-1,2,4-triazolyl-1-methyl)-benzhydryl alcohol, N-(3-chloro-2,6-dinitro-4-trifluoromethylphenyl)-5-trifluoromethyl-3-chloro-2-aminopyridine, 1-((bis-(4-fluorophenyl)methylsilyl)methyl)-1H-1,2,4-triazole.

The compounds of the formula I are furthermore suitable for effectively controlling pests from the classes of the insects, arachnids and nematodes. They can be employed as pesticides in crop protection and in the hygiene, stored-product and veterinary sector.

The harmful insects include, from the order of the lepidopterans (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusiani, Zeiraphera canadensis.*

From the order of the beetles (Coleoptera), for example, *Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Otiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus, Sitophilus granaria.*

From the order of the dipterans (Diptera), for example, *Aedes aegypti, Aedes vexans, Anastrepha ludens, Anopheles*

*maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossina morsitans, Haematobia irritans, Haplodiplosis equestris, Hylemyia platura, Hypoderma lineata, Liriomyza sativae, Liriomyza trifolii, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea, Tipula paludosa.*

From the order of the thrips (Thysanoptera), for example, *Frankliniella fusca, Frankliniella occidentalis, Frankliniella tritici, Scirtothrips citri, Thrips oryzae, Thrips palmi, Thrips tabaci.*

From the order of the hymenopterans (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta.*

From the order of the heteropterans (Heteroptera), for example, *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor.*

From the order of the homopterans (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dysaphis radicola, Dysaulacorthum pseudosolani, Empoasca fabae, Macrosiphum avenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii.*

From the order of the termites (Isoptera), for example, *Calotermes flavicollis, Leucotermes flavipes, Reticulitermes lucifugus, Termes natalensis.*

From the order of the orthopterans (Orthoptera), for example, *Acheta domestica, Blatta orientalis, Blattella germanica, Forficula auricularia, Gryllotalpa gryllotalpa, Locusta migratoria, Melanoplus bivittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

From the class of the Arachnoidea, for example, arachnids (Acarina) such as *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobius megnini, Paratetranychus pilosus, Dermanyssus gallinae, Phyllocoptruta oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius, Tetranychus urticae.*

From the class of the nematodes, for example, root knot nematodes, eg. *Meloidogyne hapla, Meloidogyne incognita, Meloidogyne javanica*, cyst-forming nematodes, eg. *Globodera rostochiensis, Heterodera avenae, Heterodera glycines, Heterodera schachtii, Heterodera trifolii*, stem eelworms and foliar nematodes, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The active ingredients can be used as such, in the form of their formulations or the use forms prepared therefrom, for example in the form of ready-to-spray solutions, powders, suspensions or dispersions, emulsions, oil dispersions, pastes, dusts, materials for spreading or granules, by means of spraying, atomizing, dusting, spreading or pouring. The use forms depend entirely on the intended purposes; in any case, they should guarantee the finest possible distribution of the active ingredients according to the invention.

The concentrations of active ingredient in the ready-to-use preparations can be varied within substantial ranges.

In general, they are from 0.0001 to 10%, preferably from 0.01 to 1%.

The active ingredients can also be used successfully in the ultra-low-volume method (ULV), it being possible to apply formulations with over 95% by weight of active ingredient, or even the active ingredient without additives.

Under field conditions, the rate of application of active ingredient for controlling pests is 0.1 to 2.0, preferably 0.2 to 1.0, kg/ha.

Substances which are suitable for the preparation of ready-to-spray solutions, emulsions, pastes or oil dispersions are mineral oil fractions of medium to high boiling point such as kerosene or diesel oil, furthermore coal tar oil and oils of vegetable or animal origin, aliphatic, cyclic and aromatic hydrocarbons, eg. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, eg. dimethylformamide, dimethyl sulfoxide, N-methylpyrrolidone and water.

Aqueous use forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of wetting agent, tackifier, dispersant or emulsifier. However, it is also possible to prepare concentrates composed of active ingredient, wetting agent, tackifier, dispersant or emulsifier and, if desired, solvent or oil, which are suitable for dilution with water.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of naphthalenesulfonic acid with phenol and formaldehyde, polyoxyethylene octylphenyl ether, ethoxylated isooctylphenol, octylphenol, nonylphenol, alkylphenyl polyglycol ethers, tributylphenyl polyglycol ether, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, ligninsulfite waste liquors and methylcellulose.

Powders, materials for spreading and dusts can be prepared by mixing or concomitantly grinding the active substances with a solid carrier.

In general, the formulations comprise from 0.01 to 95% by weight, preferably from 0.1 to 90% by weight, of the active ingredient. The active ingredients are employed in a purity of from 90% to 100%, preferably 95% to 100% (according to NMR spectrum).

Examples of the formulations are:

I. 5 parts by weight of a compound according to the invention are mixed intimately with 95 parts by weight of finely divided kaolin. This gives a dust which comprises 5% by weight of the active ingredient.

II. 30 parts by weight of a compound according to the invention are mixed intimately with a mixture of 92 parts by weight of pulverulent silica gel and 8 parts by weight of paraffin oil which has been sprayed onto the surface of this silica gel. This gives a preparation of the active ingredient with good adhesion (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenyl and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutylnaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-α-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient.

VIII. 20 parts by weight of a compound according to the invention are mixed thoroughly with 3 parts by weight of sodium diisobutylnaphthalene-α-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

Granules, eg. coated granules, impregnated granules and homogeneous granules, can be prepared by binding the active ingredients onto solid carriers. Examples of solid carriers are mineral earths such as silicas, silica gels, silicates, talcs, kaolin, attaclay, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas, and products of vegetable origin such as cereal meal, tree bark meal, wood meal and nut shell meal, cellulose powders, and other solid carriers.

Various types of oils, or herbicides, fungicides, other pesticides, or bactericides, can be added to the active ingredients, if appropriate also only just prior to use (tank mix). These agents can be admixed with the agents according to the invention in a weight ratio of 1:10 to 10:1.

SYNTHESIS EXAMPLES

The protocols given in the synthesis examples which follow were used for obtaining further compounds I by altering the starting compounds as required. The resulting compounds are listed in the tables which follow together with physical data.

1. Preparation of methyl methoxyimino-[2-(2-ethoxyimino-1-methyl-propylideneaminooxy)pyridin-3-yl]acetate

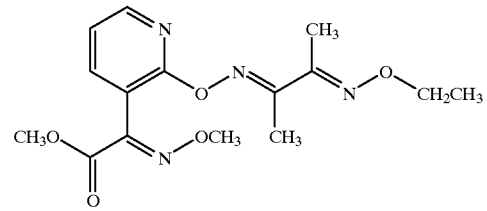

1.a 2-Chloro-3-pyridinecarboxylic acid chloride

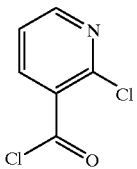

1131 g (9.5 mol) of thionyl chloride were slowly added dropwise at 90° C. to 500 g (3.17 mol) of 2-chloronicotinic acid. The reaction mixture was stirred for 1 hour at 90° C. and freed from thionyl chloride under reduced pressure ("high vacuum") at approximately 40° C. This gave 561 g (100%) of the title compound as colorless crystals.

$^1$H NMR (CDCl$_3$; δ in ppm): 7.45 (m, 1H, pyridyl); 8.42 (dd, 1H, pyridyl); 8.62 (dd, 1H, pyridyl);

IR: 3060, 1786, 1570, 1556, 1392, 1261, 1188, 865, 816, 746, 726 cm$^{-1}$.

1.b 2-(2-Chloropyridin-3-yl)glyoxylic acid cyanide

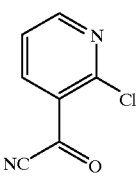

A mixture of 558 g (3.18 mol) of 2-chloro-3-pyridinecarboxylic acid chloride, 566 g (6.23 mol) of copper (I) cyanide and 4000 ml of acetonitrile was stirred for 1 hour at room temperature and then refluxed for 2 hours. The reaction mixture was freed from solvent under reduced pressure ("high vacuum") at approximately 40° C. and the residue was boiled up twice with approximately 1 l of toluene and filtered off. The combined organic phases were freed from solvent under reduced pressure ("high vacuum") at approximately 40° C. This gave 348 g (62%) of the title compound as brown crystals.

IR: 2220, 1730, 1574, 1559, 1399, 1259, 1066, 871, 746, 728 cm$^{-1}$.

1.c Methyl 2-(2-chloropyridin-3-yl)glyoxylate

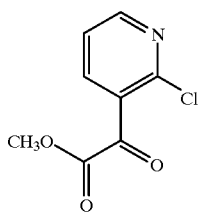

A mixture of 83 g (0.47 mol) of 2-(2-chloropyridin-3-yl) glyoxylic acid cyanide and 500 ml of concentrated HCl was stirred for 8 hours at 50° C. The reaction solution was concentrated at approximately 40° C. under reduced pressure ("high vacuum"), treated twice with 100 ml of toluene, and the solvent was removed at approximately 40° C. under reduced pressure ("high vacuum"). The residue was dissolved in 500 ml of methanol and 5 ml of concentrated H$_2$SO$_4$ and refluxed for 20 hours. The solvent was removed at approximately 40° C. under reduced pressure ("high vacuum"), and the residue was taken up in 500 ml of ethyl acetate and washed with saturated sodium hydrogen carbonate solution. The organic phase was dried over sodium sulfate and the solvent was removed under reduced pressure. The resulting residue was subjected to fractional distillation over a packed column 20 cm in length. This gave 18.3 g (19%) of the title compound as a yellow oil of boiling point 105–115° C. at 0.2–0.3 mbar.

$^1$H NMR (CDCl$_3$; δ in ppm): 4.0 (s, 3H, OCH$_3$); 7.45 (m, 1H, pyridyl); 8.1 (dd, 1H, pyridyl); 8.6 (dd, 1H, pyridyl);

MS m/z (intensity): 199 (M$^+$, 8), 186 (20), 142 (50), 140 (100), 114 (18), 112 (40), 76 (24), 50 (10), 18 (16).

1.d Methyl [2-(2-ethoxyimino-1-methyl-propylideneaminooxy)pyridin-3-yl]glyoxylate

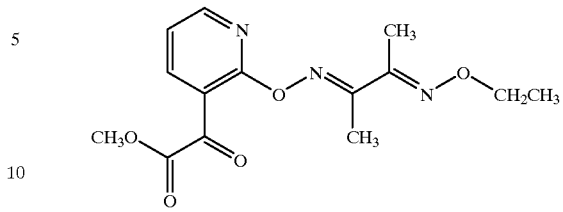

A mixture of 3.25 g (22.6 mmol) of 2-ethoxyimino-3-hydroxyiminobutane and 25 ml of tert-butanol was treated with 2.53 g (22.6 mmol) of potassium tert-butoxide at 60° C. and stirred for 1 hour at the same temperature. The reaction mixture was freed from solvent under reduced pressure ("high vacuum") at approximately 40° C. The residue was introduced into 15 ml of dimethyl sulfoxide, and 4.5 g (22.6 mmol) of methyl 2-(2-chloropyridin-3-yl)glyoxylate, dissolved in 5 ml of dimethyl sulfoxide, were added at 50° C. The mixture was stirred for 20 hours at room temperature, and the reaction mixture was poured onto approximately 150 g of ice and extracted repeatedly with ethyl acetate. The organic phases were combined, washed with water and dried over sodium sulfate, and the solvent was removed under reduced pressure. The resulting residue was purified by column chromatography over silica gel using cyclohexane/ethyl acetate (4/1) as the eluent. This gave 1.56 g (23%) of the title compound as a white solid.

$^1$H NMR (CDCl$_3$; δ in ppm): 1,3 (t, 3H, CH$_3$); 2.04 (s, 3H, CH$_3$); 2.3 (s, 3H, CH$_3$); 3.82 (s, 3H, OCH$_3$); 4.28 (q, 2H, OCH$_2$); 7.22 (m, 1H, pyridyl); 8.1 (dd, 1H, pyridyl); 8.5 (dd, 1H, pyridyl);

M.P.: 75° C.

1.e Methyl methoxyimino-[2-(2-ethoxyimino-1-methylpropylideneaminooxy)pyridin-3-yl]-glyoxylate

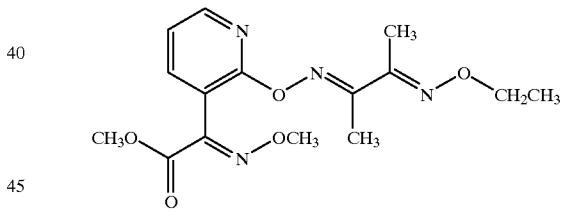

A mixture of 800 mg (2.6 mmol) of methyl [2-(2-ethoxyimino-1-methylpropylideneaminooxy)pyridin-3-yl]-glyoxylate and 410 mg of pyridine in 10 ml of methanol was treated with 240 mg (2.9 mmol) of O-methylhydroxylamine hydrochloride and heated for 1 hour to 50° C. The reaction mixture was freed from solvent under reduced pressure, and the residue was taken up in ethyl acetate and washed with dilute aqueous NaCl solution. The organic phase was dried over sodium sulfate and the solvent was removed under reduced pressure. The resulting residue was purified by column chromatography over silica gel using cyclohexane/ethyl acetate (4/1) as the eluent. This gave 480 mg (55%) of the title compound as a white solid.

$^1$H NMR (CDCl$_3$; δ in ppm): 1.3 (t, 3H, CH$_3$); 2.1 (s, 3H, CH$_3$); 2.2 (s, 3H, CH$_3$); 3.82 (s, 3H, OCH$_3$); 4.06 (s, 3H, OCH$_3$); 4.12 (q, 2H, OCH$_2$); 7.1 (m, 1H, pyridyl); 7.7 (dd, 1H, pyridyl); 8.38 (dd, 1H, pyridyl);

M.p.: 71° C.

150 mg (17%) of methyl Z-methoxyimino-[2-E,E-(2-ethoxyimino-1-methylpropylideneaminooxy)pyridin-3-yl]

glyoxylate were isolated as a second product in the form of a yellow oil.

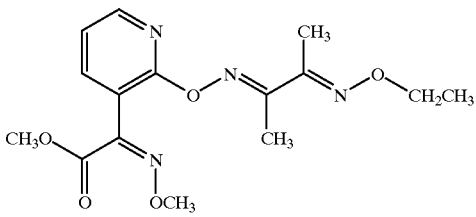

¹H NMR (CDCl₃; δ in ppm): 1.3 (t, 3H, CH₃); 2.18 (s, 3H, CH₃); 2.24 (s, 3H, CH₃); 3.8 (s, 3H, OCH₃); 4.06 (s, 3H, OCH₃); 4.12 (q, 2H, OCH₂); 7.14 (m, 1H, pyridyl); 8.0 (dd, 1H, pyridyl); 8.4 (dd, 1H, pyridyl);

IR: 2980, 2940, 1752, 1587, 1418, 1252, 1227, 1209, 1048, 1027, 913, 893 cm⁻¹.

2. Preparation of N-methyl-methoxyimino-[2-(2-ethoxyimino-1-methylpropylideneaminooxy)pyridin-3-yl]acetamide

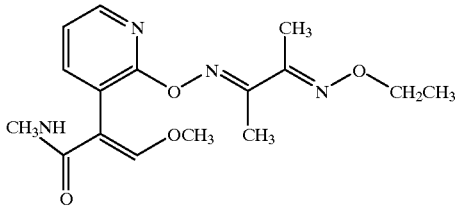

A mixture of 260 mg (0.77 mmol) of methyl oxyimino-[2-(2-ethoxyimino-1-methylpropylideneaminooxy)pyridin-3-yl]glyoxylate and 2 g of 40% strength aqueous methylamine solution in 3 ml of tetrahydrofuran was refluxed for 2 hours. The reaction mixture was freed from solvent under reduced pressure; the residue was taken up in ethyl acetate; and the mixture was washed with dilute aqueous NaCl solution. The organic phase was dried over sodium sulfate and the solvent was removed under reduced pressure. This gave 240 mg (93%) of the title compound as a white solid.

¹H NMR (CDCl₃; δ in ppm): 1.3 (t, 3H, CH₃); 2.1 (s, 3H, CH₃); 2.2 (s, 3H, CH₃); 2.90, 2.92 (in each case s, 3H, NCH₃); 3.95 (s, 3H, OCH₃); 4.25 (q, 2H, OCH₂); 6.8 (m, 1H, NH); 7.1 (m, 1H, pyridyl); 7.65 (dd, 1H, pyridyl); 8.35 (dd, 1H, pyridyl);

M.p.: 110° C.

3. Preparation of methyl methoxyimino-[2-(2-ethoxyimino-1-methylpropylideneaminooxy)pyridin-3-yl]acrylate

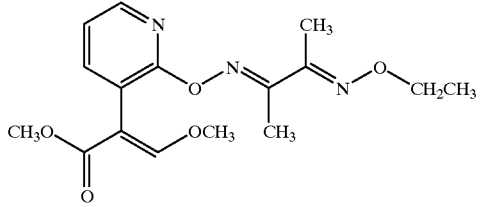

A mixture of 650 mg (1.9 mmol) of methoxymethyltriphenyl-phosphonium chloride and 340 g (1.9 mmol) of sodium methoxide solution (30% strength in methanol) in 8 ml of dimethylformamide was stirred for 10 minutes at room temperature. The reaction mixture was subsequently treated with 400 mg (0.95 mmol) of methyl [2-(2-ethoxyimino-1-methylpropylideneaminooxy)pyridin-3-yl]glyoxylate, dissolved in 4 ml of dimethylformamide. The reaction mixture was stirred for 4 hours at room temperature, hydrolyzed with 20 ml of water, and the aqueous phase was extracted with ethyl acetate. The combined organic phases were dried over sodium sulfate and the solvent was removed under reduced pressure. This gave 120 mg (38%) of the title compound as a yellow oil.

¹H NMR (CDCl₃; δ in ppm): 1.3 (t, 3H, CH₃); 2.16 (s, 3H, CH₃); 2.2 (s, 3H, CH₃); 3.7 (s, 3H, OCH₃); 3.84 (s, 3H, OCH₃); 4.22 (q, 2H, OCH₂); 7.1 (m, 1H, pyridyl); 7.58 (s, 1H, CH); 7.6 (dd, 1H, pyridyl); 8.25 (dd, 1H, pyridyl);

IR: 2950, 2920, 2850, 1713, 1435, 1416, 1291, 1263, 1238, 1132, 1105, 1050, 914 cm⁻¹.

TABLE (1.8)

| No. | R | R¹ | R³ | Y¹ | R⁴ | ¹H NMR [δ in ppm; CDCl₃] |
|---|---|---|---|---|---|---|
| 1 | Ic | CH₃ | CH₃ | O | CH₃ | 2.1 (s, 3H, CH₃); 2.2 (s, 3H, CH₃); 3.82 (s, 3H, OCH₃); 4.0 (s, 3H, OCH₃); 4.05 (s, 3H, OCH₃); 7.15 (m, 1H, Py); 7.7 (dd, 1H, Py); 8.35 (dd, 1H, Py) |
| 2 | Ic | CH₃ | CH₃ | O | CH(CH₃)₂ | 1.3 (d, 6H, 2XCH₃); 2.1 (s, 3H, CH₃); 2.2 (s, 3H, CH₃); 3.84 (s, 3H, OCH₃); 4.06 (s, 3H, OCH₃); 4.45 (m, 1H, CH); 7.14 (m, 1H, Py); 7.7 (dd, 1H, Py); 8.38 (dd, 1H, Py) |
| 3 | Ic | CH₃ | CH₃ | O | CH₂C≡CH | 2.1 (s, 3H, CH₃); 2.2 (s, 3H, CH₃); 2.5 (s, 1H, CH); 3.82 (s, 3H, OCH₃); 4.05 (s, 3H, OCH₃); 4.8 (s, 2H, OCH₂); 7.1 (m, 1H, Py); 7.7 (dd, 1H, Py); 8.38 (dd, 1H, Py) |

TABLE-continued

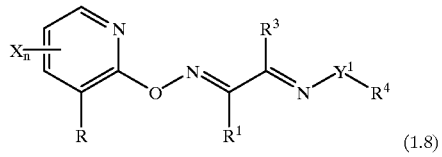

(1.8)

| No. | R | R¹ | R³ | Y¹ | R⁴ | ¹H NMR [δ in ppm; CDCl₃] |
|---|---|---|---|---|---|---|
| 4 | Ic | CH₃ | CH₃ | O | CH₂—C₆H₅ | 2.1 (s, 3H, CH₃); 2.2 (s, 3H, CH₃); 3.8 (s, 3H, OCH₃); 4.05 (s, 3H, OCH₃); 5.2 (s, 2H, OCH₂); 7.1 (m, 1H, Py); 7.32 (m, 5H, benzyl); 7.7 (dd, 1H, Py); 8.35 (dd, 1H, Py) |
| 5 | Id | CH₃ | CH₃ | O | CH₃ | 2.1 (s, 3H, CH₃); 2.2 (s, 3H, CH₃); 2.89; 2.90 (in each case s, 3H, NCH₃); 3.95 (s, 3H, OCH₃); 4.0 (s, 3H, OCH₃); 6.95 (m, 1H, NH); 7.1 (m, 1H, Py); 7.65 (dd, 1H, Py); 8.3 (dd, 1H, Py) |
| 6 | Id | CH₃ | CH₃ | O | CH(CH₃)₂ | 1.35 (d, 6H, 2xCH₃); 2.1 (s, 3H, CH₃); 2.2 (s, 3H, CH₃); 2.90; 2.92 (in each case s, 3H, NCH₃); 3.95 (s, 3H, OCH₃); 4.4 (m, 1H, CH); 6.85 (m, 1H, NH); 7.1 (m, 1H, Py); 7.65 (dd, 1H, Py); 8.35 (dd, 1H, Py) |
| 7 | Id | CH₃ | CH₃ | O | CH₂C≡CH | 2.1 (s, 3H, CH₃); 2.2 (s, 3H, CH₃); 2.5 (s, 1H, CH); 2.90; 2.92 (in each case s, 3H, NCH₃); 3.95 (s, 3H, OCH₃); 2.5 (s, 1H, CH); 4.8 (s, 2H, OCH₂); 6.75 (m, 1H, NH); 7.1 (m, 1H, Py); 7.7 (dd, 1H, Py); 8.35 (dd, 1H, Py) |
| 8 | Id | CH₃ | CH₃ | O | CH₂—C₆H₅ | 2.1 (s, 3H, CH₃); 2.2 (s, 3H, CH₃); 2.90; 2.92 (in each case s, 3H, NCH₃); 3.95 (s, 3H, OCH₃); 5.22 (s, 2H, OCH₂); 6.75 (m, 1H, NH); 7.1 (m, 1H, Py); 7.38 (m, 5H, benzyl); 7.64 (dd, 1H, Py); 8.36 (dd, 1H, Py) |
| 9 | Ic | CH₂CH₃ | CH₃ | O | CH₃ | 1.1 (t, 3H, CH₃); 2.1 (s, 3H, CH₃); 2.75 (q, 2H, CH₂); 3.84 (s, 3H, OCH₃); 4.0 (s, 3H, OCH₃); 4.06 (s, 3H, OCH₃); 7.12 (m, 1H, Py); 7.65 (dd, 1H, Py); 8.38 (dd, 1H, Py) |
| 10 | Ic | CH₂CH₃ | CH₃ | O | CH(CH₃)₂ | 1.12 (t, 3H, CH₃); 1.3 (d, 6H, 2xCH₃); 2.05 (s, 3H, CH₃); 2.75 (q, 2H, CH₂); 3.82 (s, 3H, OCH₃); 4.06 (s, 3H, OCH₃); 4.45 (m, 1H, CH); 7.1 (m, 1H, Py); 7.65 (dd, 1H, Py); 8.36 (dd, 1H, Py) |
| 11 | Ic | CH₂CH₃ | CH₃ | O | CH₂C≡CH | 1.1 (t, 3H, CH₃); 2.1 (s, 3H, CH₃); 2.5 (s, 1H, CH); 2.75 (q, 2H, CH₂); 3.86 (s, 3H, OCH₃); 4.06 (s, 3H, OCH₃); 4.8 (s, 2H, OCH₂); 7.14 (m, 1H, Py); 7.65 (dd, 1H, Py); 8.38 (dd, 1H, Py) |
| 12 | Id | CH₂CH₃ | CH₃ | O | CH₃ | 1.1 (t, 3H, CH₃); 2.06 (s, 3H, CH₃); 2.75 (q, 2H, CH₂); 2.90; 2.92 (in each case s, 3H, NCH₃); 3.94 (s, 3H, OCH₃); 4.0 (s, 3H, OCH₃); 6.8 (m, 1H, NH); 7.1 (m, 1H, Py); 7.65 (dd, 1H, Py); 8.36 (dd, 1H, Py) |
| 13 | Id | CH₂CH₃ | CH₃ | O | CH(CH₃)₂ | 1.1 (t, 3H, CH₃); 1.25 (d, 6H, 2xCH₃); 2.05 (s, 3H, CH₃); 2.75 (q, 2H, CH₂); 2.90; 2.92 (in each case s, 3H, NCH₃); 3.94 (s, 3H, OCH₃) 4.42 (m, 1H, CH); 6.8 (m, 1H, NH); 7.1 (m, 1H, Py); 7.65 (dd, 1H, Py); 8.36 (dd, 1H, Py) |
| 14 | Id | CH₂CH₃ | CH₃ | O | CH₂C≡CH | 1.12 (t, 3H, CH₃); 2.1 (s, 3H, CH₃); 2.5 (s, 1H, CH); 2.75 (q, 2H, CH₂); 2.90; 2.92 (in each case s, 3H, NCH₃); 3.96 (s, 3H, OCH₃); 4.8 (s, 2H, OCH₂); 6.8 (m, 1H, NH); 7.12 (m, 1H, Py); 7.65 (dd, 1H, Py); 8.35 (dd, 1H, Py) |

TABLE-continued (1.8)

| No. | R | R$^1$ | R$^3$ | Y$^1$ | R$^4$ | $^1$H NMR [δ in ppm; CDCl$_3$] |
|---|---|---|---|---|---|---|
| 15 | Ic | CH$_3$ | CH$_3$ | O | CH$_2$CH$_3$ | 1.3 (t, 3H, CH$_3$); 2.1 (s, 3H, CH$_3$); 2.2 (s, 3H, CH$_3$); 3.82 (s, 3H, OCH$_3$); 4.06 (s, 3H, OCH$_3$); 4.12 (q, 2H, OCH$_2$); 7.1 (m, 1H, Py); 7.7 (dd, 1H, Py); 8.38 (dd, 1H, Py) |
| 16 | Id | CH$_3$ | CH$_3$ | O | CH$_2$CH$_3$ | 1.3 (t, 3H, CH$_3$); 2.1 (s, 3H, CH$_3$); 2.2 (s, 3H, CH$_3$); 2.90; 2.92 (in each case s, 3H, NCH$_3$); 3.95 (s, 3H, OCH$_3$); 4.25 (q, 2H, OCH$_2$); 6.8 (m, 1H, NH); 7.1 (m, 1H, Py); 7.65 (dd, 1H, Py); 8.35 (dd, 1H, Py) |
| 17 | Ia | CH$_3$ | CH$_3$ | O | CH$_2$CH$_3$ | 1.3 (t, 3H, CH$_3$); 2.16 (s, 3H, CH$_3$); 2.2 (s, 3H, CH$_3$); 3.7 (s, 3H, OCH$_3$); 3.84 (s, 3H, OCH$_3$); 4.22 (q, 2H, OCH$_2$); 7.1 (m, 1H, Py); 7.58 (s, 1H, CH); 7.6 (dd, 1H, Py); 8.25 (dd, 1H, Py) |
| 18 | Ic | CH$_2$CH$_3$ | CH$_3$ | O | CH$_2$CH$_3$ | 1.1 (t, 3H, CH$_3$); 1.3 (t, 3H, CH$_3$); 2.1 (s, 3H, CH$_3$); 2.75 (q, 2H, CH$_2$); 3.85 (s, 3H, OCH$_3$); 4.06 (s, 3H, OCH$_3$); 4.24 (q, 2H, OCH$_2$); 7.1 (m, 1H, Py); 7.68 (dd, 1H, Py); 8.38 (dd, 1H, Py) |
| 19 | Ia | CH$_2$CH$_3$ | CH$_3$ | O | CH(CH$_3$)$_2$ | 1.1 (t, 3H, CH$_3$); 1.15 (d, 6H, 2xCH$_3$); 2.1 (s, 3H, CH$_3$); 2.74 (q, 2H, CH$_2$); 3.7 (s, 3H, OCH$_3$); 3.84 (s, 3H, OCH$_3$); 4.42 (m, 1H, CH); 7.1 (m, 1H, Py); 7.58 (m, 2H, 1xCH, 1xPy); 8.3 (dd, 1H, Py) |

Ia=C[CO$_2$CH$_3$]=CHOCH$_3$; Ib=C[CO$_2$CH$_3$]=CHCH$_3$;
Ic=C[CO$_2$CH$_3$]=NOCH$_3$; Id=C[CONHCH$_3$]=NOCH$_3$
Py=pyridyl Examples of the Action Against Harmful Fungi The fungicidal function of the compounds of the general formula I was demonstrated by the following experiments:

The active ingredients were formulated, separately or jointly, as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (nonionic emulsifier based on ethoxylated castor oil) and diluted with water to give the desired concentration.

Activity Against *Erysiphe graminis* var. *tritici* (powdery mildew of wheat)

Leaves of wheat seedlings (cultivar: "Frühgold") were first treated with the aqueous preparation of the active ingredients (rate of application: 250 ppm). After approximately 24 hours, the plants were dusted with spores of powdery mildew of wheat (*Erysiphe graminis* var. *tritici*). The treated plants were subsequently incubated for 7 days at 20–22° C. and a relative atmospheric humidity of 75–80%. The extent of fungal development was subsequently determined.

In this test, the infection level of plants which had been treated with the compounds 1, 3 and 7 according to the invention was 15% and less, while the infection level of the untreated (control) plants was 75%.

Activity Against *Plasmopara viticola* (downy mildew grapevines)

Grapevines in pots (cultivar: "Müller Thurgau") were sprayed to run off with the preparation of active ingredient (rate of application: 250 ppm). After 8 days, the plants were sprayed with a zoospore suspension of the fungus *Plasmopara viticola* and kept for 5 days at 20–30° C. and high atmospheric humidity. Thereupon, prior to assessment, the plants were kept for 16 hours at high atmospheric humidity. The test was evaluated visually.

In this test, the infection level of the plants which had been treated with the compounds 1, 3 and 7 according to the invention was 15% and less, while the infection level of the untreated (control) plants was 70%.

Examples of the Action Against Animal Pests

The activity of the compounds of the general formula I against animal pests was demonstrated by the following experiments:

The active ingredients were formulated
 a. as a 0.1% strength solution in acetone or
 b. as a 10% emulsion in a mixture of 70% by weight of cyclohexanone, 20% by weight of Nekanil® LN (Lutensol® AP6, wetting agent having emulsifying and dispersant action based on ethoxylated alkylphenols) and 10% by weight of Wettol® EM (non-ionic emulsifier based on ethoxylated castor oil)

and diluted to give the desired concentration, using acetone in the case of a. and water in the case of b.

After the experiments had been concluded, in each case the lowest concentration at which the compounds still caused an 80 to 100% inhibition, or mortality, in comparison with untreated controls was determined (limit or minimal concentration).

We claim:

1. A pyridine compound of the formula I

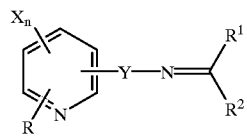

wherein:

X is cyano, nitro, halogen, $C_1$–$C_4$-alkyl, $C_1$–$C_4$-haloalkyl, $C_1$–$C_4$-alkoxy, $C_1$–$C_4$-haloalkoxy and $C_3$–$C_6$-cycloalkyl;

n is 0, 1, 2 or 3, it being possible for the substituents X to be different when n is greater than 1;

Y is oxygen or nitrogen, the nitrogen atom having attached to it a hydrogen atom or a $C_1$–$C_4$-alkyl group;

R is $C(CO_2CH_3)$=$CHCH_3$, $C(CO_2CH_3)$=$CHOCH_3$, $C(CO_2CH_3)$=$NOCH_3$, $C(CONH_2)$=$NOCH_3$ or $C(CONHCH_3)$=$NOCH_3$;

$R^1$ is hydrogen, hydroxyl, cyano, halogen,
$C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_3$–$C_6$-cycloalkyl, $C_3$–$C_6$-cycloalkyl-$C_1$–$C_4$-alkyl,
aryl, aryl-$C_1$–$C_4$-alkyl, aryloxy-$C_1$–$C_4$-alkyl and aryl-$C_1$–$C_4$-alkoxy, it being possible for the aromatic rings to be partially or fully halogenated and/or to have attached to them one to three of the following radicals: cyano, nitro, $C_1$–$C_6$-alkyl, $C_1$–$C_6$-haloalkyl, $C_1$–$C_6$-alkoxy, $C_1$–$C_6$-haloalkoxy, and $C(CH_3)$=$N$-$A^1$-$R^a$;

$R^a$ is $C_1$–$C_6$-alkyl, $A^1$ is oxygen or nitrogen, the nitrogen atom having attached to it a hydrogen atom or a $C_1$–$C_4$-alkyl group;

$R^2$ is unsubstituted or substituted alkenyl, or
—Q—C($R^3$)=N-$Y^1$-$R^4$ where
Q is a direct bond, $CH_2$, $CH(CH_3)$, $CH(CH_2CH_3)$ or 1,1-cyclopropyl;
$Y^1$ is oxygen or nitrogen, the nitrogen atom having attached to it a hydrogen atom or a $C_1$–$C_4$-alkyl group;
$R^3$ is one of the groups listed under $R^1$, or unsubstituted or substituted cycloalkoxy, heterocyclyloxy, aryloxy, hetaryloxy, arylthio and hetarylthio;
$R^4$ is unsubstituted or substituted $C_1$–$C_{10}$-alkyl, $C_3$–$C_6$-cycloalkyl, $C_2$–$C_{10}$-alkenyl, $C_2$–$C_{10}$-alkynyl, $C_1$–$C_{10}$-alkylcarbonyl, $C_2$–$C_{10}$-alkenylcarbonyl, $C_2$–$C_{10}$-alkynylcarbonyl or $C_1$–$C_{10}$-alkylsulfonyl;
unsubstituted or substituted aryl, hetaryl, arylcarbonyl, hetarylcarbonyl, arylsulfonyl or hetarylsulfonyl;

or a salt thereof.

2. A compound of the formula I as claimed in claim 1 wherein $R^2$ is a substituted alkenyl, the substituents being from one to three of the following radicals has the following meanings:

cyano, nitro, hydroxyl, mercapto, amino, carboxyl, aminocarbonyl, aminothiocarbonyl,
$C_1$–$C_6$-alkylsulfonyl, $C_1$–$C_6$-alkylsulfoxyl, $C_1$–$C_6$-alkylcarbonyl, $C_3$–$C_6$-cycloalkyl, $C_1$–$C_6$-alkoxy, $C_1$–$C_6$-haloalkoxy, $C_1$–$C_6$-alkoxycarbonyl, $C_1$–$C_6$-alkylthio, $C_1$–$C_6$-alkylamino, di-$C_1$–$C_6$-alkylamino, $C_1$–$C_6$-alkylaminocarbonyl, di-$C_1$–$C_6$-alkylaminocarbonyl, $C_1$–$C_6$-alkylaminothiocarbonyl, di-$C_1$–$C_6$-alkylaminothiocarbonyl, $C_2$–$C_6$-alkenyloxy, benzyloxy, aryl, aryloxy, hetaryl and hetaryloxy, wherein the aromatic ring are substituted or unsubstituted.

3. A compound of the formula I as claimed in claim 1 where $R^2$ is the group —C($R^3$)=N—$Y^1$—$R^4$ wherein:

$Y^1$ is O, NH or N($CH_3$);

$R^4$ is hydrogen,
$C_1$–$C_6$-alkyl which optionally has attached to it one of the following groups: $C_1$–$C_4$-alkoxy, $C_3$–$C_6$-cycloalkyl which is unsubstituted or substituted or phenyl which is unsubstituted or substituted;
$C_3$–$C_6$-alkenyl, $C_3$–$C_6$-haloalkenyl, $C_3$–$C_6$-alkynyl, $C_3$–$C_6$-haloalkynyl or $C_3$–$C_6$-cycloalkyl which is unsubstituted or substituted by customary groups, $R^3$ is hydrogen, cyano, halogen, $C_1$–$C_4$-alkyl, $C_1$–$C_2$-haloalkyl, $C_1$–$C_4$-alkoxy, $C_1$–$C_2$-haloalkoxy or $C_3$–$C_6$-cycloalkyl.

4. A compound of the formula I.8 as claimed in claim 1

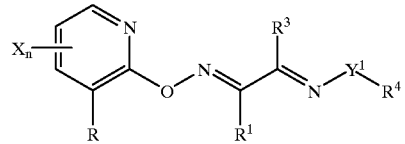

wherein:

R is $C(CO_2CH_3)$=$CHCH_3$, $C(CO_2CH_3)$=$CHOCH_3$, $C(CO_2CH_3)$=$NOCH_3$ or $C(CONHCH_3$=$NOCH_3$;

X is cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

n is 0 or 1;

$R^1$ is hydrogen, cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

$R^3$ is hydrogen, cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

$Y^1$ is O, NH or N($CH_3$);

$R^4$ is hydrogen,
$C_1$–$C_6$-alkyl which may have attached to it one of the following groups: $C_1$–$C_4$-alkoxy, $C_3$–$C_6$-cycloalkyl which is unsubstituted or substituted by customary groups or phenyl which is unsubstituted or substituted;
$C_3$–$C_6$-alkenyl, $C_3$–$C_6$-haloalkenyl, $C_3$–$C_6$-alkynyl, $C_3$–$C_6$-haloalkynyl or $C_3$–$C_6$-cycloalkyl which is unsubstituted or substituted by customary groups.

5. A compound of the formula I as claimed in claim 1 where $R^2$ is the group —C($R^x$)=$CR^yR^z$ with the following meanings:

$R^x$ is hydrogen, cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

$R^y$ is hydrogen,
$C_1$–$C_6$-alkyl which may be partially or fully halogenated and/or may have attached to it one to three (in particular one) of the following groups: $C_1$–$C_4$-alkoxy, $C_3$–$C_6$-cycloalkyl which is unsubstituted or substituted by customary groups or phenyl which is unsubstituted or substituted;

$C_1$–$C_6$-alkoxy, $C_1$–$C_6$-haloalkoxy, $C_3$–$C_6$-cycloalkyl which is unsubstituted or substituted by customary groups; phenyl which is unsubstituted or substituted by customary groups, pyridyl which is unsubstituted or substituted by customary groups or pyrimidyl which is unsubstituted or substituted;

$R^z$ is hydrogen, cyano, halogen, $C_1$–$C_4$-alkyl, $C_1$–$C_2$-haloalkyl and $C_3$–$C_6$-cycloalkyl, or $R^y$ and $R^x$ together with the double bond to which they are attached are $C_4$–$C_6$-cycloalkenyl.

6. A compound of the formula I.12 as claimed in claim 1

(I.12)

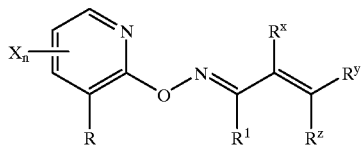

wherein:

R is $C(CO_2CH_3)=CHCH_3$, $C(CO_2CH_3)=CHOCH_3$, $C(CO_2CH_3)=NOCH_3$ or $C(CONHCH_3=NOCH_3$;

X is cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

n is 0 or 1;

$R^1$ is hydrogen, cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

$R^x$ is hydrogen, cyano, halogen, $C_1$–$C_4$-alkyl, $C_1$–$C_2$-haloalkyl, $C_1$–$C_4$-alkoxy, $C_1$–$C_2$-haloalkoxy and $C_3$–$C_6$-cycloalkyl;

$R^y$ is hydrogen,
$C_1$–$C_6$-alkyl which may be partially or fully halogenated and/or may have attached to it one to three (in particular one) of the following groups: $C_1$–$C_4$-alkoxy, $C_3$–$C_6$-cycloalkyl which is unsubstituted or substituted by customary groups or phenyl which is unsubstituted or substituted;
$C_1$–$C_6$-alkoxy, $C_1$–$C_6$-haloalkoxy,
$C_3$–$C_6$-cycloalkyl which is unsubstituted or substituted by customary groups; phenyl which is unsubstituted or substituted by customary groups, pyridyl which is unsubstituted or substituted by customary groups or pyrimidyl which is unsubstituted or substituted;

$R^z$ is hydrogen, cyano, halogen, $C_1$–$C_4$-alkyl, $C_1$–$C_2$-haloalkyl and $C_3$–$C_6$-cycloalkyl, or $R^y$ and $R^x$ together with the double bond to which they are attached are $C_4$–$C_6$-cycloalkenyl.

7. A compound as claimed in claim 1 where n is 0 or 1 and, when n is 1, X is fluorine, chlorine, methyl or trifluoromethyl.

8. A compound as claimed in any of claim 1 where $R^1$ is $C_1$–$C_3$-alkyl.

9. A compound as claimed in claim 4 where $R^3$ is $C_1$–$C_3$-alkyl,
$Y^1$ is oxygen and
$R^4$ is $C_1$–$C_4$-alkyl, $C_3$–$C_4$-alkynyl or benzyl.

10. A compound as claimed in claim 6 where $R^x$ is $C_1$–$C_4$-alkyl,
$R^y$ is $C_1$–$C_4$-alkyl or phenyl which for its part may have attached to it one to three of the following radicals: halogen, $C_1$–$C_4$-alkyl or haloalkyl; and
$R^z$ is hydrogen.

11. A compound of the formula I as claimed in claim 1 where the radical R and the group —Y—N=$CR^1R^2$ are bonded to two adjacent C atoms of the pyridyl ring.

12. A process for the preparation of the pyridine compounds of the formula I as claimed in claim 1 where R is $C(CO_2CH_3)=CHCH_3$, $C(CO_2CH_3)=CHOCH_3$ or $C(CO_2CH_3)=NOCH_3$, which comprises first converting a pyridinecarboxylic acid of the formula IIa (IIa)

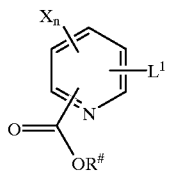

where $L^1$ is a nucleophilically exchangeable leaving group and R# is hydrogen or a $C_1$–$C_4$-alkyl group into the acid chloride IIb (IIb)

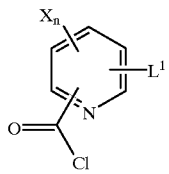

and subsequently into the acid cyanide IIc (IIc)

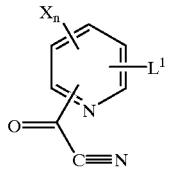

reacting IIc via a Pinner reaction to give the corresponding α-keto ester IIIa (IIIa)

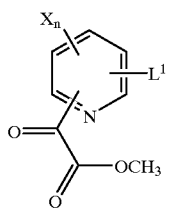

subsequently reacting IIIa with an oxime of the formula IV (IV)

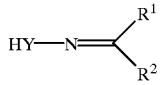

in the presence of a base to give the corresponding α-keto ester IIIb

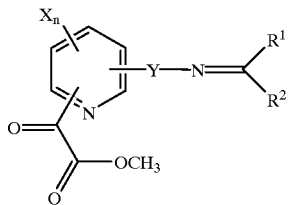
(IIIb)

and subsequently converting IIIb either a) with a Wittig or Wittig-Horner reagent of the formula Va

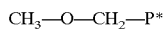
(Va)

where P* is a phosphonate or a phosphonium halide radical into the corresponding compound Ia, [R=C(CO$_2$CH$_3$)=CHOCH$_3$, or b) with a Wittig or Wittig-Horner reagent of the formula Vb

(Vb)

into the corresponding compound Ib [R=C(CO$_2$CH$_3$)=CHCH$_3$], or c) with O-methylhydroxylamine or a salt thereof (Vc)

(Vc)

where Z$^-$ is a halide anion into the corresponding compound Ic, wherein R is C(CO$_2$CH$_3$)=NOCH$_3$.

13. A process for the preparation of the compounds Va and Vc as set forth in claim 12, which comprises converting a pyridine compound of the formula VI

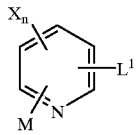
(VI)

where L$^1$ is a nucleophilically exchangeable leaving group and M is an organometallic radical with a compound VII

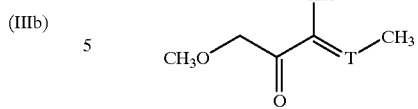
(VII)

where T is CH, CHO or NO and Hal is a halogen atom in the presence of a catalyst into the corresponding pyridine derivative of the formula VIII

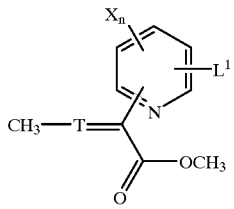
(VIII)

and subsequently reacting VIII with an oxime of the formula IV as set forth in claim 12 in the presence of a base to give Ia or Ic.

14. A process for the preparation of the compounds I as claimed in claims 12 where R is C(CONHCH$_3$)=NOCH$_3$, which comprises converting a compound of the formula Ic as set forth in claim 12 with methylamine or a salt thereof (IX)

(IX)

where Z$^-$ is a halide anion into the corresponding compound Id, wherein R is C(CONHCH$_3$) NOCH$_3$].

15. A composition which is suitable for controlling animal pests or harmful fungi, comprising a solid or liquid carrier and a compound of the formula I as claimed in claim 1.

16. A method of controlling harmful fungi, which comprises treating the fungi, or the materials, the plants, the soil or seed to be protected against fungal infection with an effective amount of a compound of the formula I as claimed in claim 1.

17. A method of controlling animal pests, which comprises treating the pests, or the materials, plants, the soil or seed to be protected against them with an effective amount of a compound of the formula I as claimed in any of claim 1.

* * * * *

UNITED STATES PATENT AND TRADEMARK OFFICE
CERTIFICATE OF CORRECTION

PATENT NO. : 6,228,810 B1
DATED : May 8, 2001
INVENTOR(S) : Röhl et al.

It is certified that error appears in the above-identified patent and that said Letters Patent is hereby corrected as shown below:

Column 95, claim 2,
Lines 61-62, delete "has the following meanings:".

Column 96, claim 3,
Line 17, delete "by customary groups".

Column 96, claim 4,
Lines 49 and 50, delete "by customary groups".
Line 54, delete "by customary groups".

Column 97, claim 6,
Line 40, delete "by customary groups".

Column 97, claim 8,
Line 55, delete "any of".

Column 99, claim 12,
Line 22, "[R" should be -- R --.

UNITED STATES PATENT AND TRADEMARK OFFICE
CERTIFICATE OF CORRECTION

PATENT NO. : 6,228,810 B1
DATED : May 8, 2001
INVENTOR(S) : Röhl et al.

It is certified that error appears in the above-identified patent and that said Letters Patent is hereby corrected as shown below:

Column 100, claim 14,
Line 35, "C(CONHCH$_3$) NOCH$_3$]" should be -- C(CONHCH$_3$)=NOCH$_3$ --.

Column 100, claim 17,
Line 47, delete "any of".

Signed and Sealed this

Twenty-fifth Day of December, 2001

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.   : 6,228,810 B1
DATED        : May 8, 2001
INVENTOR(S)  : Röhl et al.

It is certified that error appears in the above-identified patent and that said Letters Patent is hereby corrected as shown below:

<u>Title page,</u>
Below Item [76], Inventors, insert the following:
-- [73] Assignee: BASF Aktiengesellschaft Ludwigshafen (DE) --;

Above Item [57], ABSTRACT, insert the folllowing:
-- [74] *Attorney, Agent, or Firm*—Keil & Weinkauf --.

Signed and Sealed this

Twenty-eighth Day of May, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO.   : 6,228,810 B1
DATED        : May 8, 2001
INVENTOR(S)  : Röhl et al.

It is certified that error appears in the above-identified patent and that said Letters Patent is hereby corrected as shown below:

<u>Title page,</u>
Below Item [76], Inventors, insert the following:
-- [73] Assignee: BASF Aktiengesellschaft Ludwigshafen (DE) --;

Above Item [57], ABSTRACT, insert the folllowing:
-- [74] *Attorney, Agent, or Firm*—Keil & Weinkauf --.

This certifcate supersedes Certificate of Correction issued May 28, 2002 since the patent number did not appear on Certificate of Correction listing for May 28, 2002.

Signed and Sealed this

Sixteenth Day of July, 2002

*Attest:*

JAMES E. ROGAN
*Attesting Officer*   *Director of the United States Patent and Trademark Office*